(12) United States Patent
Saiah et al.

(10) Patent No.: US 10,683,308 B2
(45) Date of Patent: Jun. 16, 2020

(54) RAPAMYCIN ANALOGS AND USES THEREOF

(71) Applicant: Navitor Pharmaceuticals, Inc., Cambridge, MA (US)

(72) Inventors: Eddine Saiah, Brookline, MA (US); David John O'Neill, Arlington, MA (US)

(73) Assignee: Navitor Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/758,861

(22) PCT Filed: Sep. 9, 2016

(86) PCT No.: PCT/US2016/050913
§ 371 (c)(1),
(2) Date: Mar. 9, 2018

(87) PCT Pub. No.: WO2017/044720
PCT Pub. Date: Mar. 16, 2017

(65) Prior Publication Data
US 2019/0031683 A1 Jan. 31, 2019

Related U.S. Application Data

(60) Provisional application No. 62/217,372, filed on Sep. 11, 2015.

(51) Int. Cl.
C07D 498/18 (2006.01)
C07D 519/00 (2006.01)
A61K 47/55 (2017.01)

(52) U.S. Cl.
CPC ........... C07D 498/18 (2013.01); A61K 47/55 (2017.08); C07D 519/00 (2013.01)

(58) Field of Classification Search
None
See application file for complete search history.

(56) References Cited

U.S. PATENT DOCUMENTS

| | | | |
|---|---|---|---|
| 5,639,600 | A | 6/1997 | McGrath et al. |
| 7,087,648 | B1 | 8/2006 | McGrath |
| 7,390,799 | B2 | 6/2008 | Bruncko et al. |
| 8,138,347 | B2 | 3/2012 | Adams et al. |
| 10,117,945 | B2 * | 11/2018 | Shokat .............. A61K 31/436 |
| 2006/0025356 | A1 | 2/2006 | Yang et al. |
| 2013/0184661 | A1 | 7/2013 | Beaton et al. |
| 2014/0271897 | A1 | 9/2014 | Pathak |

FOREIGN PATENT DOCUMENTS

| | | |
|---|---|---|
| WO | 2001042246 | 6/2001 |
| WO | 2002088112 | 11/2002 |
| WO | 2003063794 | 8/2003 |
| WO | 2004019973 | 3/2004 |
| WO | 2004089925 | 10/2004 |
| WO | 2004106328 | 12/2004 |
| WO | 2005007623 | 1/2005 |
| WO | 2005113554 | 12/2005 |
| WO | 2006078846 | 7/2006 |
| WO | 2006122806 | 11/2006 |
| WO | 2007016176 | 2/2007 |
| WO | 2007044729 | 4/2007 |
| WO | 2007053452 | 5/2007 |
| WO | 2007070514 | 6/2007 |
| WO | 2007084786 | 7/2007 |
| WO | 2007129161 | 11/2007 |
| WO | 2008039218 | 4/2008 |
| WO | 2008109943 | 9/2008 |
| WO | 2008110491 | 9/2008 |
| WO | 2008118802 | 10/2008 |
| WO | 2009114512 | 9/2009 |
| WO | 2011090760 | 7/2011 |

OTHER PUBLICATIONS

Berge, "Pharmaceutical Salts," Journal of Pharmaceutical Sciences, vol. 66, No. 1, Jan. 1977 (pp. 1-19).
Howell et al., "A growing role for mTOR in promoting anabolic metabolism," Biochemical Society Transactions, vol. 41, No. 4, No Month Listed 2013 (pp. 906-912).
International Search Report and Written Opinion issued by the United States Patent and Trademark Office as International Searching Authority for International Application No. PCT/US2016/050913, dated Jan. 10, 2017 (9 pages).
Kaeberlein, "mTOR Inhibition: From Aging to Autism and Beyond," Scientifica, vol. 2013, Oct. 2013 (17 pages).
Kim et al., "Nutrient regulation of the mTOR Complex 1 signaling pathway," Molecules and Cells, vol. 35, No. 6, Jun. 2013 (pp. 463-473).
LaPlante and Sabatini, "mTOR Signaling in Growth Control and Disease," Cell, vol. 149, No. 2, Apr. 2012 (pp. 274-293).
Liu et al., "Characterization of Torin2, an ATP-competitive inhibitor of mTOR, ATM, and ATR," Cancer Research, vol. 73, No. 8, Apr. 2013 (pp. 2574-2586).
Liu et al., "Kinome-wide Selectivity Profiling of ATP-competitive Mammalian Target of Rapamycin (mTOR) Inhibitors and Characterization of Their Binding Kinetics," Journal of Biological Chemistry, vol. 287, No. 13, Mar. 2012 (pp. 9742-9752).
Luengo et al., "Structure-activity studies of rapamycin analogs: evidence that the C-7 methoxy group is part of the effector domain and positioned at the FKBP12-FRAP interface," Chemistry and Biology, vol. 2, No. 7, Jul. 1995 (pp. 471-481).

* cited by examiner

*Primary Examiner* — Po-Chih Chen
(74) *Attorney, Agent, or Firm* — Andrea L. C. Reid; Dechert LLP

(57) ABSTRACT

The present invention provides compounds, compositions thereof, and methods of using the same.

14 Claims, No Drawings

RAPAMYCIN ANALOGS AND USES THEREOF

TECHNICAL FIELD OF THE INVENTION

The present invention relates to compounds and methods useful for modulating mTORC1 activity. The invention also provides pharmaceutically acceptable compositions comprising provided compounds of the present invention and methods of using such compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

The mechanistic target of rapamycin complex 1 (mTORC1) protein kinase is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell et al., (2013) Biochemical Society transactions 41, 906-912; Kim et al., (2013) Molecules and cells 35, 463-473; Laplante and Sabatini, (2012) Cell 149, 274-293). Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors mTORC1 inhibitors. Such compounds have the general formula I:

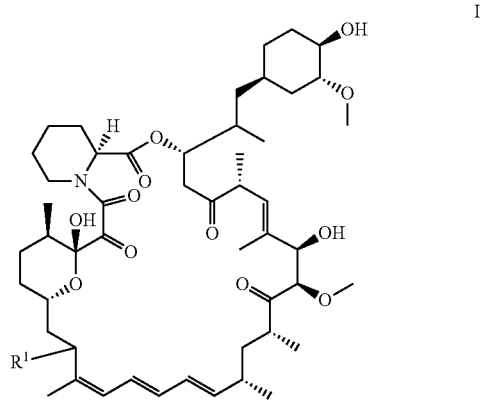

or a pharmaceutically acceptable salt thereof, wherein $R^1$ is as defined and described herein.

Compounds of the present invention, and pharmaceutically acceptable compositions thereof, are useful for treating a variety of diseases, disorders or conditions, associated with mTORC1. Such diseases, disorders, or conditions include those described herein.

DETAILED DESCRIPTION OF CERTAIN EMBODIMENTS

1. General Description of Certain Embodiments of the Invention

In certain embodiments, the present invention provides a compound of formula I:

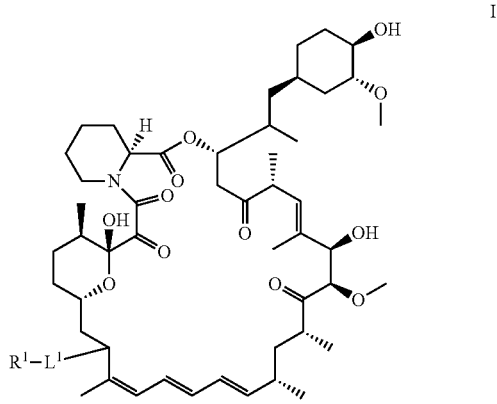

or a pharmaceutically acceptable salt thereof, wherein:
$L^1$ is a covalent bond or an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-; each R is independently hydrogen, or an optionally substituted group selected from C$_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each -Cy- is independently an optionally substituted bivalent ring selected from 3-7 membered saturated or partially unsaturated monocyclic or bicyclic carbocyclylene, monocyclic or bicyclic arylene, 4-10 membered saturated or partially unsaturated monocyclic or bicyclic heterocyclylene having 1-3 heteroatoms independently selected from nitrogen, oxygen, or sulfur, or 5-10 membered saturated or partially unsaturated monocyclic or bicyclic heteroarylene having 1-3 heteroatoms independently selected from nitrogen, oxygen, or sulfur; and $R^1$ is a monovalent derivative of an additional therapeutic agent.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^-$ (as in N-substituted pyrrolidinyl)).

The term "unsaturated," as used herein, means that a moiety has one or more units of unsaturation.

As used herein, the term "bivalent C$_{1-8}$ (or C$_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ{}_2$; $-N(R^\circ)C(S)NR^\circ{}_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ{}_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ{}_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ{}_2$; $-C(S)NR^\circ{}_2$; $-C(S)SR^\circ$; $-SC(S)SR^\circ$, $-(CH_2)_{0-4}OC(O)NR^\circ{}_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ{}_2$; $-(CH_2)_{0-4}S(O)R^\circ$; $-N(R^\circ)S(O)_2NR^\circ{}_2$; $-N(R^\circ)S(O)_2R^\circ$; $-N(OR^\circ)R^\circ$; $-C(NH)NR^\circ{}_2$; $-P(O)_2R^\circ$; $-P(O)R^\circ{}_2$; $-OP(O)R^\circ{}_2$; $-OP(O)(OR^\circ)_2$; $SiR^\circ{}_3$; $-(C_{1-4}$ straight or branched)alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet{}_2$, $-NO_2$, $-SiR^\bullet{}_3$, $-OSiR^\bullet{}_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*{}_2$, $=NNHC(O)R^*$, $=NNHC(O)OR^*$, $=NNHS(O)_2R^*$, $=NR^*$, $=NOR^*$, $-O(C(R^*{}_2))_{2-3}O-$, or $-S(C(R^*{}_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^●_2$, —C(NH)NR$^●_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(halon$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in mTORC1 activity between a sample comprising a compound of the present invention, or composition thereof, and mTORC1, and an equivalent sample comprising mTORC1 in the absence of said compound, or composition thereof.

3. Description of Exemplary Embodiments

As described above, in certain embodiments, the present invention provides a compound of formula I:

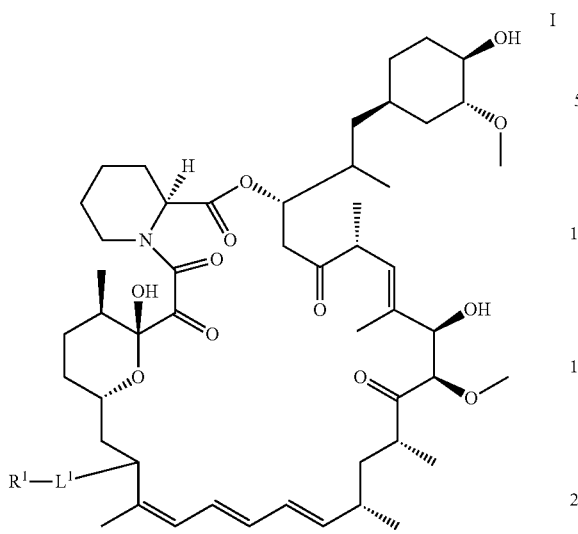

I

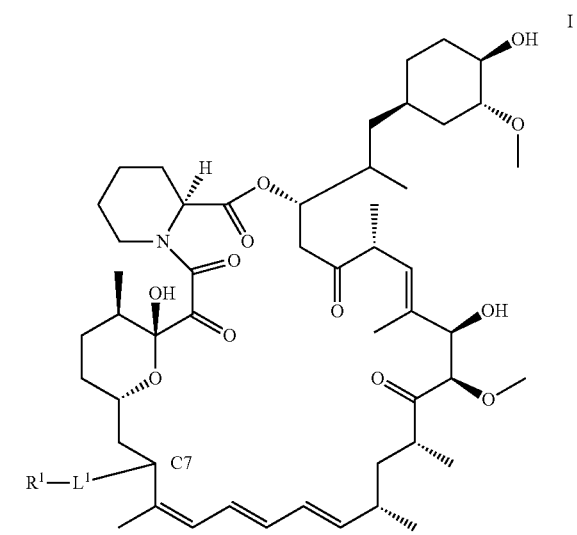

I or a pharmaceutically acceptable salt thereof, wherein:

$L^1$ is a covalent bond or an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$ N(R)—, —O—, —C(O)—, —OC(O)—, —C(O)O—, —S—, —S(O)—, —S(O)$_2$—, or -Cy-;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each -Cy- is independently an optionally substituted bivalent ring selected from 3-7 membered saturated or partially unsaturated monocyclic or bicyclic carbocyclylene, monocyclic or bicyclic arylene, 4-10 membered saturated or partially unsaturated monocyclic or bicyclic heterocyclylene having 1-3 heteroatoms independently selected from nitrogen, oxygen, or sulfur, or 5-10 membered saturated or partially unsaturated monocyclic or bicyclic heteroarylene having 1-3 heteroatoms independently selected from nitrogen, oxygen, or sulfur;

and $R^1$ is a monovalent derivative of an additional therapeutic agent.

One of ordinary skill in the art will appreciate that a provided compound of formula I is a hybrid molecule having a rapamycin portion covalently attached to an additional therapeutic agent, $R^1$, via the $L^1$ linker. Such covalent attachment of the additional therapeutic agent is achieved by nucleophilic addition of the therapeutic agent at the C7 position of rapamycin. For the purpose of clarity, provided formula I is reproduced below with the C7 position identified.

or a pharmaceutically acceptable salt thereof, wherein:

$L^1$ is a covalent bond or an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$ N(R)—, —O—, —C(O)—, —OC(O)—, —C(O)O—, —S—, —S(O)—, —S(O)$_2$—, or -Cy-;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each -Cy- is independently an optionally substituted bivalent ring selected from 3-7 membered saturated or partially unsaturated monocyclic or bicyclic carbocyclylene, monocyclic or bicyclic arylene, 4-10 membered saturated or partially unsaturated monocyclic or bicyclic heterocyclylene having 1-3 heteroatoms independently selected from nitrogen, oxygen, or sulfur, or 5-10 membered saturated or partially unsaturated monocyclic or bicyclic heteroarylene having 1-3 heteroatoms independently selected from nitrogen, oxygen, or sulfur;

and $R^1$ is a monovalent derivative of an additional therapeutic agent.

In some embodiments, the present invention provides a compound of formula I-a or I-b:

I-a

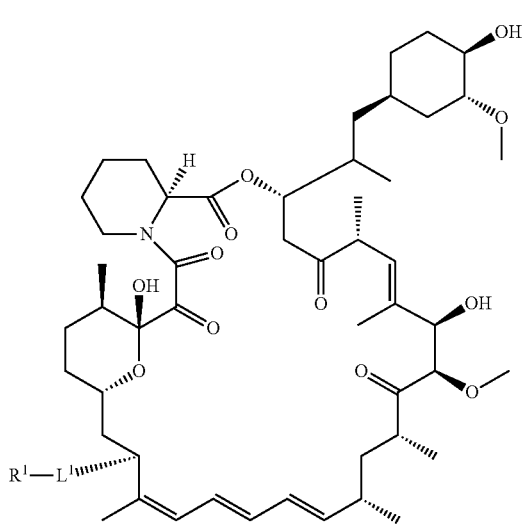

I-b

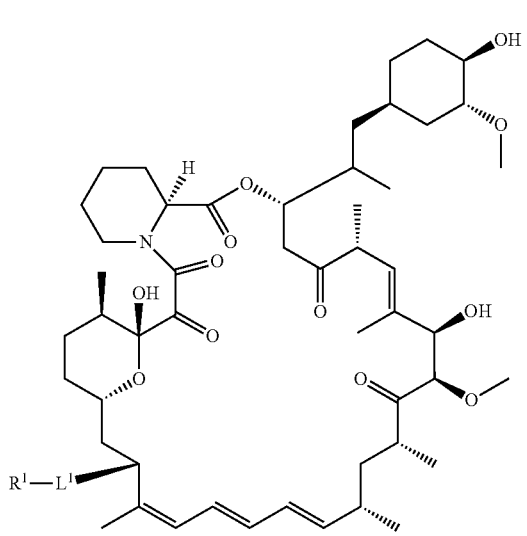

or a pharmaceutically acceptable salt thereof, wherein each of $R^1$ and $L^1$ is as defined above and described herein in classes and subclasses, both singly and in combination.

It will be appreciated that the term "rapamycin", and structure thereof, recited through the specification is intended to encompass rapamycin and analogs thereof. Accordingly, in some embodiments, the present invention provides a compound of formula II:

II

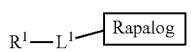

or a pharmaceutically acceptable salt thereof, wherein:

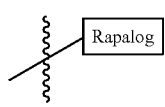

is a monovalent derivative of rapamycin, or analog thereof, wherein $R^1$-$L^1$- is attached thereto at the C7 position of the rapamycin, or analog thereof;

$L^1$ is a covalent bond or an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur;

each -Cy- is independently an optionally substituted bivalent ring selected from 3-7 membered saturated or partially unsaturated monocyclic or bicyclic carbocyclylene, monocyclic or bicyclic arylene, 4-10 membered saturated or partially unsaturated monocyclic or bicyclic heterocyclylene having 1-3 heteroatoms independently selected from nitrogen, oxygen, or sulfur, or 5-10 membered saturated or partially unsaturated monocyclic or bicyclic heteroarylene having 1-3 heteroatoms independently selected from nitrogen, oxygen, or sulfur;

and $R^1$ is a monovalent derivative of an additional therapeutic agent.

In some embodiments, the present invention provides a compound of formula II-a or II-b:

II-a

II-b

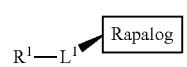

or a pharmaceutically acceptable salt thereof, wherein each of

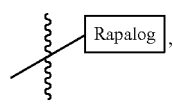

$R^1$, and $L^1$ is as defined above and described herein in classes and subclasses, both singly and in combination.

In some embodiments,

is rapamycin. In other embodiments,

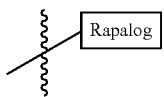

is Temsirolimus. In certain embodiments,

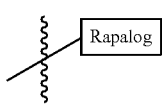

is Everolimus. In certain embodiments,

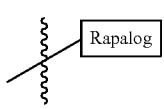

is Deforolimus. One of ordinary skill in the art will appreciate that additional rapamycin analogs are also encompassed by provided compounds.

As defined above, $L^1$ is a covalent bond or an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-. In some embodiments, $L^1$ is a covalent bond. In other embodiments, $L^1$ is an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy.

In some embodiments, $L^1$ is a bivalent optionally substituted straight or branched $C_{1-20}$ alkylene chain. In some embodiments, $L^1$ is a bivalent optionally substituted straight or branched $C_{1-20}$ alkylene chain wherein one methylene unit of the chain is replaced by —O—. In some embodiments, $L^1$ is selected from those depicted in Table 1, below.

Rapamycin is marketed under the brand name Rapamune® (generic name, sirolimus) and is well known for its antiproliferative and immunosuppressive activity. Rapamycin is FDA approved for the prevention of transplant rejection and for coating stents to prevent restenosis. Aside from the documented benefits of rapamycin, it is well known that rapamycin is associated with a number of serious side effects. Such side effects include diabetes-like symptoms of decreased glucose tolerance and lowering of insulin sensitivity. In addition, it has been reported that rapamycin activates the Akt signaling pathway (including activation of Akt and ERK) thereby increasing a patient's risk of cancer.

Without wishing to be bound by any particular theory, it is believed that a provided molecule of formula I or formula II affords a "hybrid" therapeutic agent thereby imparting particularly beneficial attributes to both the rapamycin portion and the additional therapeutic agent bound thereto (i.e., $R^1$).

In some embodiments, a provided compound of formula I or formula II is more efficatious than rapamycin alone. In some embodiments, the present invention provides a compound of formula I or formula II wherein the rapamycin portion and the additional therapeutic agent result in a synergistic effect.

In some embodiments, $R^1$ is a monovalent inhibitor of mTORC1 and/or mTORC2 kinase. In some embodiments, the monovalent inhibitor of mTORC1 and/or mTORC2 is AZD8055, AZD2014, OSI-027, MLN0128, WYE-132, Torin1, PI-103, P7170, PF-04691502, PF-05212384, PKI-857, GNE-477, PKI-179, WJD008, XL765, SAR245409, NVP-BEZ235, BGT226, SF1126, or GSK2126458.

In some embodiments, $R^1$ is an inhibitor of 4E-BP1 and/or ULK1. In some embodiments, $R^1$ is an inhibitor of an additional protein kinase. In some embodiments, the additional protein kinase is Akt, CDK4, CDK6, EGFR, HER2, and/or AMPK. In some embodiments, $R^1$ is an inhibitor of CDK4 or CDK6. In some embodiments, $R^1$ is a dual inhibitor CDK4 and CDK6. In some embodiments, $R^1$ is monovalent palbociclib. In some embodiments, $R^1$ is an EGFR inhibitor, a HER2 inhibitor, or a dual EGFR/HER2 inhibitor. In some embodiments, $R^1$ is monovalent lapatinib. In some embodiments, $R^1$ is an inhibitor of BCR-Abl. In certain embodiments, $R^1$ is monovalent Imatinib or Dasatinib. In some embodiments, $R^1$ is a BCL-2 inhibitor. In certain embodiments, $R^1$ is monovalent ABT-199.

In some embodiments, a provided compound of formula I or formula II, when administered to a patient, results in fewer and/or lesser severity of side effects than when rapamycin is administered. In some embodiments, $R^1$ is a monovalent therapeutic agent that is capable of mitigating one or more side effects of rapamycin. In some embodiments, $R^1$ is monovalent metformin and the resulting compound of formula I or formula II mitigates glucose intolerance and/or hyperlipidemia. In some embodiments, $R^1$ is a PPAR modulator (e.g., Rosiglitazone or Pioglitazone) and the resulting compound of formula I or formula II glucose intolerance and/or hyperlipidemia. In some embodiments, $R^1$ is a DPP4 inhibitor (e.g., Sitagliptin or Vidaglptin) and the resulting compound of formula I or formula II glucose intolerance and/or hyperlipidemia.

One of ordinary skill in the art will recognize that numerous therapeutic agents are suitable for nucleophilic addition to the C7 position of rapamycin to provide a compound of formula I or formula II.

In some embodiments, $R^1$ is selected from:
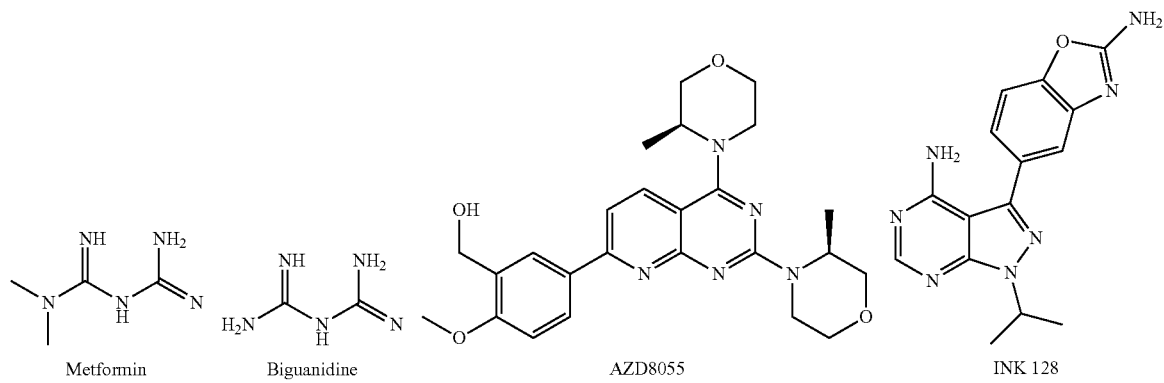
Metformin, Biguanidine, AZD8055, INK 128
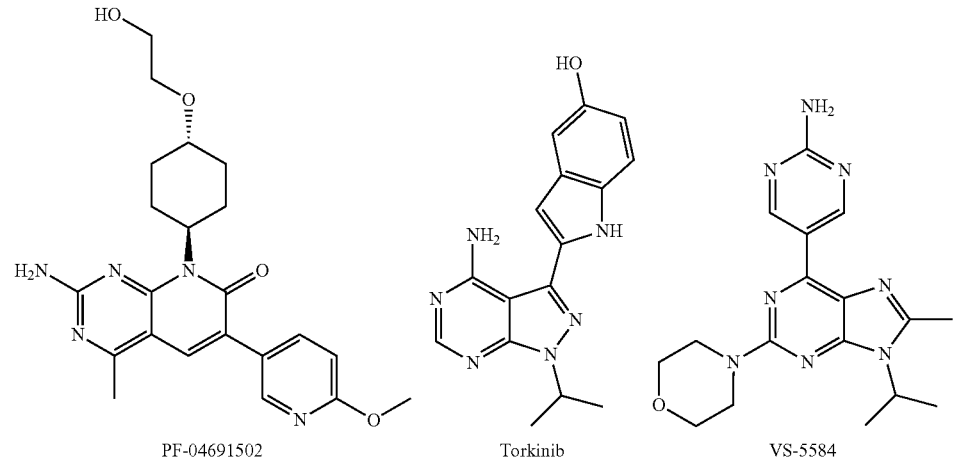
PF-04691502, Torkinib, VS-5584
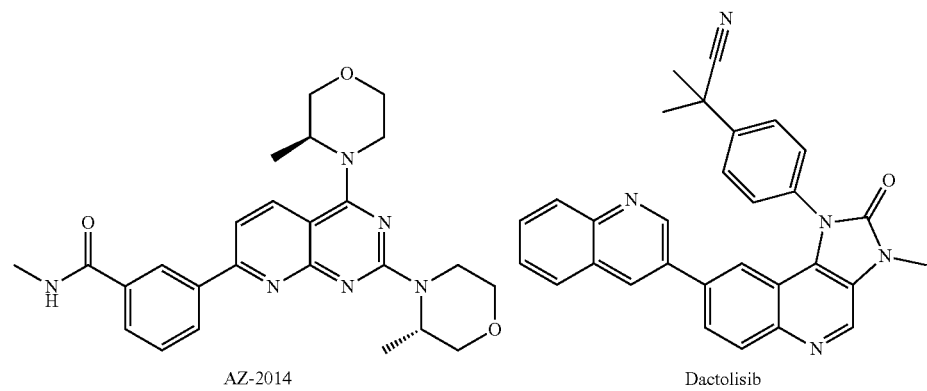
AZ-2014, Dactolisib
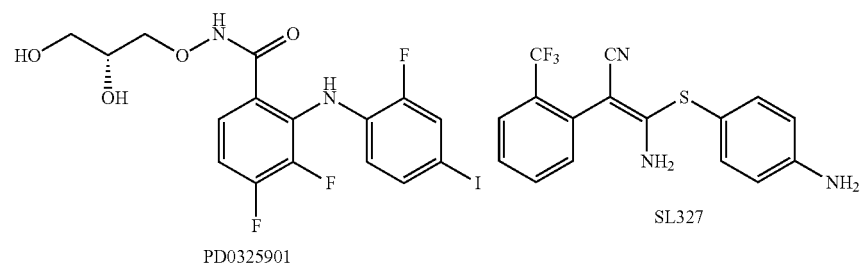
PD0325901, SL327

-continued
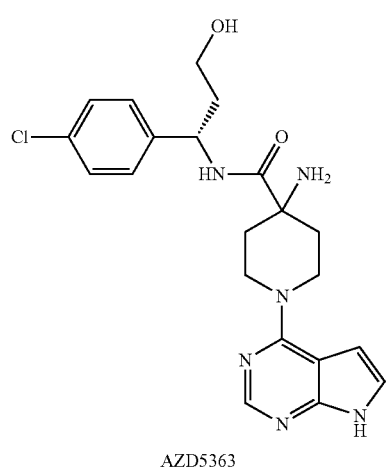
AZD5363
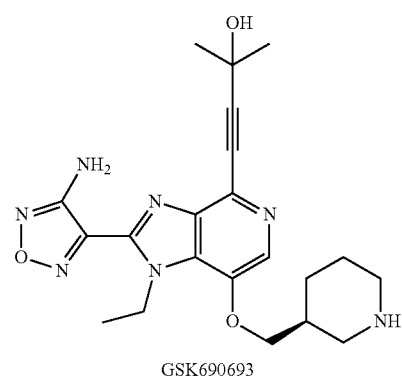
GSK690693
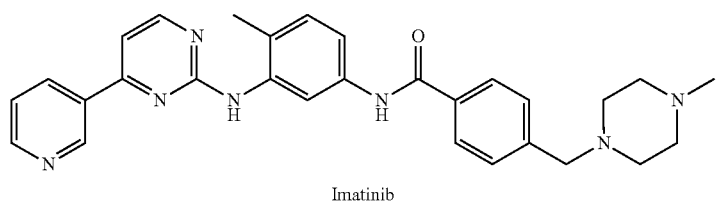
Imatinib
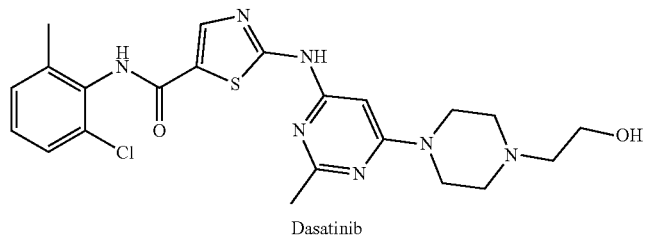
Dasatinib
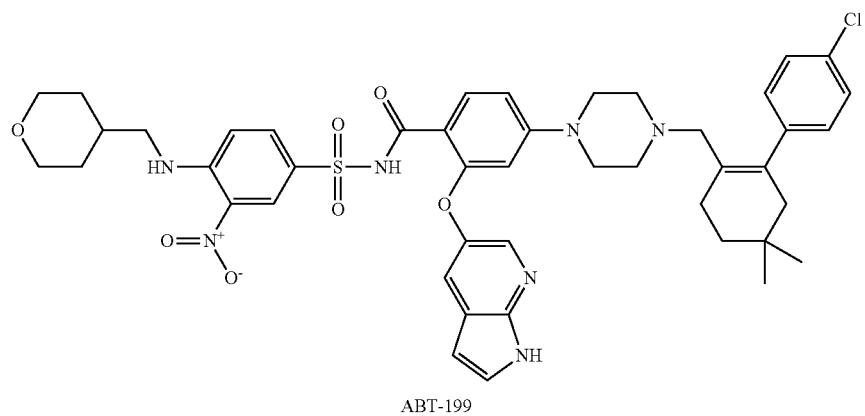
ABT-199
Exemplary compounds of the invention are set forth in Table 1, below.

TABLE 1
Exemplary Compounds
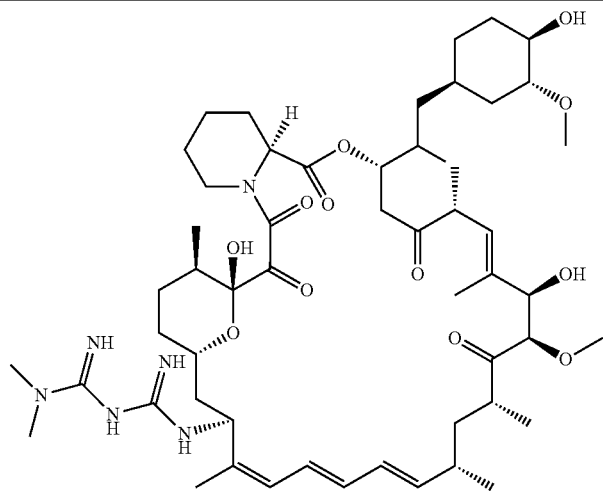
I-1
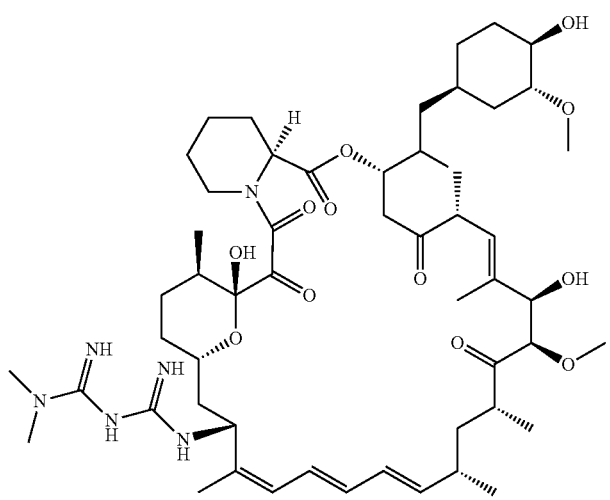
I-2
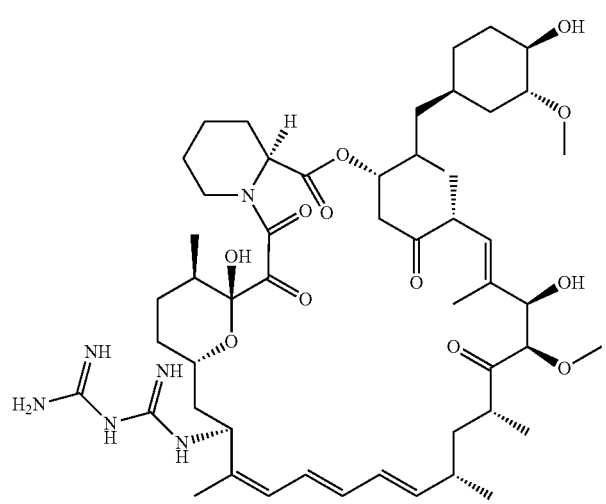 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](NC(=N)NC(=N)N)C[C@@H]3CC[C@@H](C)[C@@](O)(O3)C(=O)C(=O)N3CCCC[C@H]3C(=O)O2)CC[C@H]1O]
I-3

TABLE 1-continued
Exemplary Compounds
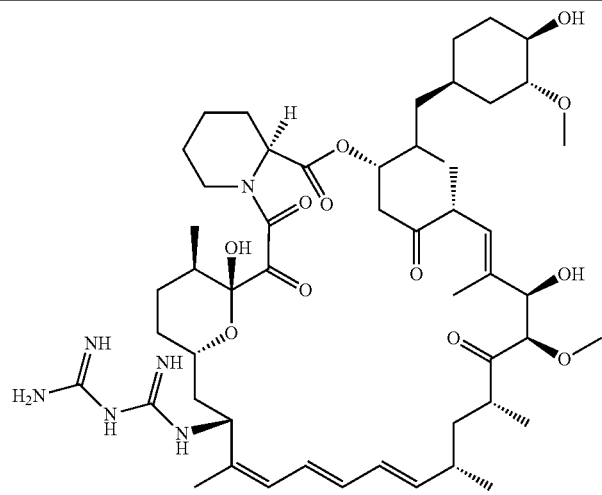
I-4
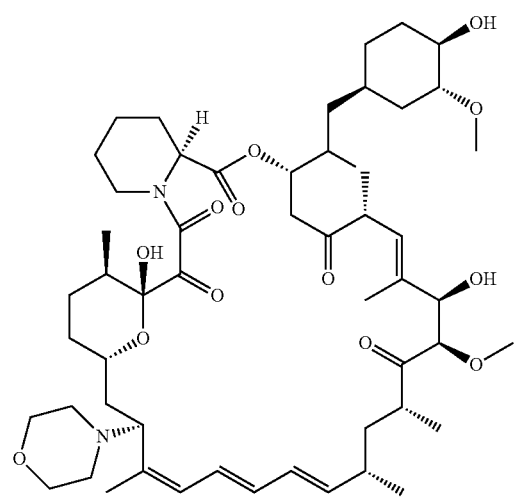 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](N3CCOCC3)C[C@@H]3CC[C@@H](C)[C@@](O)(O3)C(=O)C(=O)N3CCCC[C@H]3C(=O)O2)CC[C@H]1O]
I-5
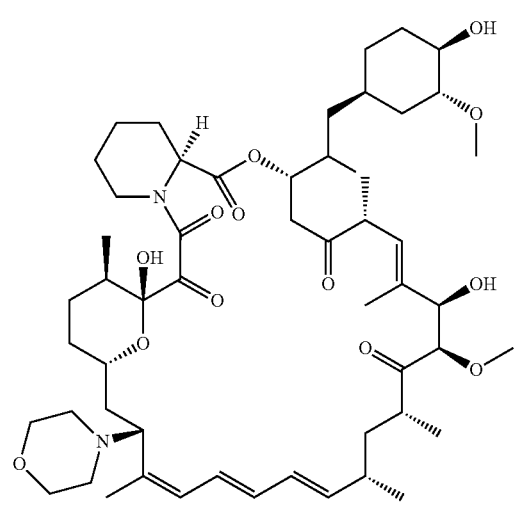 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](N3CCOCC3)C[C@@H]3CC[C@@H](C)[C@@](O)(O3)C(=O)C(=O)N3CCCC[C@H]3C(=O)O2)CC[C@H]1O]
I-6

TABLE 1-continued
Exemplary Compounds
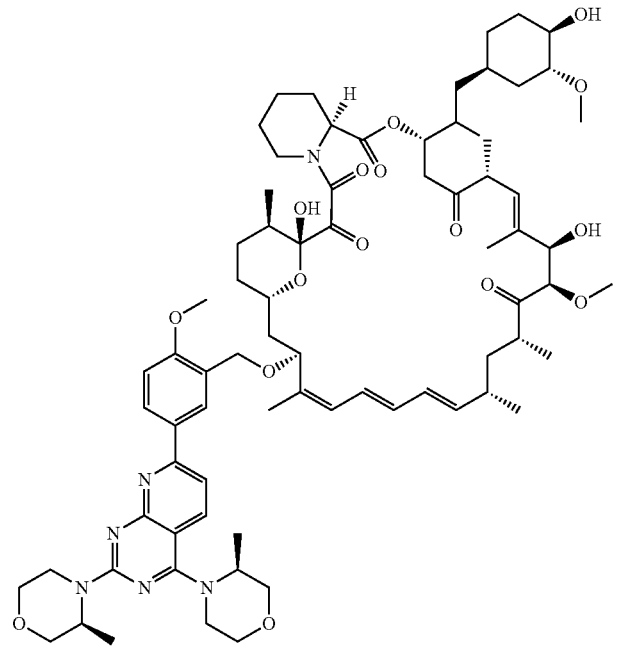 [SMILES: COc1ccc(-c2ccc3c(N4CCOC[C@@H]4C)nc(N4CCOC[C@@H]4C)nc3n2)cc1CO[C@H]1C[C@@H]2CC[C@@H](C)[C@@](O)(O2)C(=O)C(=O)N2CCCC[C@H]2C(=O)O[C@H](C(C)C[C@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C\1C]
I-7
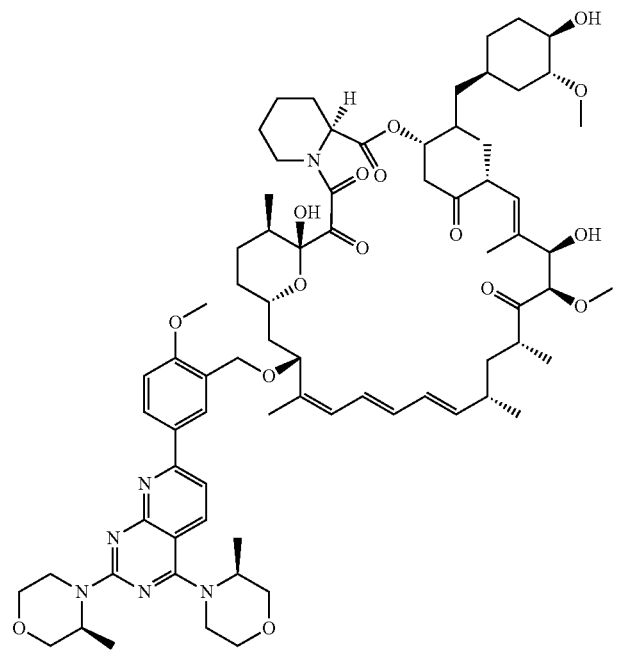
I-8

TABLE 1-continued
Exemplary Compounds
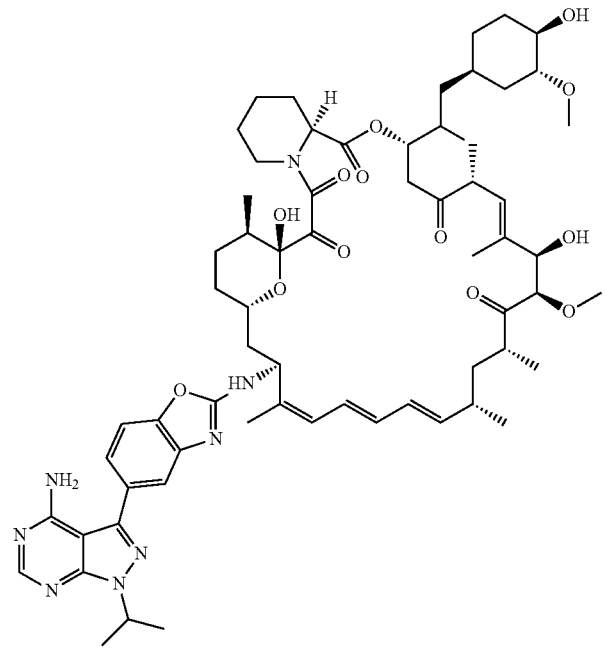 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](Nc3nc4cc(-c5nn(C(C)C)c6ncnc(N)c56)ccc4o3)C[C@@H]3CC[C@@H](C)[C@@](O)(O3)C(=O)C(=O)N3CCCC[C@H]3C(=O)O2)CC[C@H]1O]
I-9
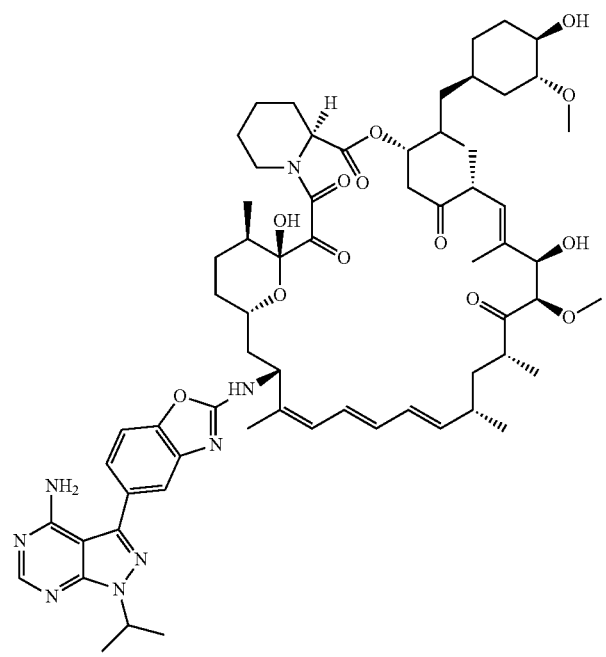 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](Nc3nc4cc(-c5nn(C(C)C)c6ncnc(N)c56)ccc4o3)C[C@@H]3CC[C@@H](C)[C@@](O)(O3)C(=O)C(=O)N3CCCC[C@H]3C(=O)O2)CC[C@H]1O]
I-10

TABLE 1-continued
Exemplary Compounds
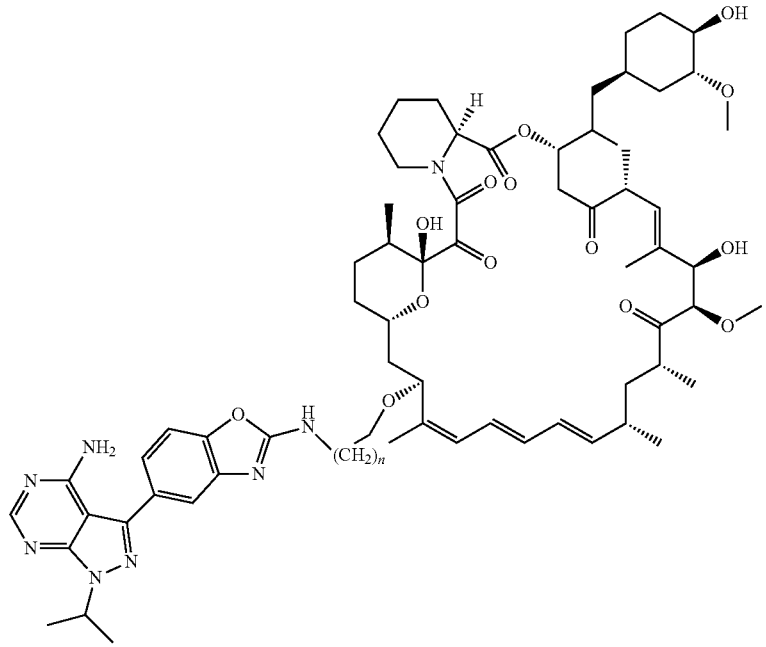
n = 1, 2
I-11
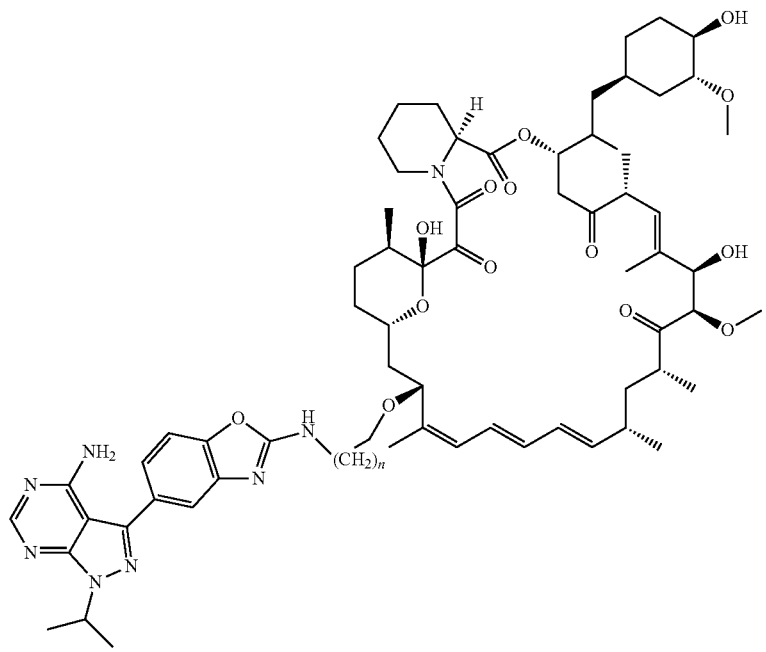
n = 1, 2
I-12

TABLE 1-continued
Exemplary Compounds
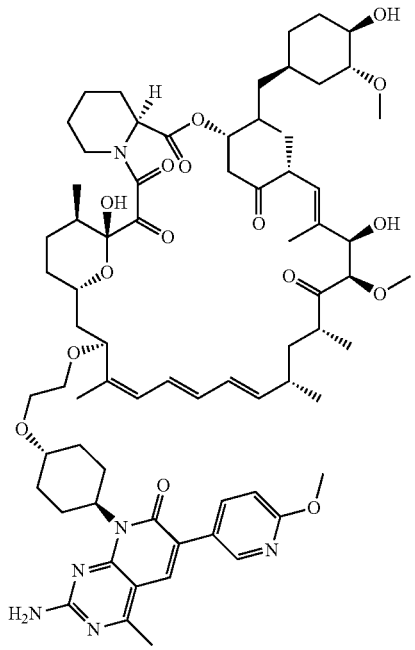 [SMILES: COc1ccc(-c2cc3c(C)nc(N)nc3n([C@H]3CC[C@H](OCCO[C@H]4C[C@@H]5CC[C@@H](C)[C@@](O)(O5)C(=O)C(=O)N5CCCC[C@H]5C(=O)O[C@H](C(C)C[C@H]5CC[C@@H](O)[C@H](OC)C5)CC(=O)[C@H](C)/C=C(\C)[C@@H](O)[C@@H](OC)C(=O)[C@H](C)C[C@H](C)/C=C/C=C/C=C\4C)CC3)c2=O)cn1]
I-13
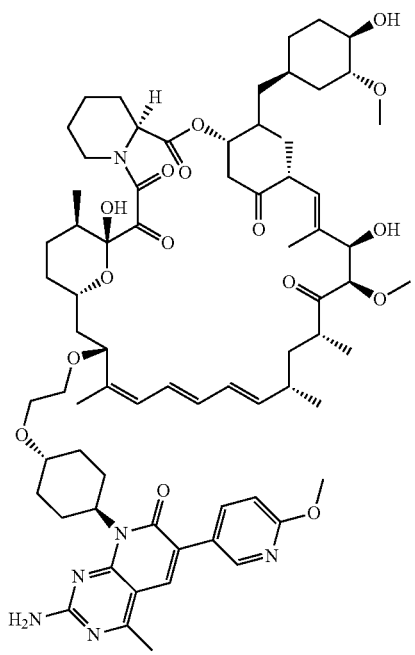 [SMILES: COc1ccc(-c2cc3c(C)nc(N)nc3n([C@H]3CC[C@H](OCCO[C@@H]4C[C@@H]5CC[C@@H](C)[C@@](O)(O5)C(=O)C(=O)N5CCCC[C@H]5C(=O)O[C@H](C(C)C[C@H]5CC[C@@H](O)[C@H](OC)C5)CC(=O)[C@H](C)/C=C(\C)[C@@H](O)[C@@H](OC)C(=O)[C@H](C)C[C@H](C)/C=C/C=C/C=C\4C)CC3)c2=O)cn1]
I-14

TABLE 1-continued
Exemplary Compounds
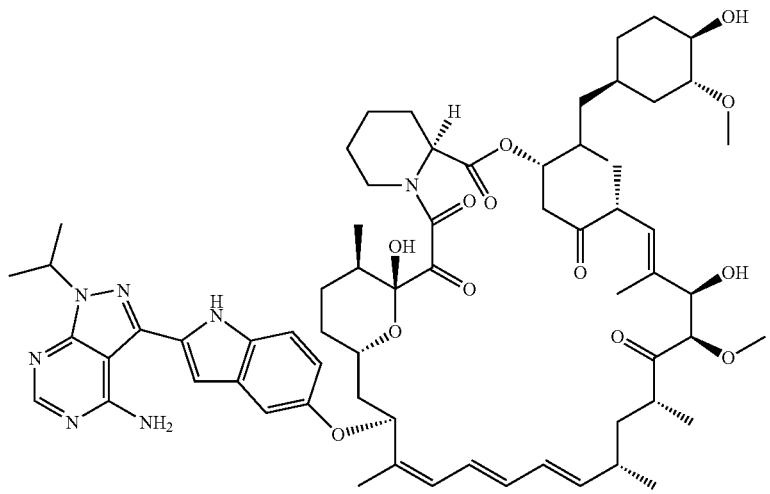 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](Oc3ccc4[nH]c(-c5nn(C(C)C)c6ncnc(N)c56)cc4c3)C[C@@H]3CC[C@@H](C)[C@@](O)(O3)C(=O)C(=O)N3CCCC[C@H]3C(=O)O2)CC[C@H]1O]
I-15
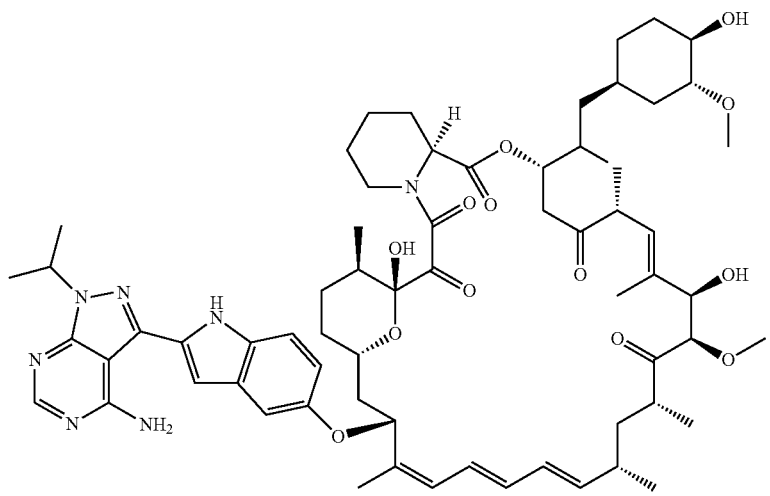 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](Oc3ccc4[nH]c(-c5nn(C(C)C)c6ncnc(N)c56)cc4c3)C[C@@H]3CC[C@@H](C)[C@@](O)(O3)C(=O)C(=O)N3CCCC[C@H]3C(=O)O2)CC[C@H]1O]
I-16
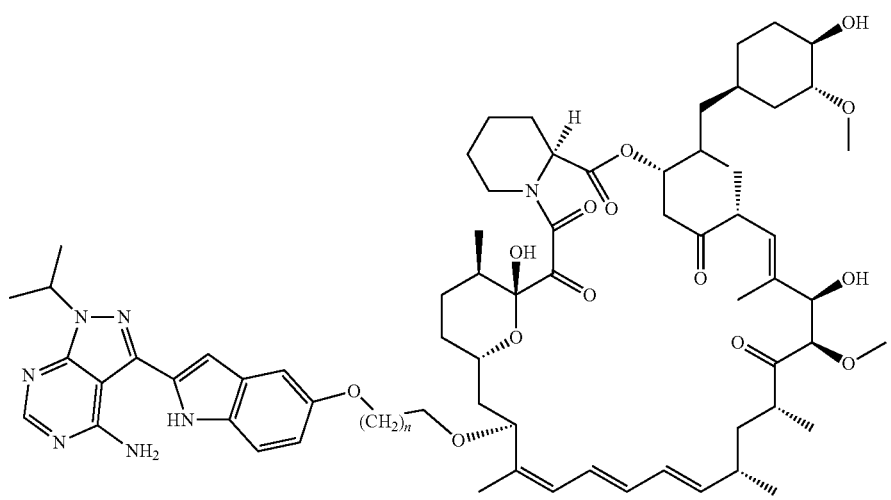
n = 1, 2

TABLE 1-continued
Exemplary Compounds
I-17
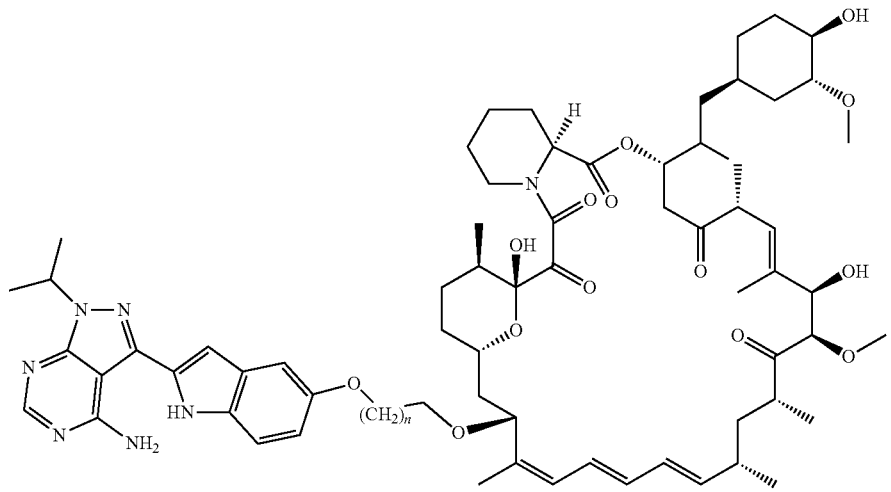
n = 1, 2
I-18
I-19
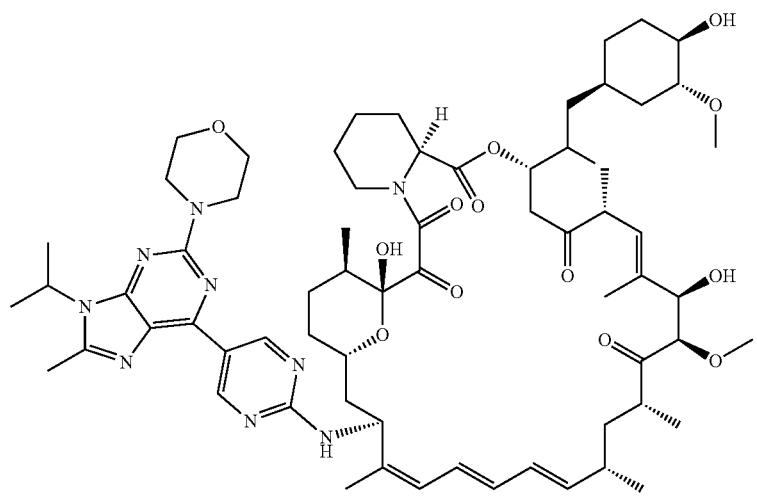 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](Nc3ncc(-c4nc(N5CCOCC5)nc5c4nc(C)n5C(C)C)cn3)C[C@@H]3CC[C@@H](C)[C@@](O)(O3)C(=O)C(=O)N3CCCC[C@H]3C(=O)O2)CC[C@H]1O]

TABLE 1-continued
Exemplary Compounds
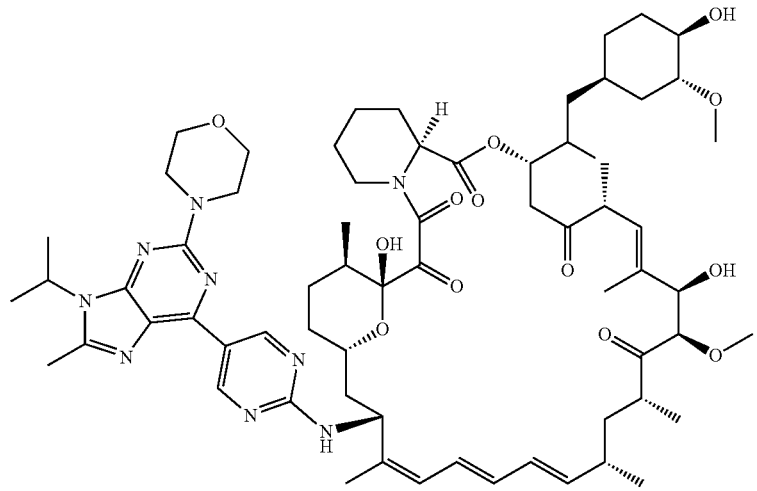 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](Nc3ncc(-c4nc(N5CCOCC5)nc5c4nc(C)n5C(C)C)cn3)C[C@@H]3CC[C@@H](C)[C@@](O)(O3)C(=O)C(=O)N3CCCC[C@H]3C(=O)O2)CC[C@H]1O]
I-20
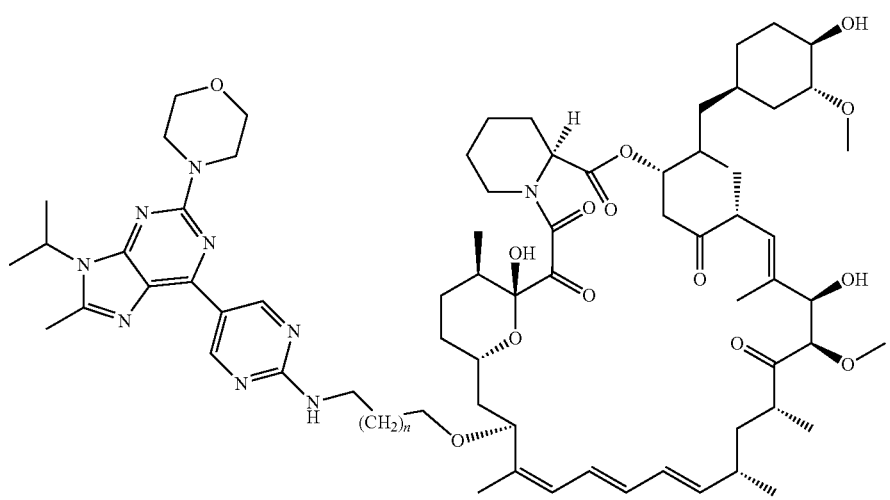
n = 1, 2
I-21

TABLE 1-continued
Exemplary Compounds
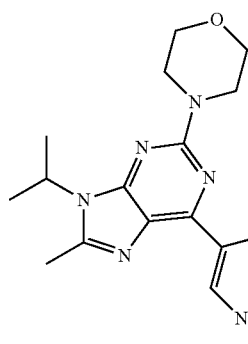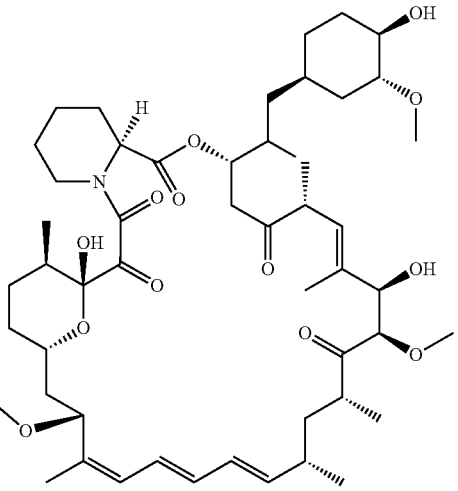
n = 1, 2
I-22
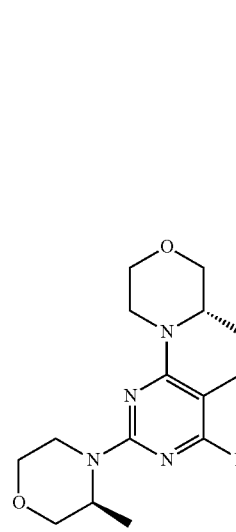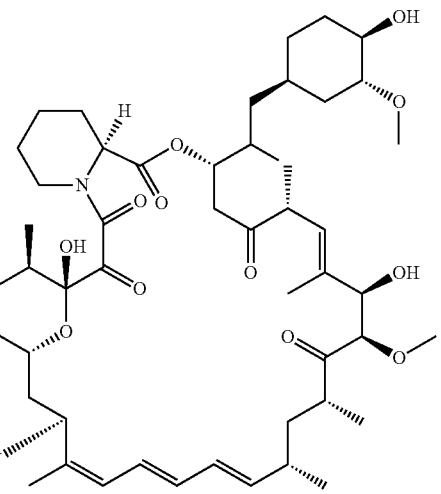
I-23

TABLE 1-continued
Exemplary Compounds
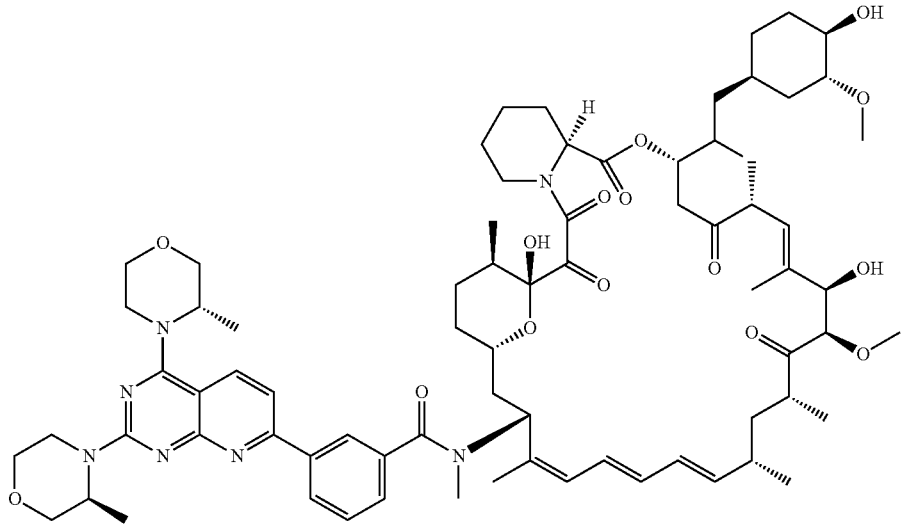 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](N(C)C(=O)c3cccc(-c4ccc5c(N6CCOC[C@@H]6C)nc(N6CCOC[C@@H]6C)nc5n4)c3)C[C@@H]3CC[C@@H](C)[C@@](O)(O3)C(=O)C(=O)N3CCCC[C@H]3C(=O)O2)CC[C@H]1O]
I-24
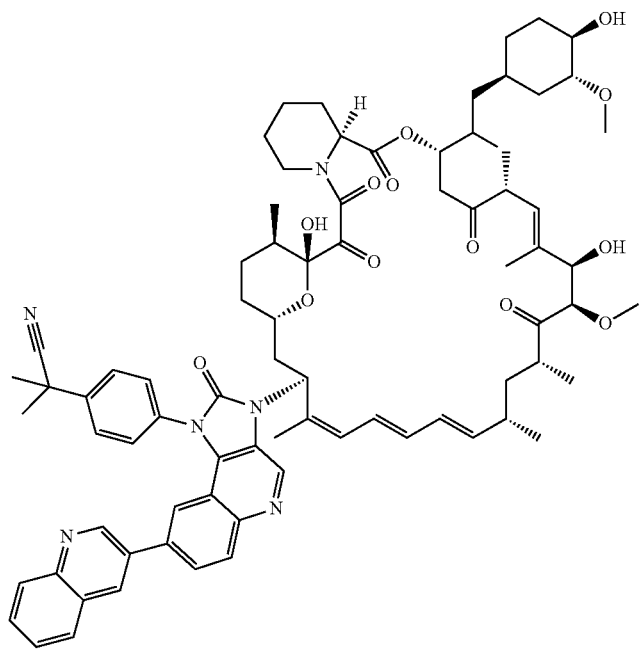 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](n3c(=O)n(-c4ccc(C(C)(C)C#N)cc4)c4c5cc(-c6cnc7ccccc7c6)ccc5ncc43)C[C@@H]3CC[C@@H](C)[C@@](O)(O3)C(=O)C(=O)N3CCCC[C@H]3C(=O)O2)CC[C@H]1O]
I-25

TABLE 1-continued
Exemplary Compounds
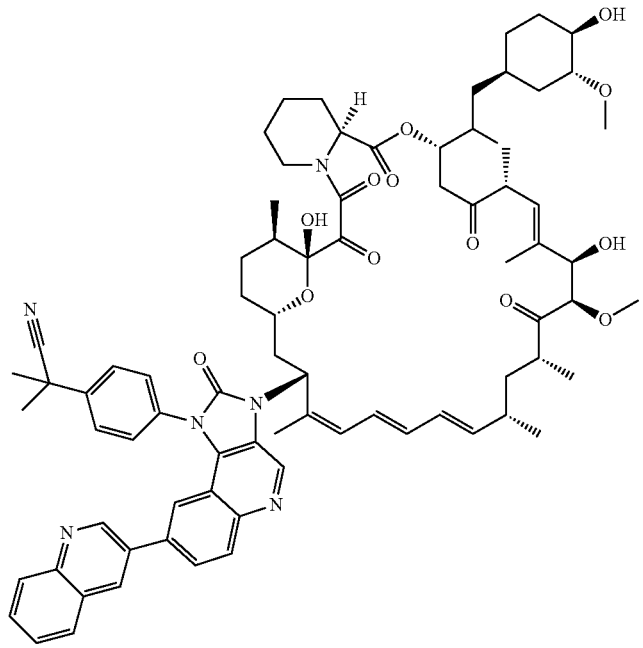 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](n3c(=O)n(-c4ccc(C(C)(C)C#N)cc4)c4c5cc(-c6cnc7ccccc7c6)ccc5ncc43)C[C@@H]3CC[C@@H](C)[C@@](O)(O3)C(=O)C(=O)N3CCCC[C@H]3C(=O)O2)CC[C@H]1O]
I-26
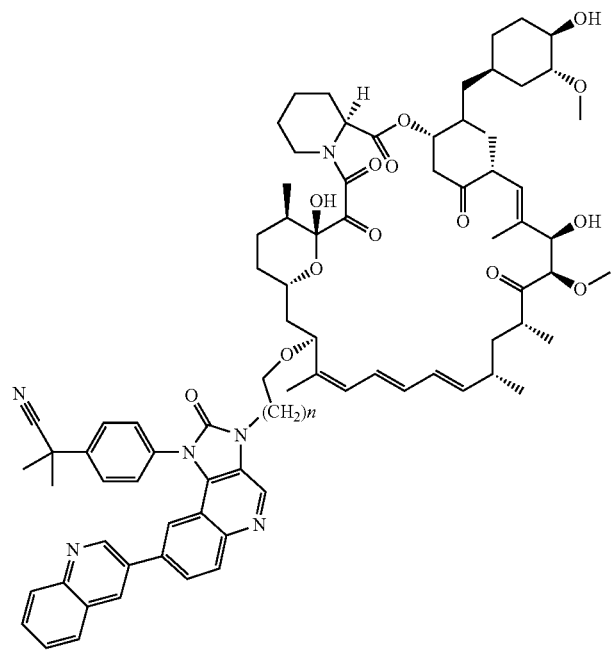
n = 1, 2
I-27

TABLE 1-continued
Exemplary Compounds
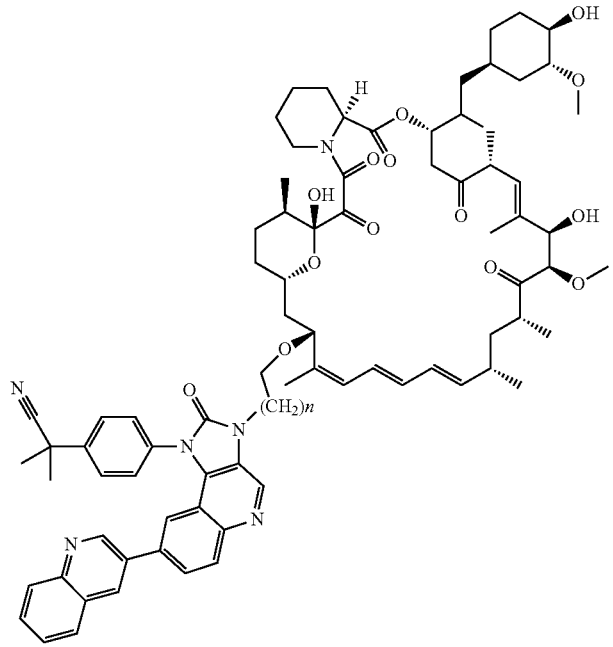
n = 1, 2
I-28
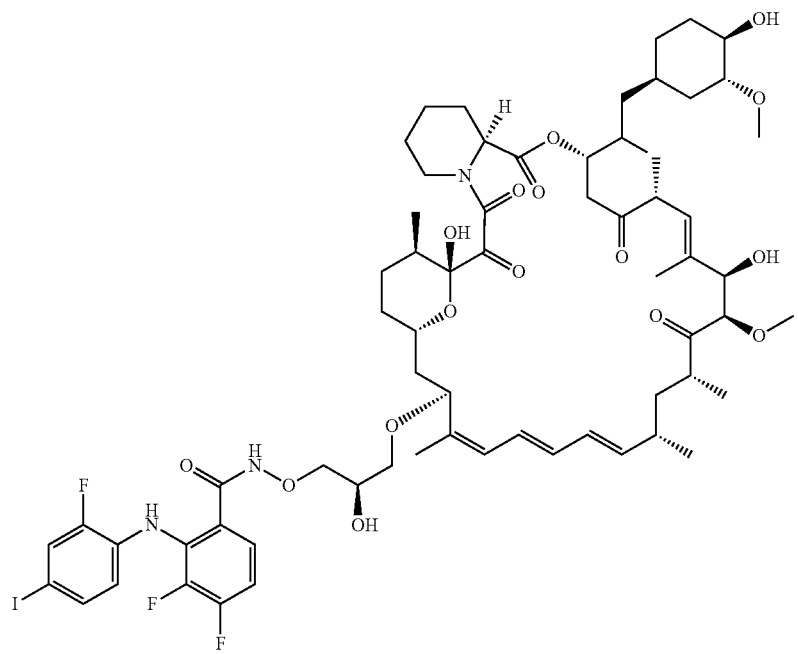 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](OC[C@@H](O)CONC(=O)c3ccc(F)c(F)c3Nc3ccc(I)cc3F)C[C@@H]3CC[C@@H](C)[C@@](O)(O3)C(=O)C(=O)N3CCCC[C@H]3C(=O)O2)CC[C@H]1O]
I-29

TABLE 1-continued
Exemplary Compounds
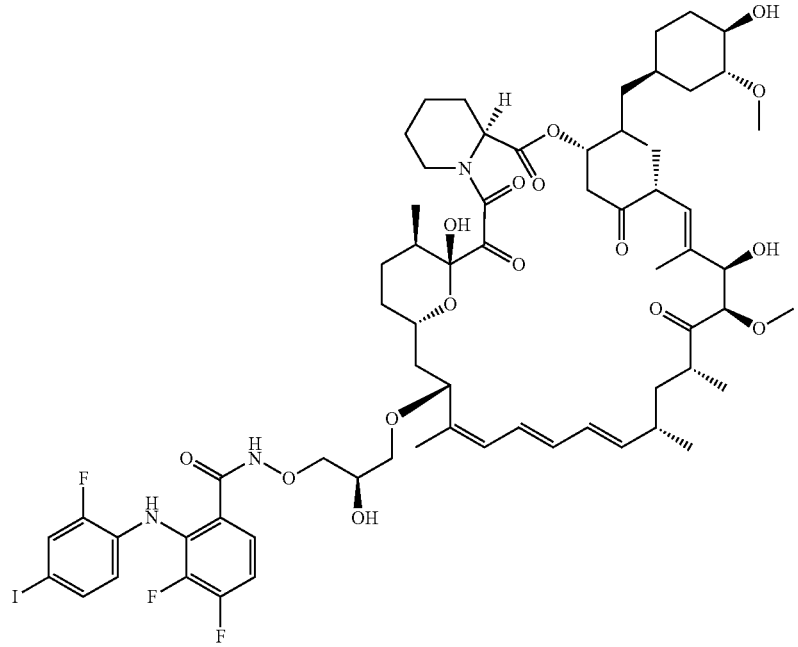 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](OC[C@@H](O)CONC(=O)c3ccc(F)c(F)c3Nc3ccc(I)cc3F)C[C@@H]3CC[C@@H](C)[C@@](O)(O3)C(=O)C(=O)N3CCCC[C@H]3C(=O)O2)CC[C@H]1O]
I-30
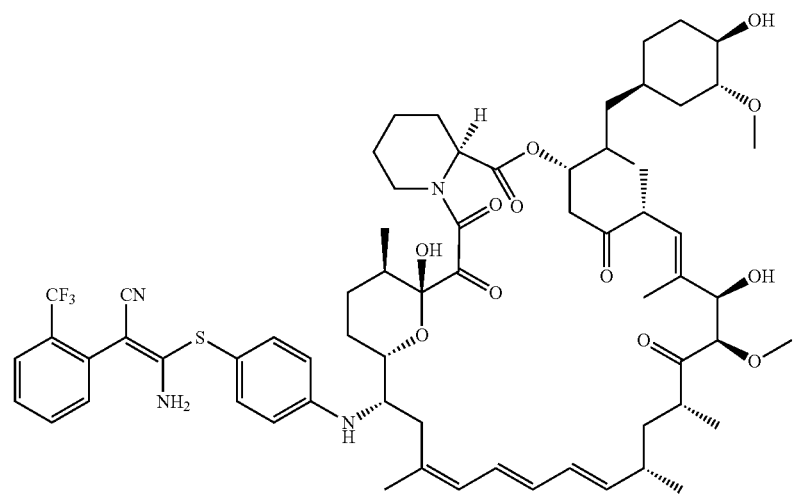 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)C[C@H](Nc3ccc(S/C(N)=C(\C#N)c4ccccc4C(F)(F)F)cc3)[C@@H]3CC[C@@H](C)[C@@](O)(O3)C(=O)C(=O)N3CCCC[C@H]3C(=O)O2)CC[C@H]1O]
I-31

TABLE 1-continued
Exemplary Compounds
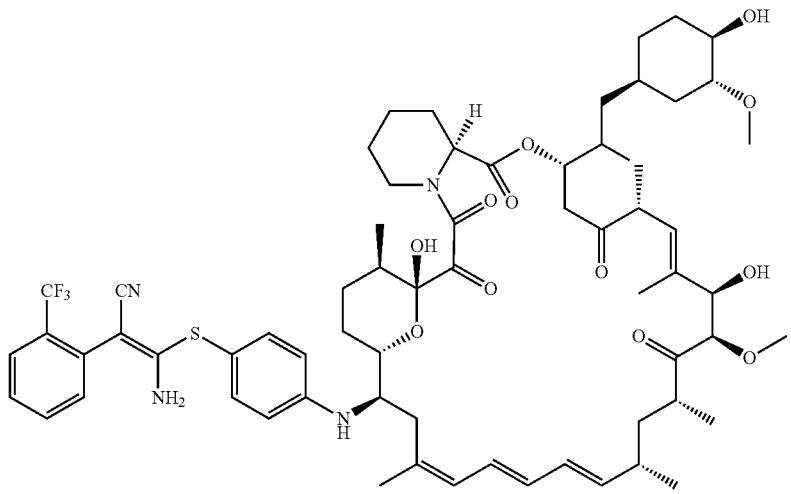 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)C[C@@H](Nc3ccc(S/C(N)=C(\C#N)c4ccccc4C(F)(F)F)cc3)[C@@H]3CC[C@@H](C)[C@@](O)(O3)C(=O)C(=O)N3CCCC[C@H]3C(=O)O2)CC[C@H]1O]
I-32
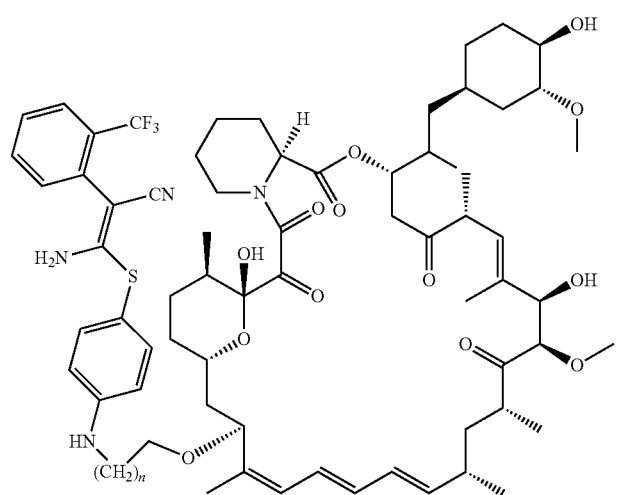
I-33
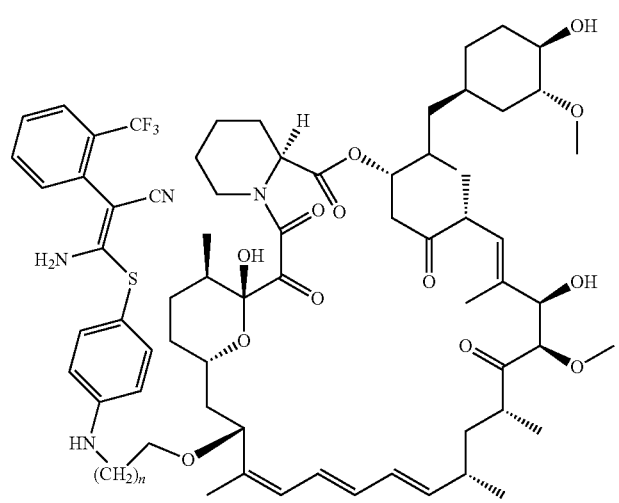
I-34

TABLE 1-continued
Exemplary Compounds
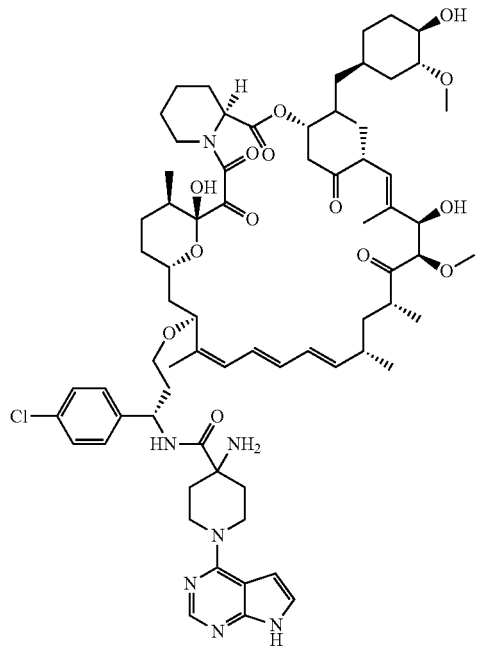 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](OCC[C@H](NC(=O)C3(N)CCN(c4ncnc5[nH]ccc45)CC3)c3ccc(Cl)cc3)C[C@@H]3CC[C@@H](C)[C@@](O)(O3)C(=O)C(=O)N3CCCC[C@H]3C(=O)O2)CC[C@H]1O]
I-35
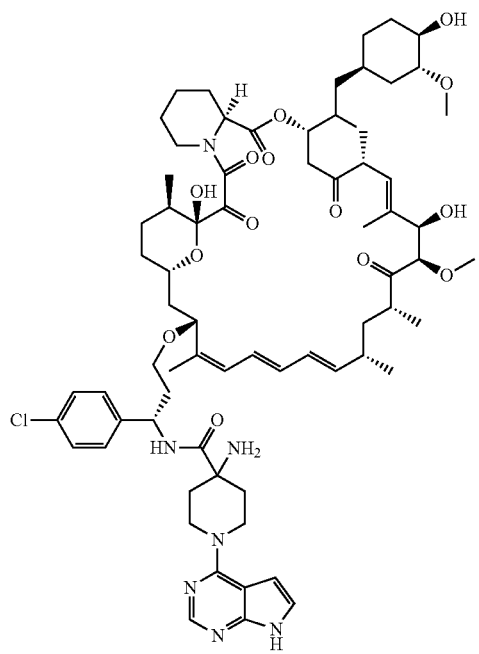 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](OCC[C@H](NC(=O)C3(N)CCN(c4ncnc5[nH]ccc45)CC3)c3ccc(Cl)cc3)C[C@@H]3CC[C@@H](C)[C@@](O)(O3)C(=O)C(=O)N3CCCC[C@H]3C(=O)O2)CC[C@H]1O]
I-36

TABLE 1-continued
Exemplary Compounds
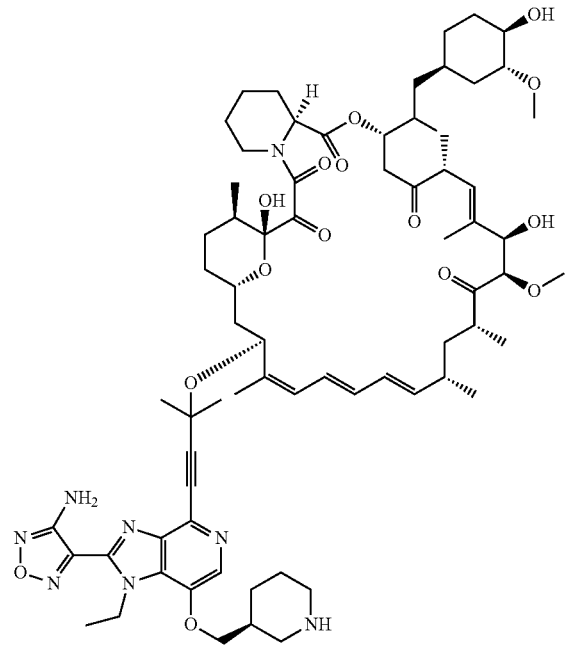 [SMILES: CCn1c(-c2nonc2N)nc2c(C#CC(C)(C)O[C@H]3C[C@@H]4CC[C@@H](C)[C@@](O)(O4)C(=O)C(=O)N4CCCC[C@H]4C(=O)O[C@H](C(C)C[C@H]4CC[C@@H](O)[C@H](OC)C4)CC(=O)[C@H](C)/C=C(\C)[C@@H](O)[C@@H](OC)C(=O)[C@H](C)C[C@H](C)/C=C/C=C/C=C\3C)ncc(OC[C@H]3CCCNC3)c21]
I-37
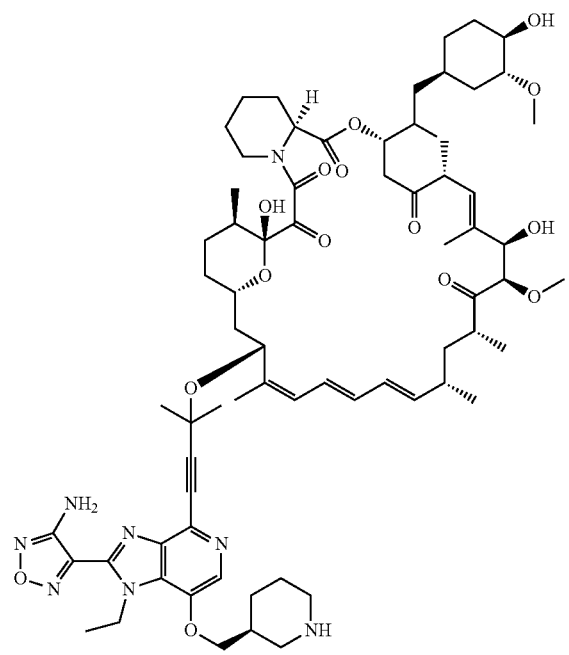 [SMILES: CCn1c(-c2nonc2N)nc2c(C#CC(C)(C)O[C@@H]3C[C@@H]4CC[C@@H](C)[C@@](O)(O4)C(=O)C(=O)N4CCCC[C@H]4C(=O)O[C@H](C(C)C[C@H]4CC[C@@H](O)[C@H](OC)C4)CC(=O)[C@H](C)/C=C(\C)[C@@H](O)[C@@H](OC)C(=O)[C@H](C)C[C@H](C)/C=C/C=C/C=C\3C)ncc(OC[C@H]3CCCNC3)c21]
I-38

TABLE 1-continued
Exemplary Compounds
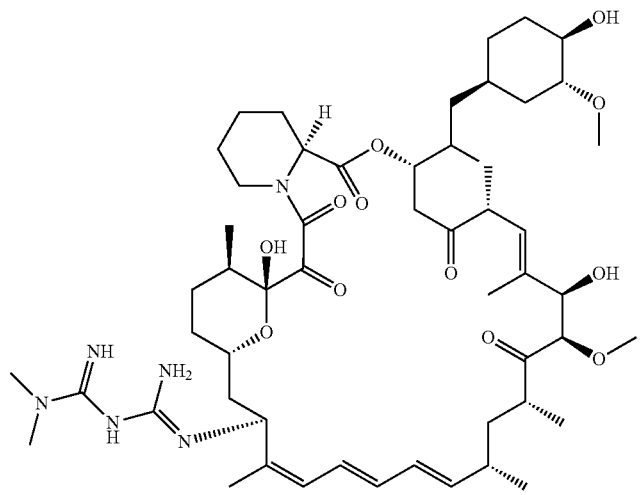
I-39
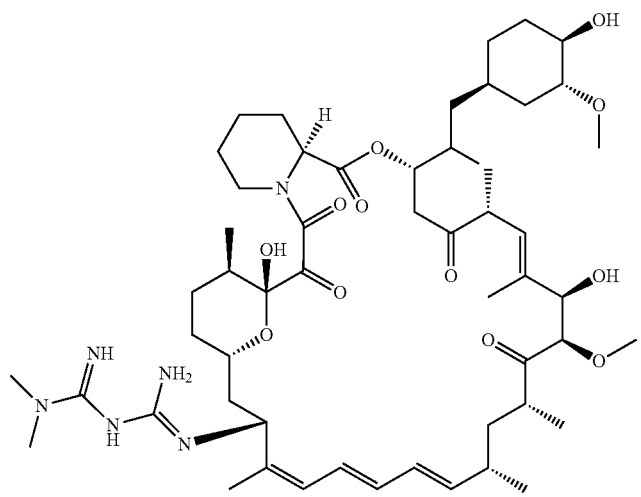
I-40
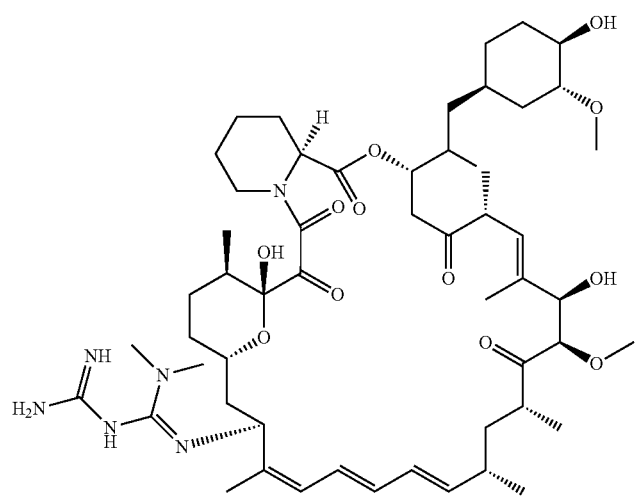 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](/N=C(/NC(=N)N)N(C)C)C[C@@H]3CC[C@@H](C)[C@@](O)(O3)C(=O)C(=O)N3CCCC[C@H]3C(=O)O2)CC[C@H]1O]
I-41

TABLE 1-continued
Exemplary Compounds
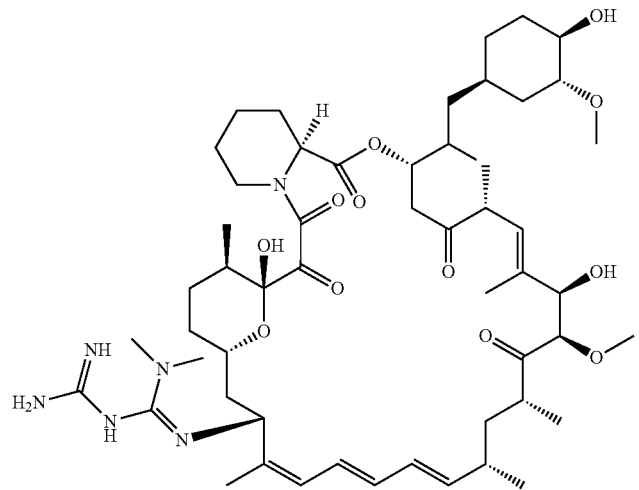 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](/N=C(/NC(=N)N)N(C)C)C[C@@H]3CC[C@@H](C)[C@@](O)(O3)C(=O)C(=O)N3CCCC[C@H]3C(=O)O2)CC[C@H]1O]
I-42
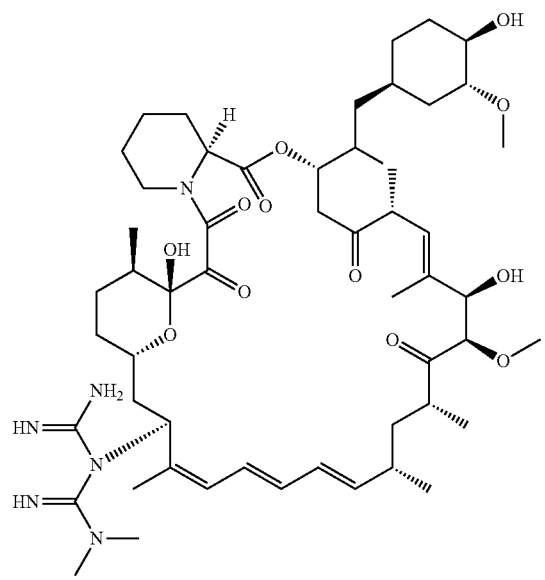 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](N(C(=N)N)C(=N)N(C)C)C[C@@H]3CC[C@@H](C)[C@@](O)(O3)C(=O)C(=O)N3CCCC[C@H]3C(=O)O2)CC[C@H]1O]
I-43

TABLE 1-continued
Exemplary Compounds
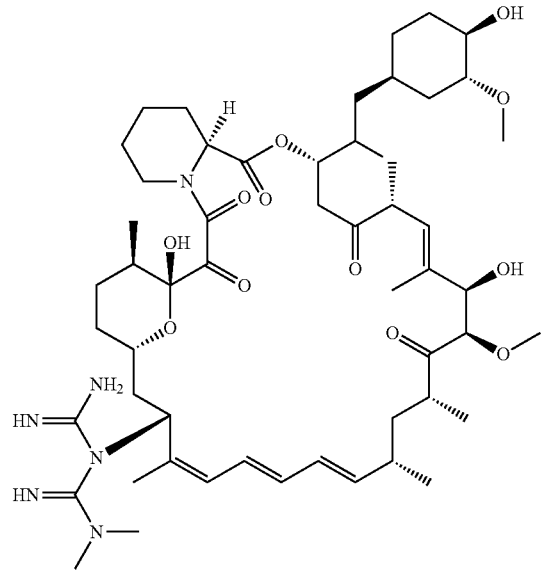 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](N(C(=N)N)C(=N)N(C)C)C[C@@H]3CC[C@@H](C)[C@@](O)(O3)C(=O)C(=O)N3CCCC[C@H]3C(=O)O2)CC[C@H]1O]
I-44
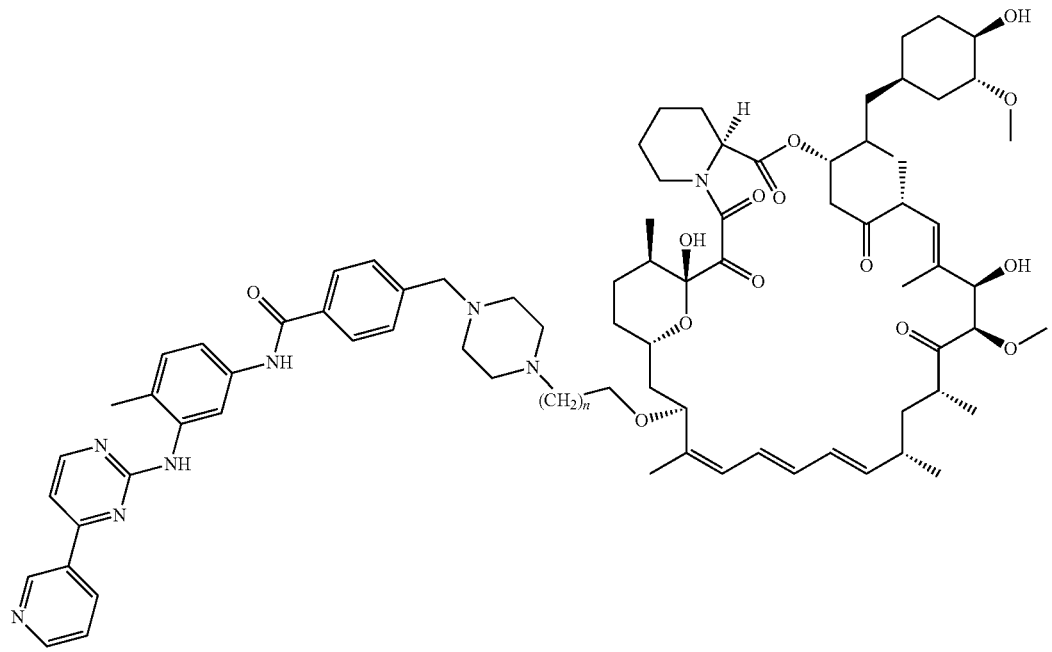
n = 1, 2
I-45

TABLE 1-continued
Exemplary Compounds
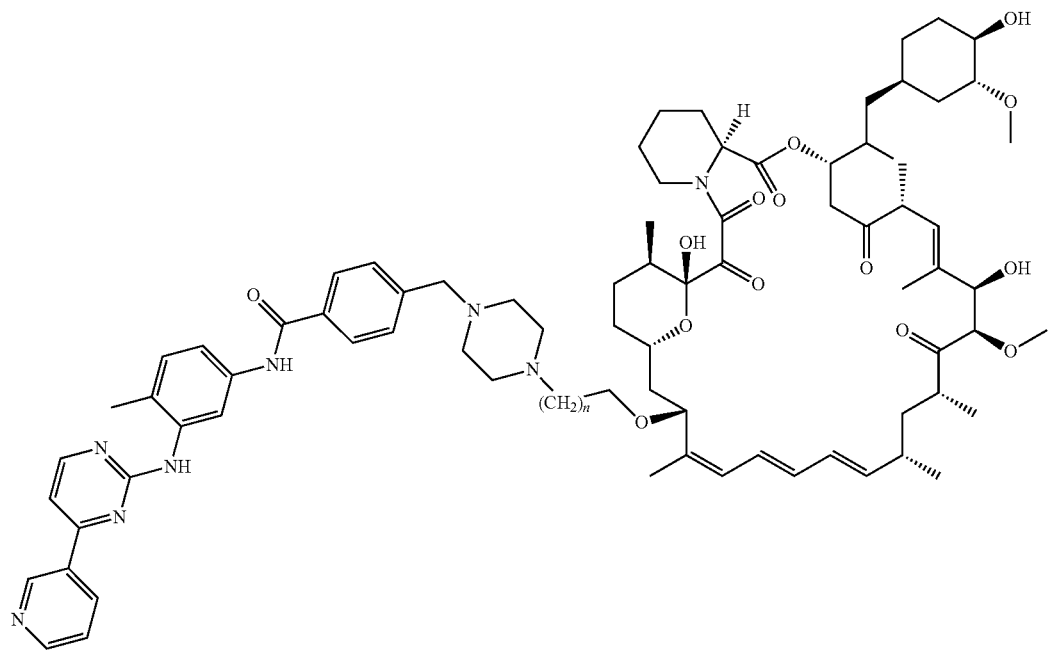
n = 1, 2
I-46
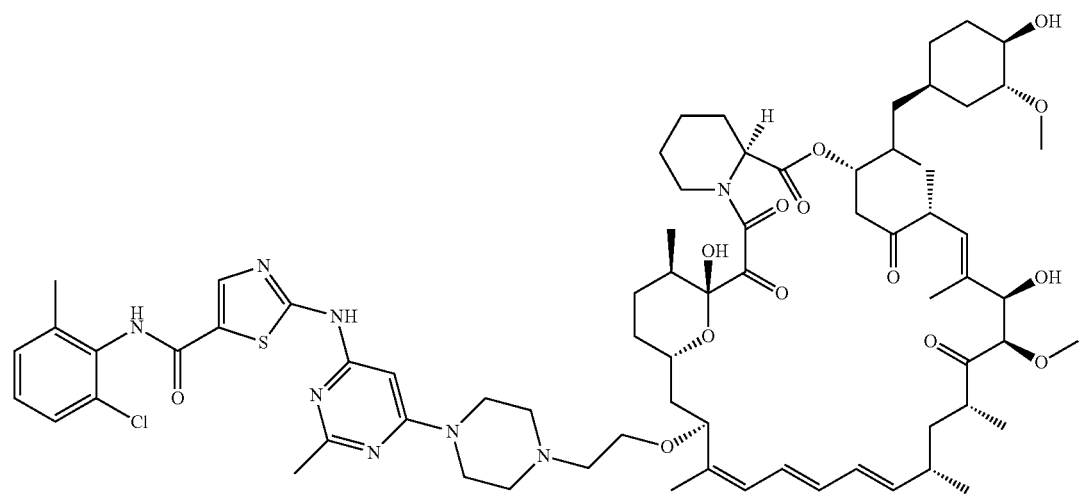 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@@H](OCCN3CCN(c4cc(Nc5ncc(C(=O)Nc6c(C)cccc6Cl)s5)nc(C)n4)CC3)C[C@@H]3CC[C@@H](C)[C@@](O)(O3)C(=O)C(=O)N3CCCC[C@H]3C(=O)O2)CC[C@H]1O]
I-47

TABLE 1-continued
Exemplary Compounds
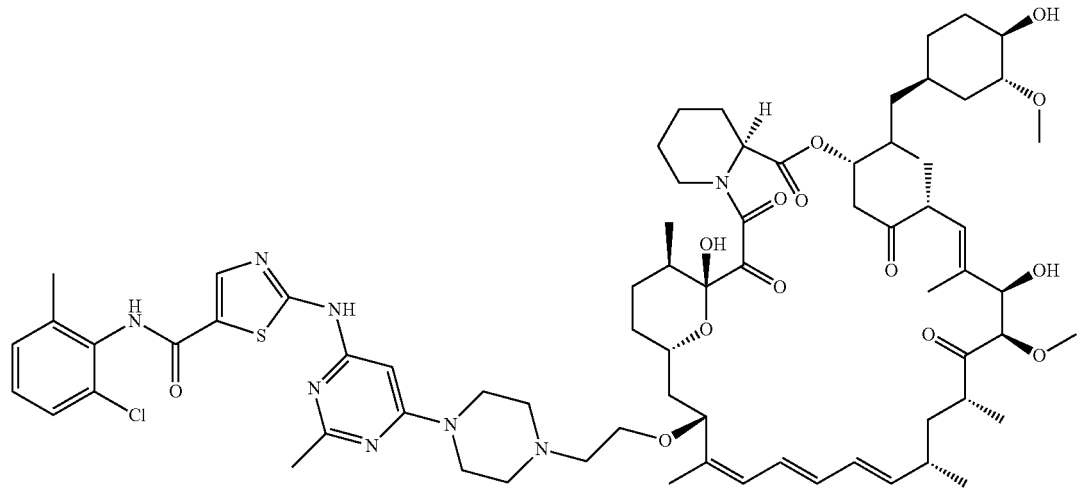 [SMILES: CO[C@@H]1C[C@@H](CC(C)[C@@H]2CC(=O)[C@H](C)/C=C(\C)[C@@H](O)[C@@H](OC)C(=O)[C@H](C)C[C@H](C)/C=C/C=C/C=C(/C)[C@H](OCCN3CCN(c4cc(Nc5ncc(C(=O)Nc6c(C)cccc6Cl)s5)nc(C)n4)CC3)C[C@@H]3CC[C@@H](C)[C@@](O)(O3)C(=O)C(=O)N3CCCC[C@H]3C(=O)O2)CC[C@H]1O]
I-48
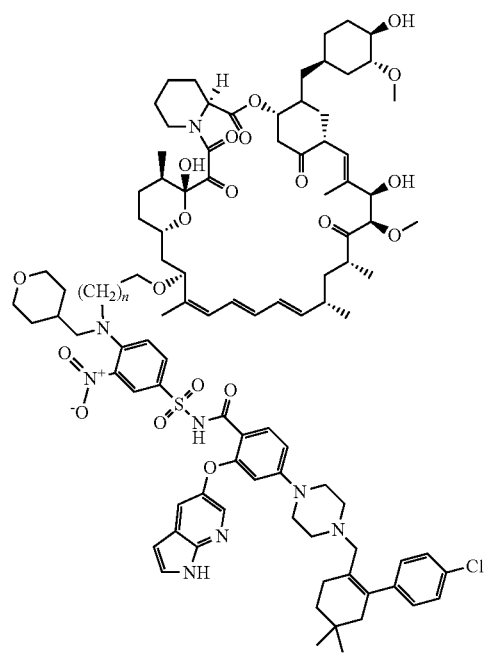
n = 1, 2
I-49

TABLE 1-continued
Exemplary Compounds
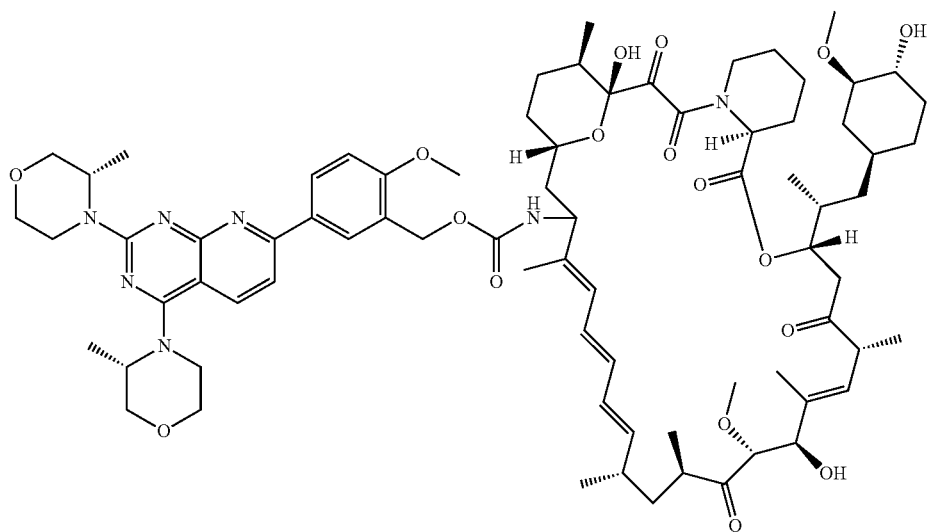 [SMILES: COc1ccc(-c2ccc3c(N4CCOC[C@@H]4C)nc(N4CCOC[C@@H]4C)nc3n2)cc1COC(=O)NC1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]
n = 1, 2
I-50
I-51

TABLE 1-continued
Exemplary Compounds
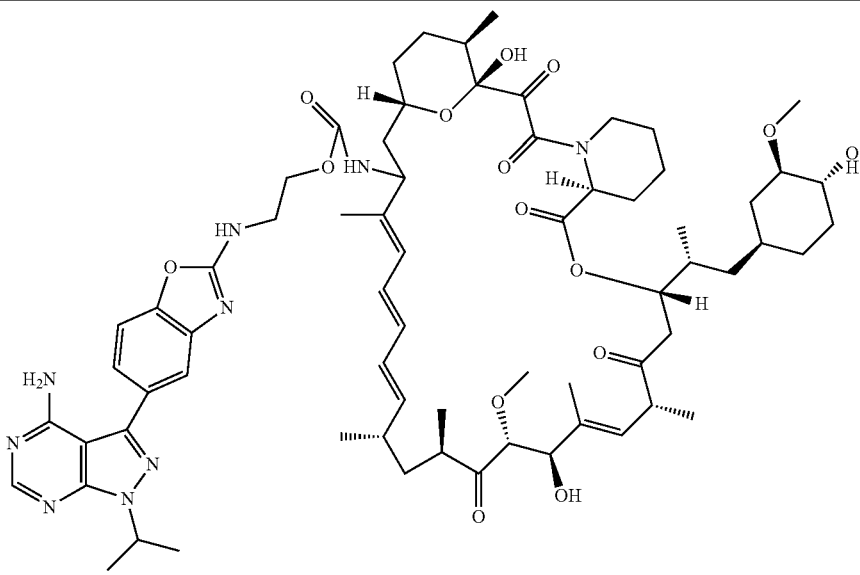
I-52
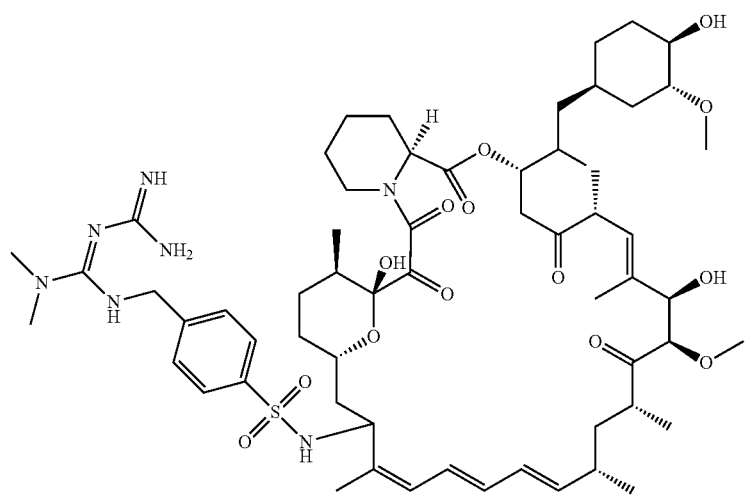
I-53
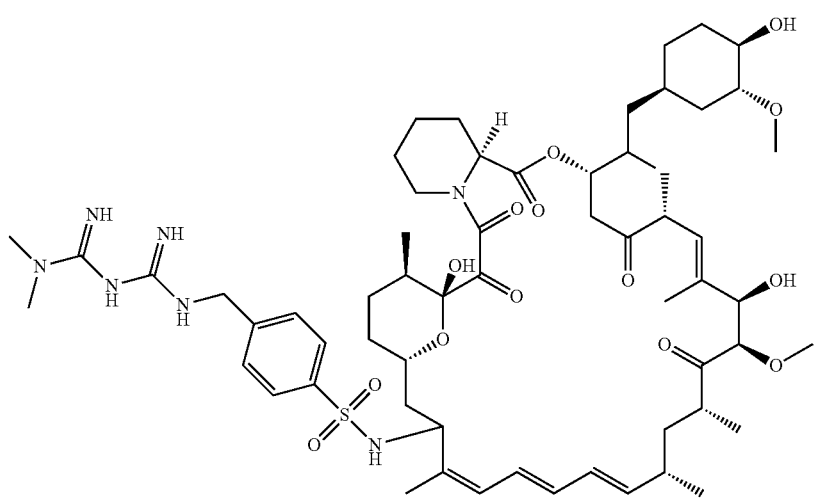

TABLE 1-continued

Exemplary Compounds

I-54

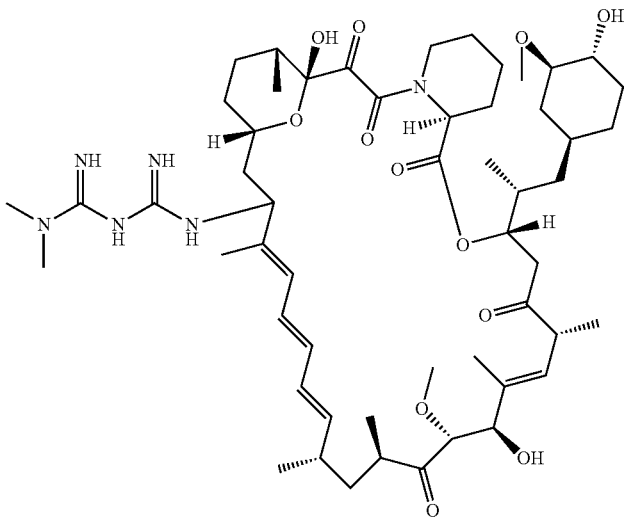 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(CNC(=N)NC(=N)N(C)C)C[C@@H]3CC[C@@H](C)[C@@](O)(O3)C(=O)C(=O)N3CCCC[C@H]3C(=O)O2)CC[C@H]1O]

I-55

In some embodiments, the present invention provides a compound set forth in Table 1, above, or a pharmaceutically acceptable salt thereof. It will be appreciated that the present invention also provides a compound set forth in Table 1, above, as a racemic mixture at the C7 position, or a pharmaceutically acceptable salt thereof.

As described here, a provided compound of formula I or formula II is a hybrid molecule having a rapamycin portion covalently attached to an additional therapeutic agent, $R^1$, via the $L^1$ linker. Such covalent attachment of the additional therapeutic agent is achieved by nucleophilic addition of the therapeutic agent at the C7 position of rapamycin. Methods for preparing a C7 derivative of rapamycin, or analog thereof, are known in the art and include those described by Luengo et al., Chemistry & Biology, 1995, 2, 471-481.

One of ordinary skill in the art will recognize that certain $R^1$ therapeutic agents have more than one moiety suitable for nucleophilic addition to the rapamycin C7 position. It will be appreciated that provided compounds encompass attachment of $R^1$ at any such moiety.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit mTORC1, in a biological sample or in a patient. In certain embodiments, the amount of compound in compositions of this invention is such that is effective to measurably inhibit mTORC1, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of mTORC1.

The activity of a compound utilized in this invention as an inhibitor of mTORC1, may be assayed in vitro, in vivo or in a cell line. In vitro assays include assays that determine the inhibition of mTORC1. Detailed conditions for assaying a compound utilized in this invention as an inhibitor of mTORC1 are well known to one of ordinary skill in the art. Such methods are described in detail by Liu et al., *Cancer Research*, 73(8), Apr. 15, 2013 and Liu et al., *J. Biological Chemistry*, vol 287, no. 13, pp 9742-9752 (2012).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of mTORC1 and are therefore useful for treating one or more disorders associated with activity of mTORC1. Thus, in certain embodiments, the present invention provides a method for treating an mTORC1-mediated disorder comprising the step of administering to a patient in need thereof a compound of the present invention, or pharmaceutically acceptable composition thereof.

As used herein, the terms "mTORC1-mediated" disorders, diseases, and/or conditions as used herein means any disease or other deleterious condition in which mTORC1, is known to play a role. Accordingly, another embodiment of the present invention relates to treating or lessening the severity of one or more diseases in which mTORC1 is known to play a role. In certain embodiments, an mTORC1-mediated disorder, disease, and/or condition is selected from those described by Matt Kaeberlin, *Scientifica*, vol. 2013, Article ID 849186.

The methods described herein include methods for the treatment of cancer in a subject. As used in this context, to "treat" means to ameliorate or improve at least one symptom or clinical parameter of the cancer. For example, a treatment can result in a reduction in tumor size or growth rate. A treatment need not cure the cancer or cause remission 100% of the time, in all subjects.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells.

Cancers that can be treated or diagnoses using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the cancers that are treated by the methods described herein are cancers that have increased levels of mTORC1 or an increased expression or activity of a mTORC1 relative to normal tissues or to other cancers of the same tissues; methods known in the art and described herein can be used to identify those cancers. In some embodiments, the methods include obtaining a sample comprising cells of the cancer, determining the mTORC1 activity in the sample, and administering a treatment as described herein (e.g., a provided inhibitor of mTORC1). In some embodiments, the cancer is one that is shown herein to have increased levels of mTORC1 activity In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by inhibiting mTORC1 activity. Cellular proliferative disorders described herein include, e.g., cancer, obesity, and proliferation-dependent diseases. Such disorders may be diagnosed using methods known in the art.

Cancer

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body.

Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of modulating Sestrin-GATOR2 interaction thereby selectively modulating mTORC1 activity indirectly in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

In other embodiments, the present invention provides a method for treating a disorder mediated by mTORC1 in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™) rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4th Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

List of abbreviations used in the experimental section.

Anhyd: anhydrous aq: aqueous

CDI: 1,1'-carbonyldiimidazole m-CPBA: m-chloroperbenzoic acid

DCM: dichloromethane

DIPEA: N,N-diisopropylethylamine

DMF: N,N-dimethylformamide

DMSO: dimethyl sulfoxide dppf: 1,1'-ferrocenediyl-bis(diphenylphosphine)

EA: ethyl acetate

ESI: electrospray ionization $Et_3N$: triethylamine $Et_2O$: diethyl ether

EtOAc: ethyl acetate

EtOH: ethanol h: hours $HCOONH_4$: ammonium formate

HPLC: high performance liquid chromatography

M: molar

Me: methyl

MeCN: acetonitrile

MeOH: methanol min: minutes mL: milliliters mM: millimolar mmol: millimoles $Na_2CO_3$: sodium carbonate $NaHCO_3$: sodium bicarbonate NMR: Nuclear Magnetic Resonance ° C.: degrees Celsius PE: petroleum ether prep-HPLC: preparative high performance liquid chromatography PMB: para-methoxybenzyl $PPh_3$: triphenylphosphine rt: room temperature sat: saturated SFC: supercritical fluid chromatography TEA: triethylamine TFA: trifluoracetic acid THF: tetrahydrofuran Example 1. Synthesis of 7-Demethoxy-7-[5-(2,4-bis ((S)-3-methylmorpholino)pyrido[2,3-d]pyrimidin-7-yl)-2-methoxybenzoxy carbonylamino]rapamycin, I-51
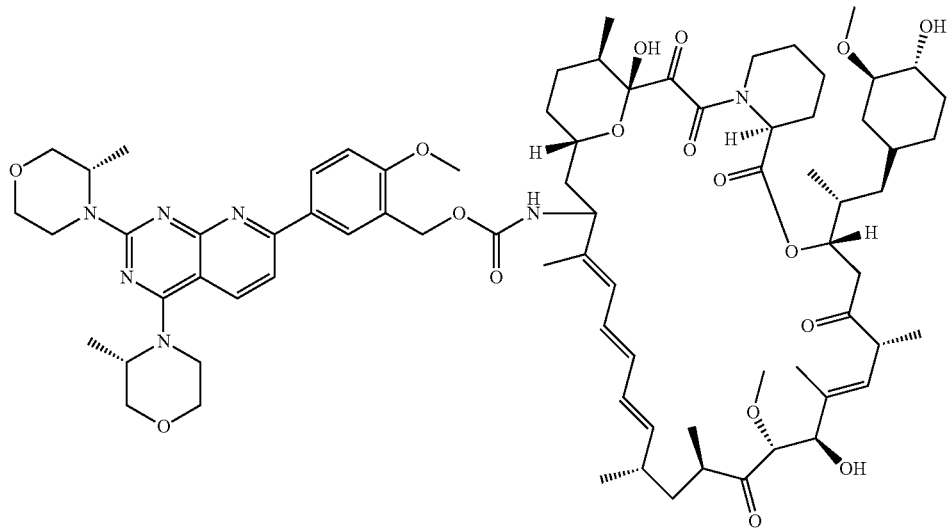
Synthetic Scheme:
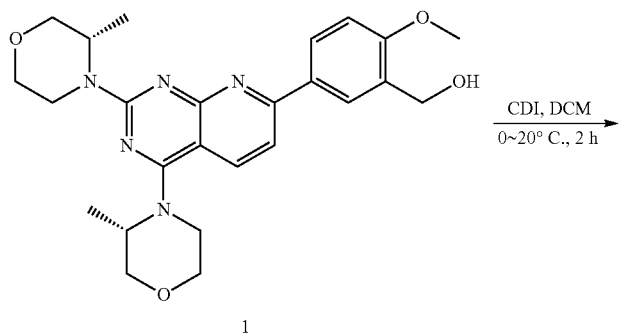
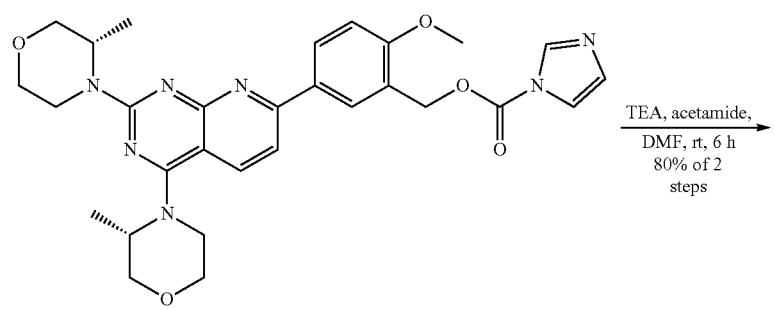

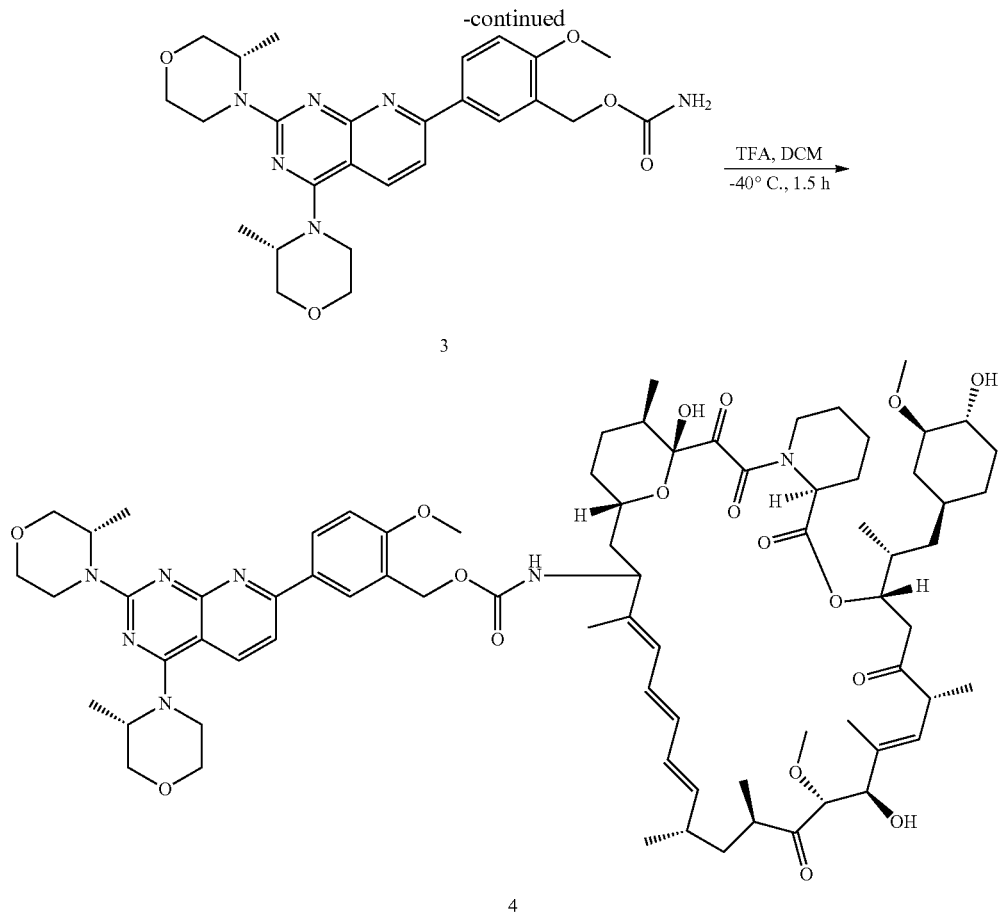

Procedures and Characterization

Step 1: 5-(2,4-Bis((S)-3-methylmorpholino)pyrido[2,3-d]pyrimidin-7-yl)-2-methoxybenzyl 1H-imidazole-1-carboxylate To a stirred solution of (5-(2,4-bis((S)-3-methylmorpholino)pyrido[2,3-d]pyrimidin-7-yl)-2-methoxyphenyl)methanol (200 mg, 0.43 mmol) in dry DCM (10 mL) was added CDI (140 mg, 0.86 mmol) at 0° C. under N$_2$. The reaction solution was stirred at rt for 3 hrs, concentrated and carried on to the next step in the synthetic scheme directly. ESI-MS (EI$^+$, m/z): 560.2 [M+H]$^+$.

Step 2: 5-(2,4-Bis((S)-3-methylmorpholino)pyrido[2,3-d]pyrimidin-7-yl)-2-methoxybenzyl carbamate To a stirred solution of 5-(2,4-bis((S)-3-methylmorpholino)pyrido[2,3-d]pyrimidin-7-yl)-2-methoxybenzyl 1H-imidazole-1-carboxylate (240 mg, 0.43 mmol) in dry DMF (5 mL) was added TEA (0.9 ml, 6.45 mmol) at rt, followed by the addition of ammonium acetate (254 mg, 4.3 mmol). The resultant solution was stirred at rt for 6 h, quenched with water and extracted with EtOAc. The organic layer was washed with brine, dried, filtered, concentrated and carried on to the next step in the synthetic scheme directly. ESI-MS (EI$^+$, m/z): 509.2 [M+H]$^+$. $^1$H NMR (500 MHz, DMSO-d$_6$) δ 8.18-8.16 (m, 3H), 7.59 (d, J=8.5 Hz, 1H), 7.17 (d, J=8.5 Hz, 1H), 5.07 (s, 2H), 4.77-4.76 (m, 1H), 4.44-4.41 (m, 2H), 3.96-3.87 (m, 6H), 3.75-3.73 (m, 2H), 3.67-3.59 (m, 4H), 3.47-3.42 (m, 1H), 3.24-3.18 (m, 1H), 1.37 (d, J=6.5 Hz, 3H), 1.25 (d, J=6.5 Hz, 3H).

Step 3: 7-Demethoxy-7-[5-(2,4-bis((S)-3-methylmorpholino)pyrido[2,3-d]pyrimidin-7-yl)-2-methoxybenzoxy carbonylamino]rapamycin To a solution of rapamycin (46 mg, 0.05 mmol) in dry DCM (3 mL) was added TFA (0.24 mL) at −40° C. under N$_2$. The reaction solution was stirred at −40° C. for 10 min and 5-(2,4-bis((S)-3-methylmorpholino)pyrido[2,3-d]pyrimidin-7-yl)-2-methoxybenzyl carbamate (50 mg, 0.1 mmol) was added in one portion and stirred under −30° C. for 1 h, then quenched with ice cold NaHCO$_3$ aqueous solution and EtOAc. The organic layer was washed with ice-cold water, 0.4 M citric aqueous solution twice, then washed with brine, dried over Na$_2$SO$_4$, filtered and concentrated. The crude was purified by combiflash (ISCO, 20 g silica gel, PE:DCM:EA:MeOH=42:42:15:1~2, then PE: DCM:EA:MeOH=45:45:15:5~8) to obtain 7-Demethoxy-7-[5-(2,4-bis((S)-3-methylmorpholino)pyrido[2,3-d]pyrimidin-7-yl)-2-methoxybenzoxy carbonylamino]rapamycin as a yellow solid (5 mg, 7%). ESI-MS (EI$^+$, m/z): 1390.8 [M+H]$^+$.

$^1$H NMR (500 MHz, CDCl$_3$) δ 8.60 (s, 1H), 8.22-8.15 (m, 1H), 7.99 (d, J=8.0 Hz, 1H), 7.78 (d, J=9.0 Hz, 1H), 7.74-7.69 (m, 1H), 7.54-7.52 (m, 1H), 6.96 (d, J=8.5 Hz, 2H), 6.37-6.01 (m, 4H), 5.38-5.09 (m, 15H), 4.99-4.11 (m, 5H), 4.08 (d, J=6.5 Hz, 2H), 4.01-3.95 (m, 2H), 3.91-3.55 (m, 16H), 3.40-3.33 (m, 6H), 2.93-2.61 (m, 2H), 2.22 (t, J=8.0 Hz, 3H), 1.13-0.93 (m, 44H).

Example 2. Synthesis of 7-Demethoxy-7-[2-(5-(4-amino-1-isopropyl-1H-pyrazolo[3,4-d]pyrimidin-3-yl)benzo[d]oxazol-2-ylamino)ethyl carbonylamino] rapamycin, I-52
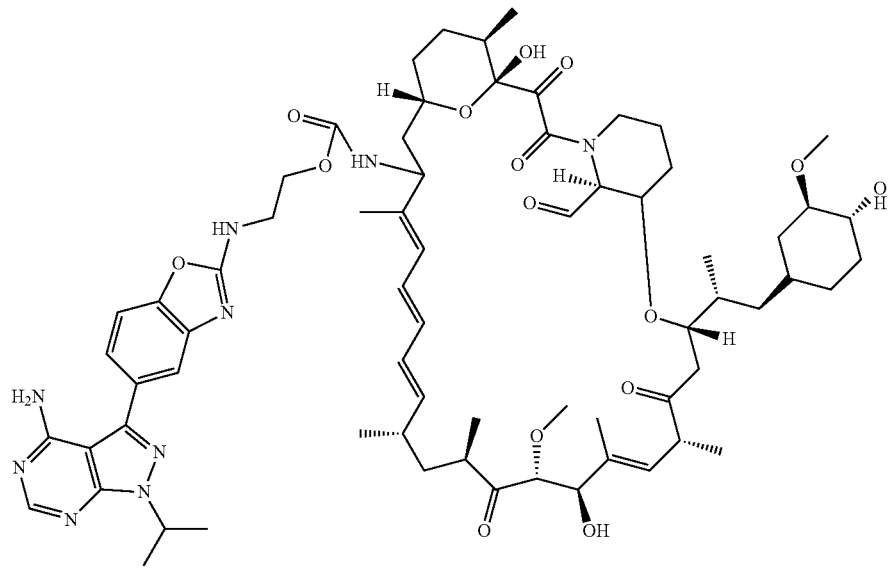
Synthetic Scheme:
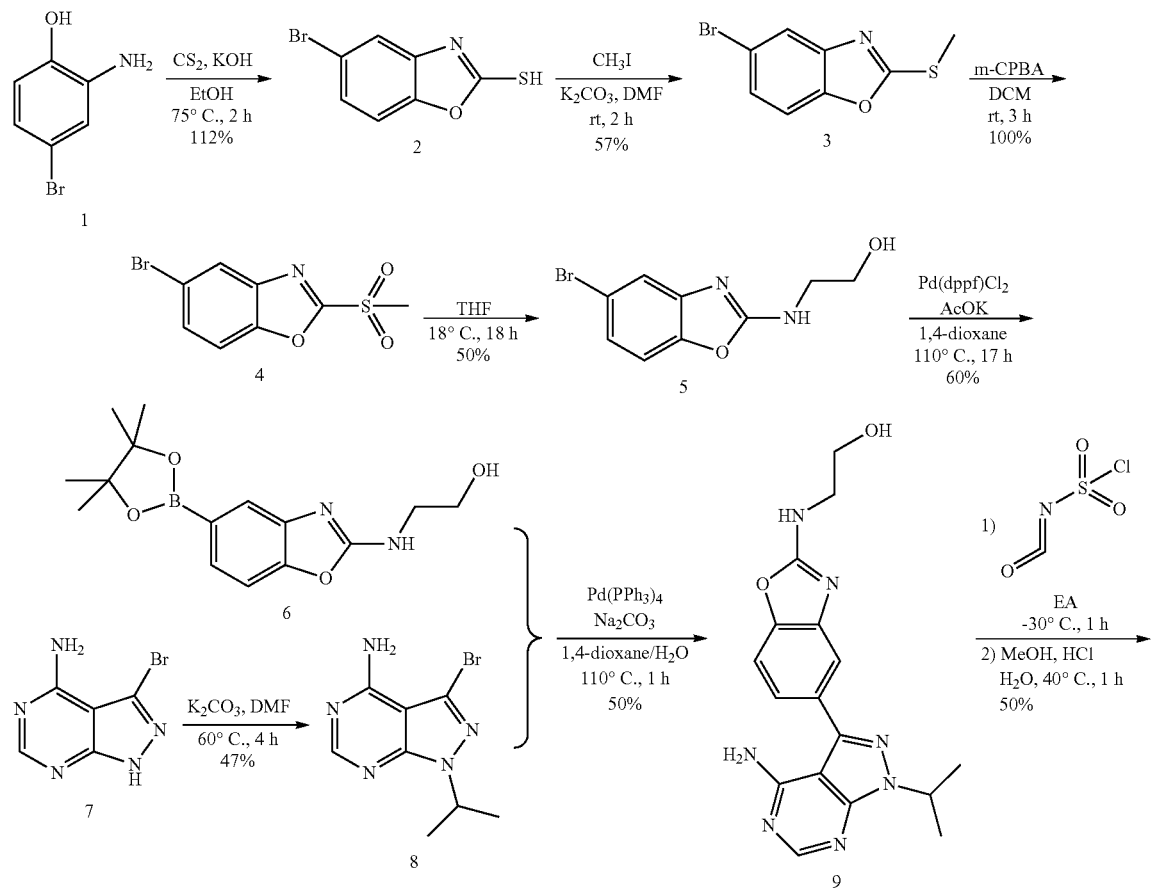

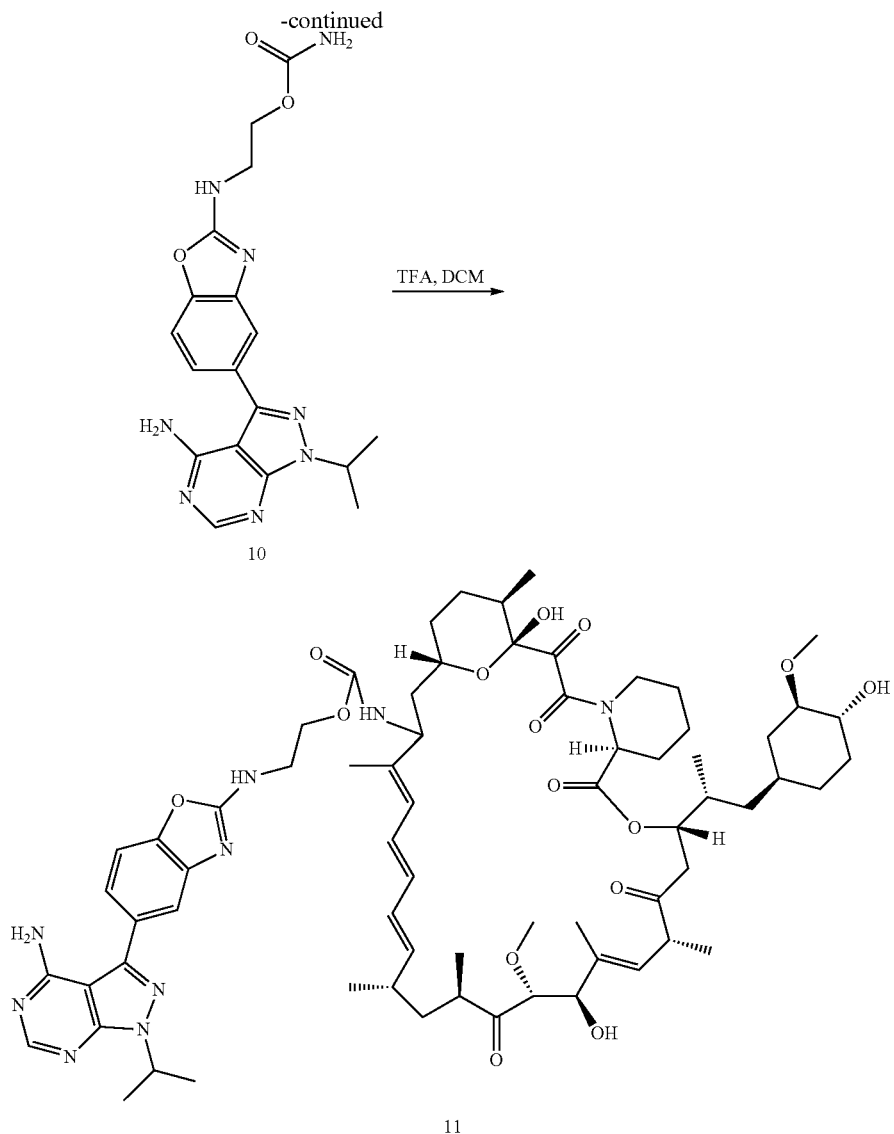

Procedures and Characterization

Step 1: 5-Bromobenzo[d]oxazole-2-thiol

To a 500 mL round-bottom flask containing 2-amino-4-bromophenol (14.5 g, 76.7 mmol) in EtOH (150 mL) and $CS_2$ (13 mL, 0.21 mol, 16.4 g) at 0° C. (cooled by ice-water bath) was added KOH (6.0 g, 0.107 mol) in portions over 2 mins. The resulting mixture was stirred at 75° C. for 2 h. The reaction mixture was evaporated and the residue was diluted with EtOAc (900 mL), acidified by 1 N HCl (100 mL), washed by $H_2O$ (500 mL). The solid was filtered and dried to give 9.3 g desired product. The EtOAc phase was dried and evaporated to give another 10 g desired product. Total 5-bromobenzo[d]oxazole-2-thiol (19.3 g) was obtained as a tan solid. ESI-MS (EI$^+$, m/z):228 [M+H]$^+$. $^1$H NMR (500 MHz, DMSO-$d_6$) δ14.03 (s, 1H), 7.49 (d, J=8.5 Hz, 1H), 7.44 (dd, J=8.6, 1.9 Hz, 1H), 7.41 (d, J=1.6 Hz, 1H).

Step 2: 5-Bromo-2-(methylthio)benzo[d]oxazole

A mixture of 5-bromobenzo[d]oxazole-2-thiol (11.5 g, 50 mmol), $K_2CO_3$ (13.8 g, 0.1 mol) in DMF (115 mL) was cooled to 0° C., MeI (13 g, 92 mmol) was added dropwise and the resulting mixture was stirred at rt for 2 h before being evaporated. The residue was poured into cold water (500 mL), extracted with EtOAc (250 mL×2), washed with $H_2O$ and brine (250 mL each), dried and evaporated to give 5-bromo-2-(methylthio)benzo[d]oxazole (8 g, 63% 2 steps) as a tan solid. ESI-MS (EI$^+$, m/z): 244 [M+H]$^+$. $^1$H NMR (500 MHz, DMSO-$d_6$) δ 7.88 (d, J=1.9 Hz, 1H), 7.64 (d, J=8.6 Hz, 1H), 7.48 (dd, J=8.6, 2.0 Hz, 1H), 2.77 (s, 3H).

Step 3: 5-Bromo-2-(methylsulfonyl)benzo[d]oxazole

To a solution of 5-bromo-2-(methylthio)benzo[d]oxazole (1.0 g, 4.1 mmol) in DCM (20 mL) was added m-CPBA (1.42 g, 8.2 mmol) at 25° C. The resultant solution was stirred at 25° C. for 2 h and then quenched with DCM (20 mL). The organic layer was washed with aqueous $NaHCO_3$ solution (30 mL×2), brine (30 mL), dried ($Na_2SO_4$), filtered and concentrated to obtain 5-bromo-2-(methylsulfonyl)benzo[d]oxazole (1.1 g, 99%) as a red solid. The crude was taken to the next step directly.

Step 4: 2-(5-Bromobenzo[d]oxazol-2-ylamino)ethanol

A solution of 5-bromo-2-(methylsulfonyl)benzo[d]oxazole (5.0 g, 19.3 mmol), 2-aminoethanol (1.8 g, 28.9 mmol) and DIPEA (6.7 mL) in THF (60 mL) was stirred at rt for 18 h. The resultant solution was concentrated and the residue was redissolved in EtOAc (500 mL), the solid was filtered off and the filtrate was concentrated to obtain the crude product. The crude product was recrystalled with EtOAc to obtain 2-(5-bromobenzo[d]oxazol-2-ylamino)ethanol (4.0 g, 87%) as a pink solid.

$^1$H NMR (500 MHz, DMSO-$d_6$) δ 8.19 (t, J=5.7 Hz, 1H), 7.40 (d, J=1.8 Hz, 1H), 7.31 (d, J=8.4 Hz, 1H), 7.11 (dd, J=8.4, 1.9 Hz, 1H), 4.82 (t, J=5.5 Hz, 1H), 3.56 (q, J=5.8 Hz, 2H), 3.35 (dd, J=11.3, 5.4 Hz, 2H).

Step 5: 2-(5-(4,4,5,5-Tetramethyl-1,3,2-dioxaborolan-2-yl)benzo[d]oxazol-2-ylamino)ethanol A solution of 2-(5-bromobenzo[d]oxazol-2-ylamino)ethanol (2.0 g, 7.81 mmol), 4,4,4',4',5,5,5',5'-octamethyl-2,2'-bi(1,3,2-dioxaborolane) (2.98 g, 11.72 mmol), Pd(dppf)Cl$_2$ (0.57 g, 0.781 mmol) and KOAc (2.45 g, 24.99 mmol) in 1,4-dioxane (40 mL) was stirred at 100° C. for 1 h. The solution was quenched with water (100 mL) and extracted with EtOAc (100 mL×2). The combined organic layer was washed with water (50 mL), brine (100 mL), dried (Na$_2$SO$_4$), filtered and concentrated to obtain a brown oil. The crude was purified by ISCO to obtain 2-(5-(4,4,5,5-tetram ethyl-1,3,2-dioxaborolan-2-yl)benzo[d]oxazol-2-ylamino)ethanol (2.4 g, 100%) as a dark brown solid.

$^1$H NMR (500 MHz, DMSO-$d_6$) δ 7.99 (s, 1H), 7.46 (s, 1H), 7.33 (s, 2H), 4.81 (t, J=5.3 Hz, 1H), 3.57 (dd, J=11.2, 5.5 Hz, 2H), 3.36 (dd, J=11.7, 5.8 Hz, 2H), 1.29 (s, 12H).

Step 6: 3-Bromo-1-isopropyl-1H-pyrazolo[3,4-d]pyrimidin-4-amine

The solution of 3-bromo-1H-pyrazolo[3,4-d]pyrimidin-4-amine (10.7 g, 0.05 mol), K$_2$CO$_3$ (13.8 g, 0.1 mol) in dry DMF (60 mL) was stirred at 60° C. for 30 min, then 2-bromopropane (5 mL, 0.0525 mol) was added and the resultant solution was stirred at 60° C. for 3 h, cooled down, filtered, and concentrated. The residue was diluted with isopropyl acetate (200 mL). The organic layer was washed with water (100 mL), brine (100 mL), dried (Na$_2$SO$_4$), filtered and concentrated. The crude was triturated with MeOH to obtain 3-bromo-1-isopropyl-1H-pyrazolo[3,4-d]pyrimidin-4-amine (6.0 g, 47%) as a light yellow solid.

$^1$H NMR (500 MHz, CDCl$_3$) δ 8.32 (s, 1H), 6.20 (s, 2H), 5.10 (dt, J=13.4, 6.7 Hz, 1H), 1.54 (d, J=6.7 Hz, 6H).

Step 7: 2-(5-(4-Amino-1-isopropyl-1H-pyrazolo[3,4-d]pyrimidin-3-yl)benzo[d]oxazol-2-ylamino)ethanol A solution of 3-bromo-1-isopropyl-1H-pyrazolo[3,4-d]pyrimidin-4-amine (1.65 g, 6.48 mmol), 2-(5-(4,4,5,5-tetramethyl-1,3,2-dioxaborolan-2-yl)benzo[d]oxazol-2-ylamino) ethanol (2.0 g, 7.81 mmol), Pd(PPh$_3$)$_4$ (604 mg, 0.523 mmol) and Na$_2$CO$_3$ (3.43 g, 32.41 mmol) in 1,4-dioxane (20 ml)/water (6 ml) was stirred at 100° C. for 1 h. The reaction mixture was filtered, quenched with water (100 mL), extracted with EtOAc (100 mL×2), dried (Na$_2$SO$_4$), filtered and concentrated. The crude was purified by ISCO to obtain 2-(5-(4-amino-1-isopropyl-1H-pyrazolo[3,4-d]pyrimidin-3-yl)benzo[d]oxazol-2-ylamino)ethanol (1.5 g, 65%) as a white solid. ESI-MS (Et, m/z): 354 [M+H]$^+$ $^1$H NMR (500 MHz, DMSO-$d_6$) δ 8.39 (s, 1H), 8.18 (t, J=5.7 Hz, 1H), 7.51 (d, J=8.1 Hz, 1H), 7.46 (s, 1H), 7.28-7.24 (m, 1H), 5.09 (dt, J=13.1, 6.6 Hz, 1H), 3.59 (t, J=5.9 Hz, 2H), 3.40 (q, J=5.8 Hz, 2H), 1.51 (d, J=6.7 Hz, 6H).

Step 8: 2-(5-(4-Amino-1-isopropyl-1H-pyrazolo[3,4-d]pyrimidin-3-yl)benzo[d]oxazol-2-ylamino)ethyl carbamate A solution of 2-(5-(4-amino-1-isopropyl-1H-pyrazolo[3,4-d]pyrimidin-3-yl) benzo[d]oxazol-2-ylamino) ethanol (400 mg, 1.14 mmol) and sulfurisocyanatidic chloride (402 mg, 2.84 mmol) in EtOAc (15 mL) was stirred at −30° C. for 1 h. Conc.HCl aqueous solution (1.5 mL), H$_2$O (1.5 mL) and MeOH (3.0 mL) was added and stirred at 40° C. for 1 h. K$_2$CO$_3$ was added and the reaction mixture was extracted with EtOAc (15 mL×2), dried (Na$_2$SO$_4$), filtered and concentrated. The crude was purified by reverse-phase biotage to obtain 2-(5-(4-amino-1-isopropyl-1H-pyrazolo[3,4-d]pyrimidin-3-yl)benzo[d]oxazol-2-yl amino)ethyl carbamate (200 mg, 45%) as a white solid. ESI-MS (EI$^+$, m/z): 397 [M+H]$^+$ $^1$H NMR (500 MHz, DMSO-$d_6$) δ 8.39 (s, 1H), 8.29 (t, J=5.7 Hz, 1H), 7.52 (d, J=8.1 Hz, 1H), 7.48 (s, 1H), 7.31-7.24 (m, 1H), 6.61 (s, 2H), 5.09 (dt, J=13.4, 6.6 Hz, 1H), 4.13 (t, J=5.6 Hz, 2H), 3.54 (d, J=5.5 Hz, 2H), 1.51 (d, J=6.7 Hz, 6H).

Step 9: 7-Demethoxy-7-[2-(5-(4-amino-1-isopropyl-1H-pyrazolo[3,4-d]pyrimidin-3-yl) benzo[d]oxazol-2-ylamino)ethyl carbonylamino]rapamycin To a solution of rapamycin (45 mg, 0.05 mmol) in dry DCM (3 mL) was added TFA (0.24 ml) at −40° C. under a N$_2$ atmosphere, the resultant solution was stirred at −40° C. for 10 min, then 2-(5-(4-amino-1-isopropyl-1H-pyrazolo[3,4-d]pyrimidin-3-yl)benzo[d]oxazol-2-ylamino) ethyl carbamate (59 mg, 0.15 mmol) was added in one portion and stirred at this temperature for 1 h, then quenched by ice-cold EtOAc (15 mL), washed with NaHCO$_3$ solution (10 mL) and citric acid aqueous solution (10 mL), brine, dried (Na$_2$SO$_4$), filtered and concentrated. The crude was washed with ether, then purified by reverse-phase biotage (0.025% TFA in H$_2$O/CH$_3$CN) to obtain 7-Demethoxy-7-[2-(5-(4-amino-1-isopropyl-1H-pyrazolo[3,4-d]pyrimidin-3-yl) benzo[d]oxazol-2-ylamino)ethyl carbonyl amino]rapamycin (4.7 mg, 7.3%) as a white solid. ESI-MS (EI$^+$, m/z): 1278.7 [M+H]$^+$ $^1$H NMR (500 MHz, MeOD-$d_4$) δ 8.40 (s, 1H), 7.59 (d, J=13.7 Hz, 1H), 7.52 (d, J=8.2 Hz, 1H), 7.42 (d, J=6.7 Hz, 1H), 6.49-5.93 (m, 4H), 5.48 (s, 1H), 5.34-5.21 (m, 2H), 5.11 (s, 2H), 4.40-4.19 (m, 4H), 4.01-3.93 (m, 1H), 3.76-3.65 (m, 2H), 3.44-3.38 (m, 4H), 3.04-2.45 (m, 4H), 2.35-2.05 (m, 4H), 1.96-1.67 (m, 16H), 1.63 (d, J=6.7 Hz, 10H), 1.55-1.28 (m, 8H), 1.27-0.65 (m, 28H).

Example 3. Synthesis of 7-Demethoxy-7-[(E)-4-((2-carbamimidoyl-3,3-dimethylguanidino)methyl)benzenesulfonamido]rapamycin, I-53
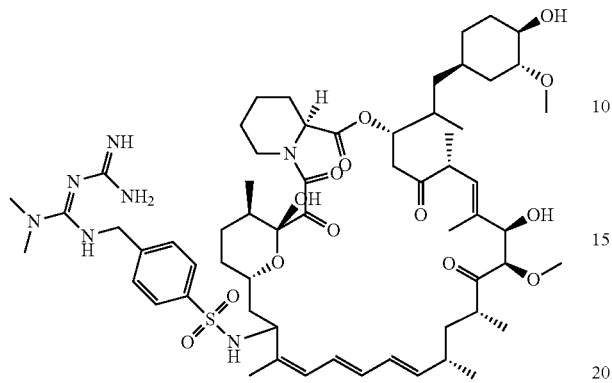
Synthetic Scheme:
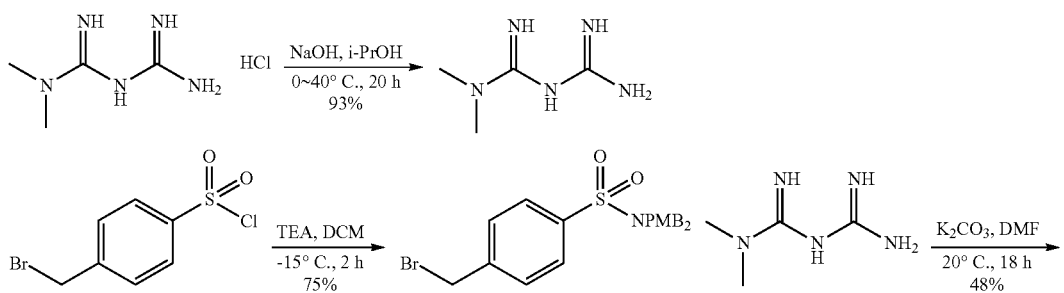
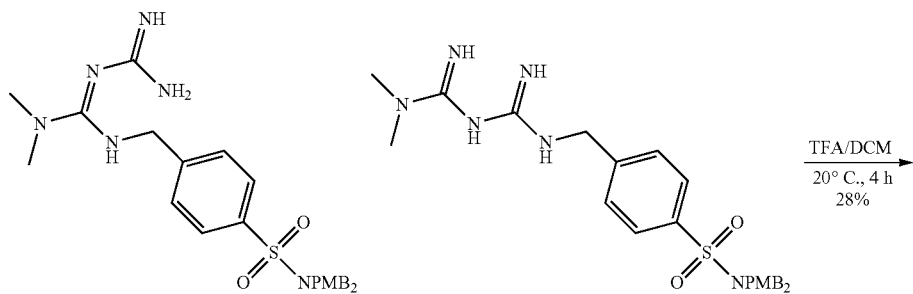
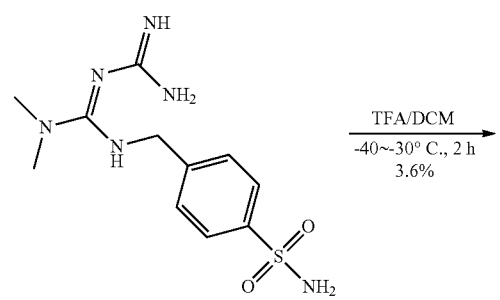

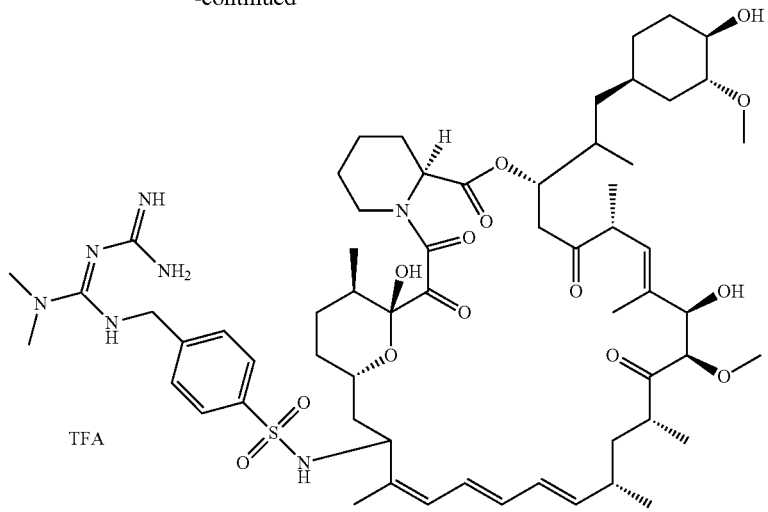

Procedures and Characterization

Step 1: Free Metformin

To a 500 mL round-bottom flask containing metformin hydrochloride (16.6 g, 0.1 mmol) in i-PrOH (150 mL) at 0° C. (cooled by ice-water bath) was added NaOH (4.0 g, 0.1 mol) in portions over 2 mins. The resulting mixture was stirred at 0° C. for 10 mins then 40° C. for 18 h. The reaction mixture was cooled to 20° C., filtered and the filtrate was washed with DCM (50 mL). The combined organics were evaporated and dried in vacuo to give free metformin (12 g, 93%) as white solid. ESI-MS (EI$^+$, m/z):130 [M+H]$^+$ Step 2: 4-(Bromomethyl)-N,N-bis(4-methoxybenzyl)benzenesulfonamide To a 250 mL round-bottom flask containing bis(4-methoxybenzyl)amine (3.9 g, 15.2 mmol) in DCM (dry, 100 mL) at −15° C. (cooled by salt-ice bath) was added 4-(bromomethyl)benzene-1-sulfonyl chloride (4.1 g, 15.2 mmol) in portions over 10 mins. TEA (1.7 g, 16.7 mmol) was added dropwise. The resulting solution was stirred at −15° C. for 2 h. To the reaction solution was added H$_2$O (100 mL). The DCM phase was separated and the aqueous phase was extracted with DCM (100 mL). The combined organic layers were washed with 5% citric acid (200 mL×2), H$_2$O (200 mL), and brine (200 mL) in sequence, then dried over Na$_2$SO$_4$, filtered and evaporated to give the crude which was purified by chromatography (silica gel, PE to DCM) to afford 4-(bromomethyl)-N,N-bis(4-methoxybenzyl)benzenesulfonamide (5.6 g, 75%) as a white solid. ESI-MS (EI$^+$, m/z):490 [M+H]$^+$ $^1$H NMR (500 MHz, DMSO-d$_6$) δ 7.84 (d, J=8.3 Hz, 2H), 7.66 (d, J=8.3 Hz, 2H), 6.96 (d, J=8.5 Hz, 4H), 6.78 (d, J=8.6 Hz, 4H), 4.80 (s, 2H), 4.20 (s, 4H), 3.70 (s, 6H).

Step 3: 4-((N-(Imino(N-(imino(dimethylamino) methyl)amino)methyl)amino)methyl)-N,N-bis(4-methoxybenzyl)benzenesulfonamide To a solution of free metformin (1.0 g, 7.6 mmol) in DMF (20 mL) at 0° C. was added K$_2$CO$_3$ (0.53 g, 3.9 mmol) and 4-(bromomethyl)-N,N-bis(4-methoxybenzyl)benzenesulfonamide (1.9 g, 3.9 mmol) at 0° C. The reaction mixture was stirred at 20° C. for 21 h. The reaction mixture was poured into EA (200 mL) and washed with H$_2$O (100 mL), brine (100 mL), dried over Na$_2$SO$_4$, filtered and evaporated to give the crude which was triturated with Et$_2$O (100 mL) to give a mixture of (E)-4-((2-carbamimidoyl-3,3-dimethyl-guanidino)methyl)-N,N-bis(4-methoxybenzyl)benzenesulfonamide and 4-((N-(imino(N-(imino (dimethylamino) methyl) amino) methyl) amino)methyl)-N,N-bis(4-methoxybenzyl)benzenesulfonamide (1.0 g, 48%) as a tan solid. ESI-MS (EI$^+$, m/z):539 [M+H]$^+$ Step 4: (E)-4-((2-Carbamimidoyl-3,3-dimethyl-guanidino)methyl)benzenesulfonamide To a mixture of (E)-4-((2-carbamimidoyl-3,3-dimethyl-guanidino)methyl)-N,N-bis(4-methoxybenzyl)benzenesulfonamide, 4-((N-(imino(N-(imino(dimethylamino) methyl) amino) methyl) amino) methyl)-N,N-bis(4-methoxybenzyl) benzenesulfonamide (1.0, 1.86 mmol) and anisole (0.8 mL) was added TFA (8 mL) at 0° C. The reaction mixture was stirred at 20° C. for 3 h. The reaction mixture was evaporated and washed by Et$_2$O (100 mL×3) to afford the crude product which was purified by by prep-HPLC (10 mM NH$_4$HCO$_3$ in H$_2$O/MeCN) twice to give (E)-4-((2-carbamimidoyl-3,3-dimethylguanidino)methyl)benzenesulfonamide (160 mg, 28%) as a white solid. ESI-MS (EI$^+$, m/z): 299 [M+H]$^+$. $^1$H NMR (400 MHz, D$_2$O) δ 7.78 (d, J=8.4 Hz, 2H), 7.42 (d, J=8.3 Hz, 2H), 4.54 (s, 2H), 3.07 (s, 6H).

Step 5: 7-Demethoxy-7-[(E)-4-((2-carbamimidoyl-3,3-dimethylguanidino)methyl)benzenesulfonamido] rapamycin To a solution of rapamycin (170 mg, 0.186 mmol) and (E)-4-((2-carbamimidoyl-3,3-dimethylguanidino)methyl) benzenesulfonamide (160 mg, 0.54 mmol) in dry DCM (8 mL) was added TFA (0.6 mL) at −40° C. under N$_2$, the resultant solution was stirred at −40 to −30° C. for 2 h. The resulting reaction mixture was added to cold EtOAc (50 ml) and sat KHCO$_3$ (25 mL) was added and separated. The EtOAc phase was washed with H$_2$O (25 mL), brine (25 mL), dried and evaporated then washed with Et$_2$O (30 mL×2) to give the crude product which was purified by prep-HPLC (0.05% TFA in H$_2$O/MeCN) to give 7-Demethoxy-7-[(E)-4-((2-carbamimidoyl-3,3-dimethylguanidino)methyl)benzenesulfonamido]rapamycin (8 mg, 3.6%) as a white solid. MS (EI+, m/z): 1181 [M+H]$^+$. $^1$H NMR (500 MHz, MeOD) δ 7.83-7.70 (m, 2H), 7.52-7.42 (m, 2H), 6.14 (d, J=43.8 Hz, 3H), 5.69-5.31 (m, 1H), 5.14 (d, J=58.2 Hz, 2H), 4.94 (s, 2H), 4.49 (t, J=15.6 Hz, 2H), 4.17 (d, J=21.2 Hz, 1H), 3.99-3.85 (m, 1.5H), 3.53 (s, 0.5H), 3.43 (d, J=10.4 Hz, 2.5H), 3.31-3.28 (m, 6H), 3.19 (s, 1H), 3.06 (d, J=3.8 Hz, 6H), 3.01-2.89 (m, 2H), 2.89-2.78 (m, 1H), 2.70 (s, 1H), 2.55-2.44 (m, 0.5H), 2.30 (s, 1H), 2.11 (s, 2H), 1.94 (s, 1.5H), 1.79 (d, J=14.9 Hz, 7H), 1.63 (s, 8H), 1.37 (dd, J=32.9, 17.7 Hz, 7.5H), 1.14 (s, 3.5H), 1.09-0.97 (m, 9H), 0.96-0.85 (m, 7H), 0.78-0.64 (m, 1.5H).

Example 4. Synthesis of 7-Demethoxy-7-[4-((N-(imino (N-(imino (dimethylamino) methyl) amino) methyl)amino)methyl)benzenesulfonamido]rapamycin, I-54

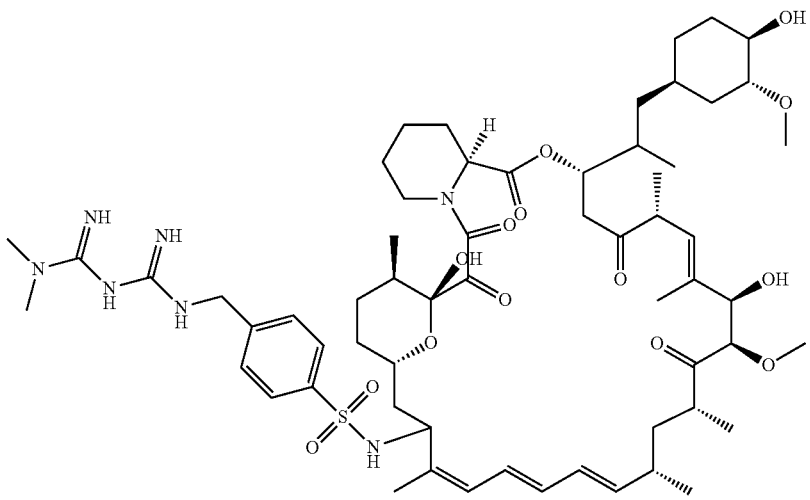

Synthetic Scheme:

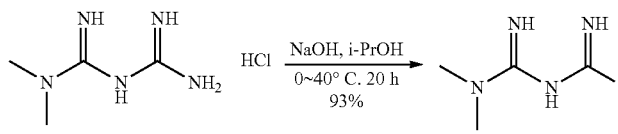

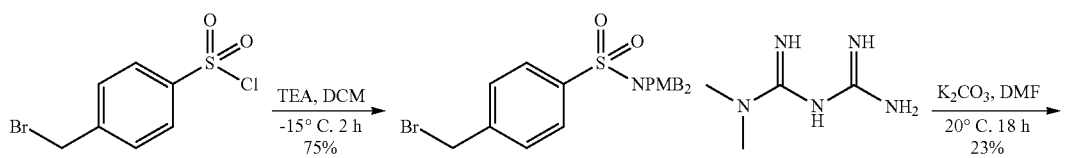

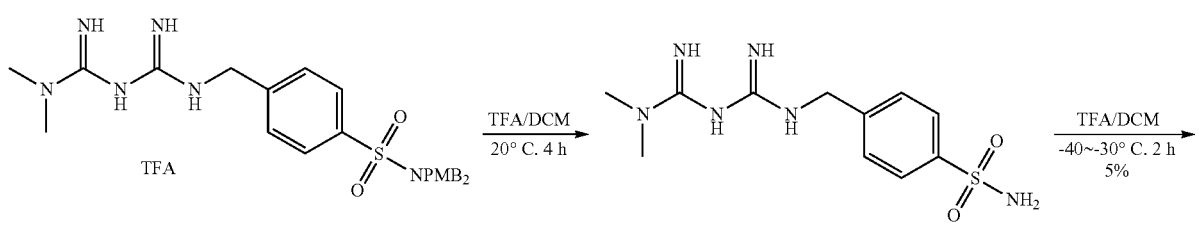

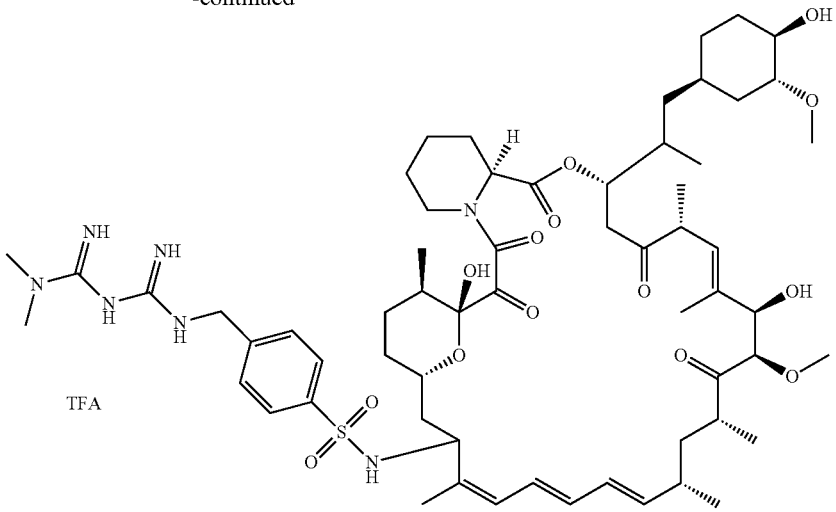

Procedures and Characterization

Step 1: Free Metformin

To a 500 mL round-bottom flask containing metformin hydrochloride (16.6 g, 0.1 mmol) in i-PrOH (150 mL) at 0° C. (cooled by ice-water bath) was added NaOH (4.0 g, 0.1 mol) in portions over 2 mins. The resulting mixture was stirred at 0° C. for 10 mins then 40° C. for 18 h. The reaction mixture was cooled to 20° C., filtered and the filtrate was washed with DCM (50 mL). The combined organics were evaporated and dried in vacuo to give free metformin (12 g, 93%) as a white solid. ESI-MS (EI+, m/z):130 [M+H]+

Step 2: 4-(Bromomethyl)-N,N-bis(4-methoxybenzyl)benzenesulfonamide

To a 250 mL round-bottom flask containing bis(4-methoxybenzyl)amine (3.9 g, 15.2 mmol) in DCM (dry, 100 mL) at −15° C. (cooled by a salt-ice bath) was added 4-(bromomethyl)benzene-1-sulfonyl chloride (4.1 g, 15.2 mmol) in portions over 10 mins. TEA (1.7 g, 16.7 mmol) was added dropwise. The resulting solution was stirred at −15° C. for 2 h. To the reaction solution was added H$_2$O (100 mL), the DCM phase was separated and the aqueous phase was extracted with DCM (100 mL). The combined organics were washed with 5% citric acid (200 mL×2), H$_2$O (200 mL), and brine (200 mL) in sequence, then dried over Na$_2$SO$_4$, filtered and evaporated to give the crude which was purified by chromatography (silica gel, PE to DCM) to afford 4-(bromomethyl)-N,N-bis(4-methoxybenzyl)benzenesulfonamide (5.6 g, 75%) as a white solid. $^1$H NMR (500 MHz, DMSO-d$_6$) δ 7.84 (d, J=8.3 Hz, 2H), 7.66 (d, J=8.3 Hz, 2H), 6.96 (d, J=8.5 Hz, 4H), 6.78 (d, J=8.6 Hz, 4H), 4.80 (s, 2H), 4.20 (s, 4H), 3.70 (s, 6H). ESI-MS (EI+, m/z):490 [M+H]+

Step 3: 4-((N-(imino(N-(imino(dimethylamino) methyl)amino)methyl)amino)methyl)-N,N-bis(4-methoxybenzyl)benzenesulfonamide To a solution of free metformin (2.8 g, 21.4 mmol) in DMF (15 mL) at 0° C. was added 4-(bromomethyl)-N,N-bis(4-methoxybenzyl)benzenesulfonamide (3.0 g, 6.2 mmol) in portions over 10 mins, the reaction mixture was then stirred at 0° C. for 3 h. The reaction mixture was poured into EtOAc (200 mL) and washed with H$_2$O (100 mL), brine (100 mL), dried over Na$_2$SO$_4$, filtered and evaporated to give the crude which was purified by prep-HPLC (C18, 0.05% TFA in H$_2$O/MeCN) to give 4-((N-(imino(N-(imino (dimethylamino) methyl) amino) methyl) amino)methyl)-N,N-bis(4-methoxybenzyl)benzenesulfonamide TFA salt (0.91 g, 23%) as a white solid. ESI-MS (EI+, m/z):539 [M+H]+, $^1$H NMR (400 MHz, DMSO-d$_6$) δ 7.83 (d, J=8.3 Hz, 2H), 7.53 (d, J=8.3 Hz, 2H), 7.49 (bs, 1H), 7.35 (bs, 2H), 6.97 (d, J=8.6 Hz, 4H), 6.78 (d, J=8.7 Hz, 4H), 6.70 (bs, 2H), 4.44 (d, J=5.9 Hz, 2H), 4.16 (s, 4H), 3.70 (s, 6H), 2.87 (s, 6H).

Step 4: 4-((N-(Imino(N-(imino(dimethylamino) methyl)amino)methyl)amino)methyl) benzenesulfonamide To a mixture of 4-((N-(imino (N-(imino (dimethylamino) methyl)amino) methyl)amino) methyl)-N,N-bis (4-methoxybenzyl) benzenesulfonamide TFA salt (400 mg, 0.74 mmol) and anisole (0.8 mL) was added TFA (8 mL) at 0° C. The reaction mixture was stirred at 20° C. for 3 h. The reaction mixture was evaporated and washed with MTBE (50 mL×3) to afford crude 4-((N-(imino(N-(imino(dimethylamino)methyl)amino) methyl)amino)methyl)benzenesulfonamide TFA salt (300 mg, 99%) as a tan solid. ESI-MS (EI+, m/z): 299 [M+H]+

Step 5: 7-Demethoxy-7-[4-4((N-(imino(N-(imino (dimethylamino)methyl)amino)methyl) amino) methyl) benzenesulfonamido]rapamycin To a solution of rapamycin (220 mg, 0.30 mmol) and 4-((N-(imino(N-(imino(dimethylamino)methyl)amino) methyl)amino)methyl)benzenesulfonamide TFA salt (300 mg, 0.74 mmol) in dry DCM (16 mL) was added TFA (1.2 ml) at −40° C. under N$_2$, the resultant solution was stirred at −40 to −30° C. for 2 h. The resulting mixture was added to cold EtOAc (200 ml), sat KHCO$_3$ (100 mL) was added and separated, the EtOAc phase was washed with H$_2$O (100 ml) then brine (100 ml), dried and evaporated to give the crude product which was purified by prep-HPLC (0.05% TFA in H$_2$O/MeCN) to give 7-Demethoxy-7-[4-((N-(imino(N-

(imino (dimethylamino)methyl)amino)methyl)amino)methyl)benzenesulfonamido]rapamycin (18 mg, 5%) as a white solid. MS (EI+, m/z): 1181 [M+H]+. $^1$H NMR (500 MHz, MeOD) δ 7.82-7.68 (m, 2H), 7.52-7.39 (m, 2H), 6.24-6.04 (m, 3.0H), 5.97-5.78 (m, 0.7H), 5.71-5.44 (m, 0.8H), 5.34 (d, J=11.0 Hz, 0.5H), 5.23-5.05 (m, 2H), 4.94 (dd, J=5.0, 3.1 Hz, 1H), 4.54-4.44 (m, 2H), 4.18 (d, J=19.4 Hz, 1.5H), 3.94 (d, J=5.5 Hz, 1H), 3.87 (d, J=5.8 Hz, 0.6H), 3.70-3.63 (m, 0.4H), 3.52 (s, 0.5H), 3.43 (d, J=11.1 Hz, 3H), 3.37 (s, 0.5H), 3.32-3.28 (m, 5.5H), 3.01 (s, 6H), 2.99-2.93 (m, 1.5H), 2.85 (dd, J=35.2, 15.8 Hz, 0.5H), 2.71 (s, 1H), 2.56-2.44 (m, 0.5H), 2.37-2.21 (m, 1.5H), 2.21-2.06 (m, 2H), 2.01 (dd, J=15.6, 7.4 Hz, 0.5H), 1.93 (dd, J=15.5, 8.6 Hz, 1.5H), 1.79 (d, J=15.5 Hz, 7H), 1.60 (ddd, J=71.4, 42.6, 15.6 Hz, 9H), 1.42-1.28 (m, 6H), 1.24 (d, J=11.4 Hz, 2H), 1.15-1.10 (m, 1.5H), 1.08 (d, J=6.6 Hz, 3.5H), 1.04-0.97 (m, 5.5H), 0.95-0.84 (m, 7H), 0.79-0.64 (m, 1.5H).

Example 5. Synthesis of 1-3-[(1R,9S,12S,15R,16E, 18R,19R,21R,23S,24E,26E,28E,32S,35R)-1,18-dihydroxy-12-[(2R)-1-[(1S,3R,4R)-4-hydroxy-3-methoxycyclohexyl]propan-2-yl]-19-methoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-30-yl]carbamimidamido-N,N-dimethylmethanimidamide, I-55

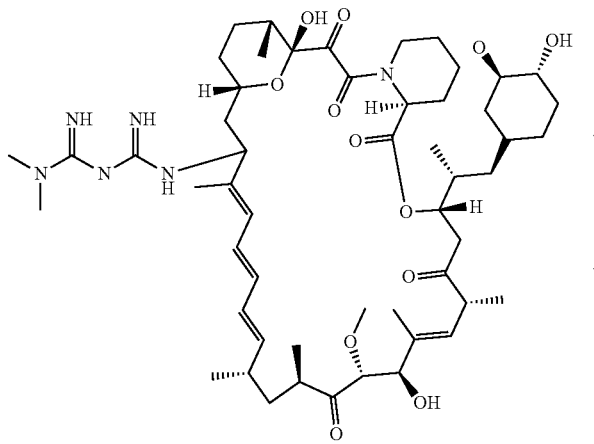

Synthetic Scheme:

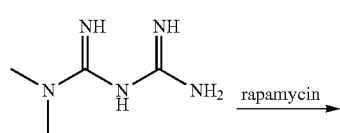

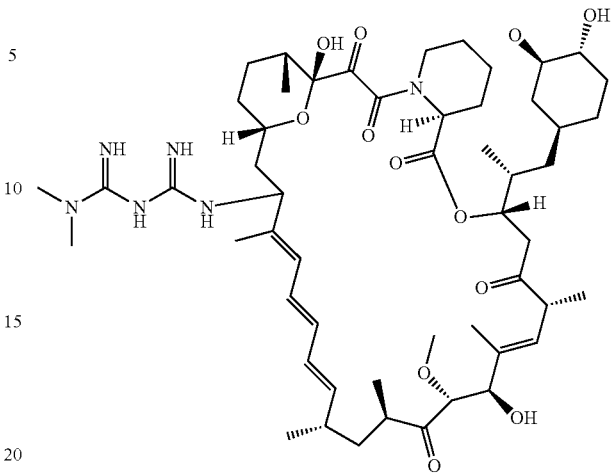

Step 1: Free Metformin

To solution of metformin hydrochloride in 20 ml of water, 6 ml of 1M NaOH was added. The suspension was stirred overnight at rt. The water was evaporated under reduced pressure to dryness, the obtained precipitate was dissolved in 20 ml of methanol. The resulting precipitate was filtered off and the filtrate concentrated under reduced pressure to give a pure compound (yield: 55%).

Step 2: 1-3-[(1R,9S,12S,15R,16E,18R,19R,21R, 23S,24E,26E,28E,32S,35R)-1,18-dihydroxy-12-[(2R)-1-[(1S,3R,4R)-4-hydroxy-3-methoxycyclohexyl]propan-2-yl]-19-methoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-30-yl]carbamimidamido-N,N-dimethylmethanimidamide To a solution of rapamycin in dry DCM (25 ml), p-toluenesulfonic acid monohydrate was added at rt under an argon atmosphere. The solution was stirred for 10 min followed by the addition of metformin in one portion and stirred for 2 h. The reaction mixture was quenched with sat. NaHCO$_3$ solution and extracted with EtOAc:water. The organic layer was additionally washed with brine and dried over MgSO$_4$, filtered and concentrated under reduced pressure. The mixture was purified by SFC to give 20 mg (Yield: 5.5%). The compound was used as is.

We claim:

1. A compound of formula I:

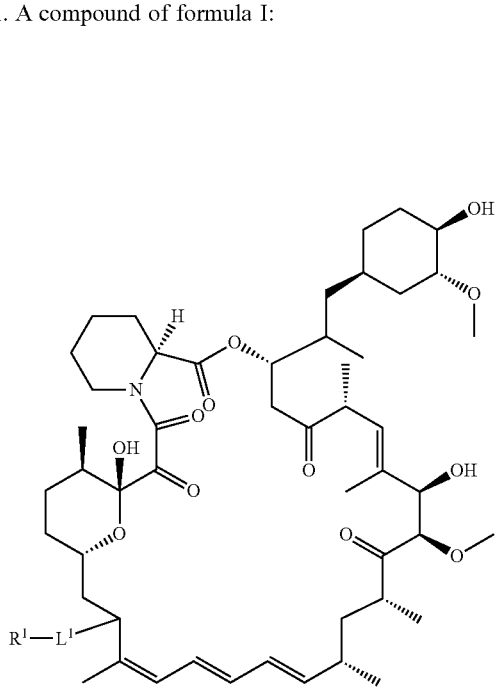

or a pharmaceutically acceptable salt thereof, wherein:

$L^1$ is a covalent bond or an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, S(O)$_2$—, or -Cy-;

each R is independently hydrogen, or an optionally substituted group selected from $C_{1-6}$ aliphatic, phenyl, 4-7 membered saturated or partially unsaturated heterocyclic having 1-2 heteroatoms independently selected from nitrogen, oxygen, or sulfur, or 5-6 membered heteroaryl ring having 1-4 heteroatoms independently selected from nitrogen, oxygen, or sulfur, each -Cy- is independently an optionally substituted bivalent ring selected from 3-7 membered saturated or partially unsaturated monocyclic or bicyclic carbocyclylene, monocyclic or bicyclic arylene, 4-10 membered saturated or partially unsaturated monocyclic or bicyclic heterocyclylene having 1-3 heteroatoms independently selected from nitrogen, oxygen, or sulfur, or 5-10 membered saturated or partially unsaturated monocyclic or bicyclic heteroarylene having 1-3 heteroatoms independently selected from nitrogen, oxygen, or sulfur;

and $R^1$ is a monovalent derivative of a therapeutic agent.

2. The compound according to claim 1, wherein said compound is of formula I-a:

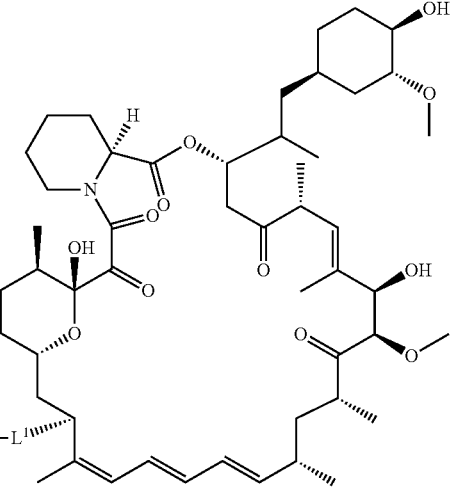

or a pharmaceutically acceptable salt thereof.

3. The compound according to claim 1, wherein said compound is of formula I-b:

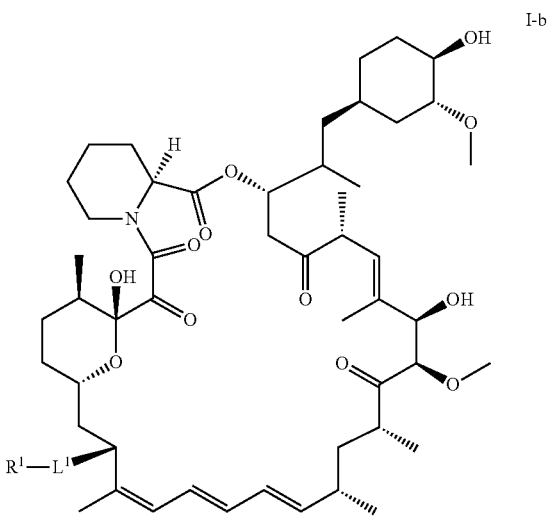

or a pharmaceutically acceptable salt thereof.

4. The compound according to any one of claims 1 through 3, wherein $L^1$ is a covalent bond.

5. The compound according to any one of claims 1 through 3, wherein $L^1$ is an optionally substituted straight or branched saturated or unsaturated bivalent hydrocarbon chain wherein one or more methylene units of $L^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or -Cy-.

6. The compound according to any one of claims 1 through 3, wherein the therapeutic agent is a monovalent inhibitor of mTORC1 and/or mTORC2, or a monovalent inhibitor of 4E-BP1 and/or ULK1.

7. The compound according to any one of claims 1 through 3, wherein the therapeutic agent is a monovalent inhibitor of a protein kinase.

8. The compound according to claim 7, wherein the protein kinase is Akt, CDK4, CDK6, EGFR, HER2, and/or AMPK.

9. The compound according to any one of claims 1 through 3, wherein the therapeutic agent is a monovalent inhibitor of BCR-Abl or BCL-2.

10. The compound according to any one of claims 1 through 3, wherein the therapeutic agent is selected from a PPAR modulator or a DPP4 inhibitor.

11. The compound according to claim 10, wherein the therapeutic agent is Rosiglitazone, Pioglitazone, Sitagliptin or Vildagliptin.

12. The compound according to claim 1, wherein the therapeutic agent is selected from:

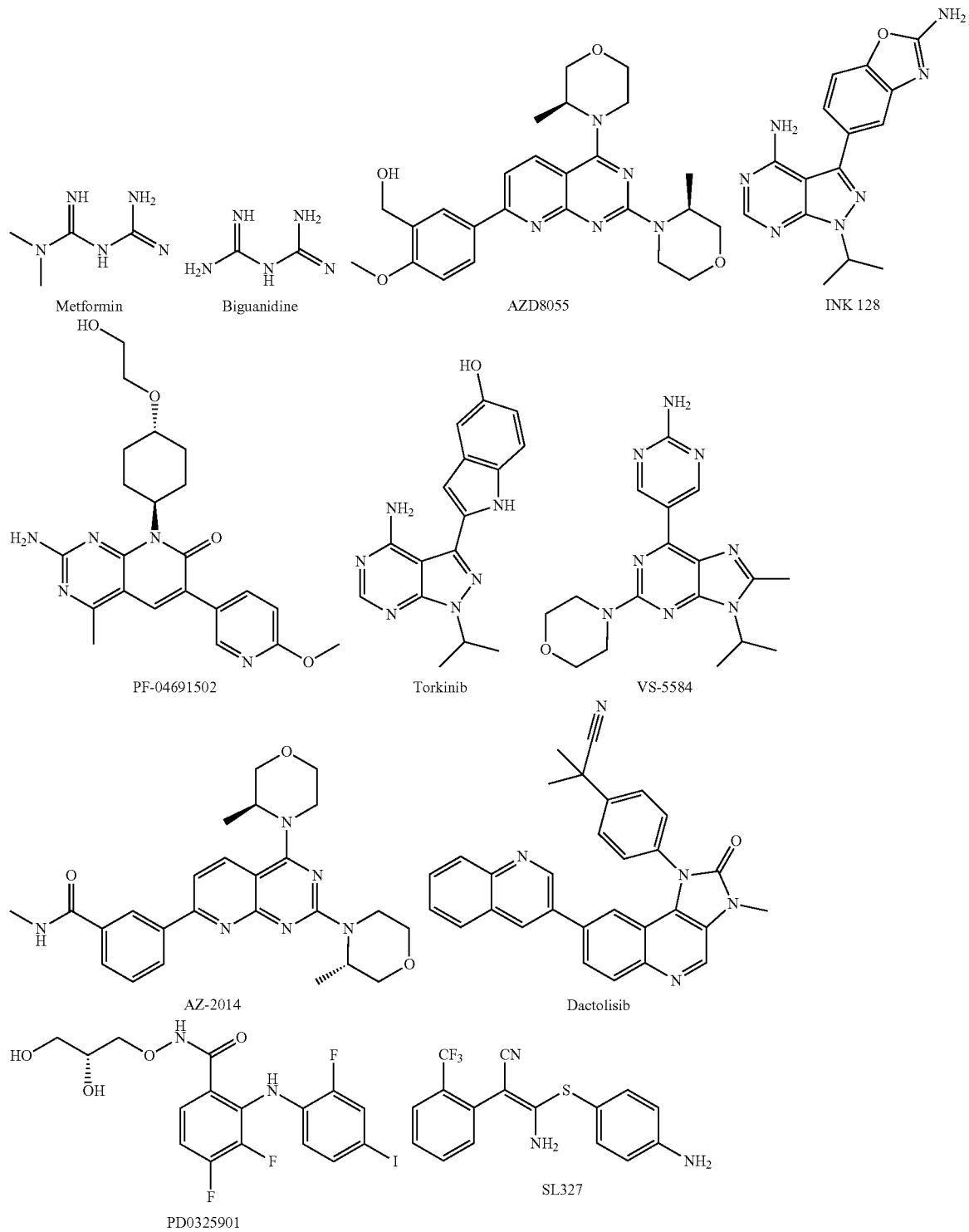

-continued
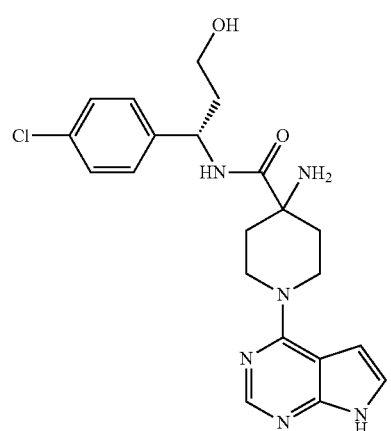
AZD5363
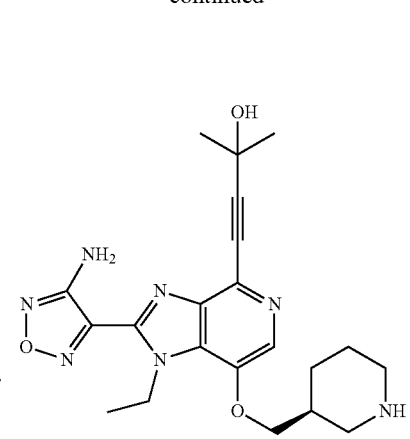
GSK690693
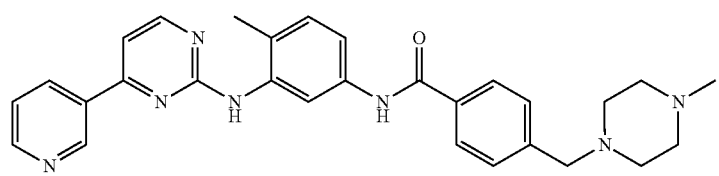
Imatinib
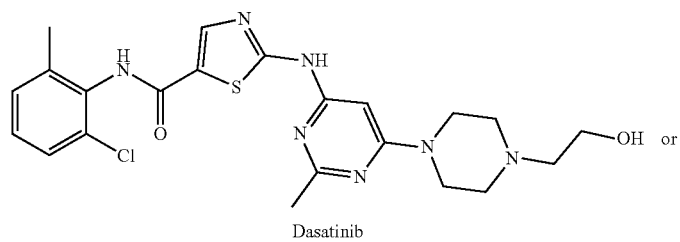
Dasatinib
or
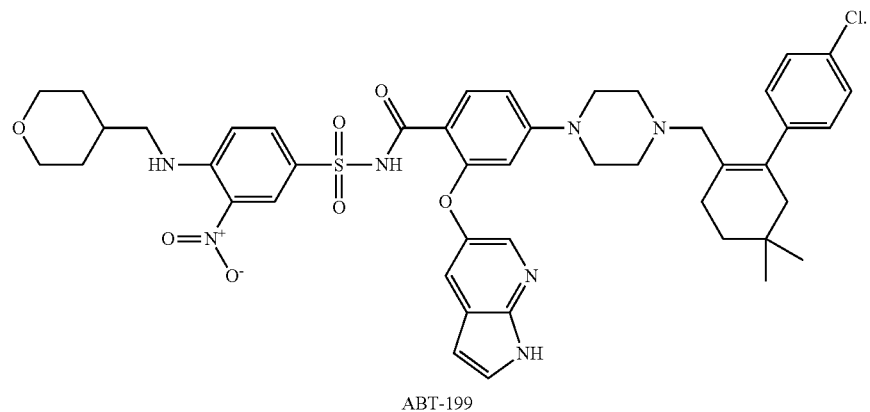
ABT-199

13. A compound selected from:
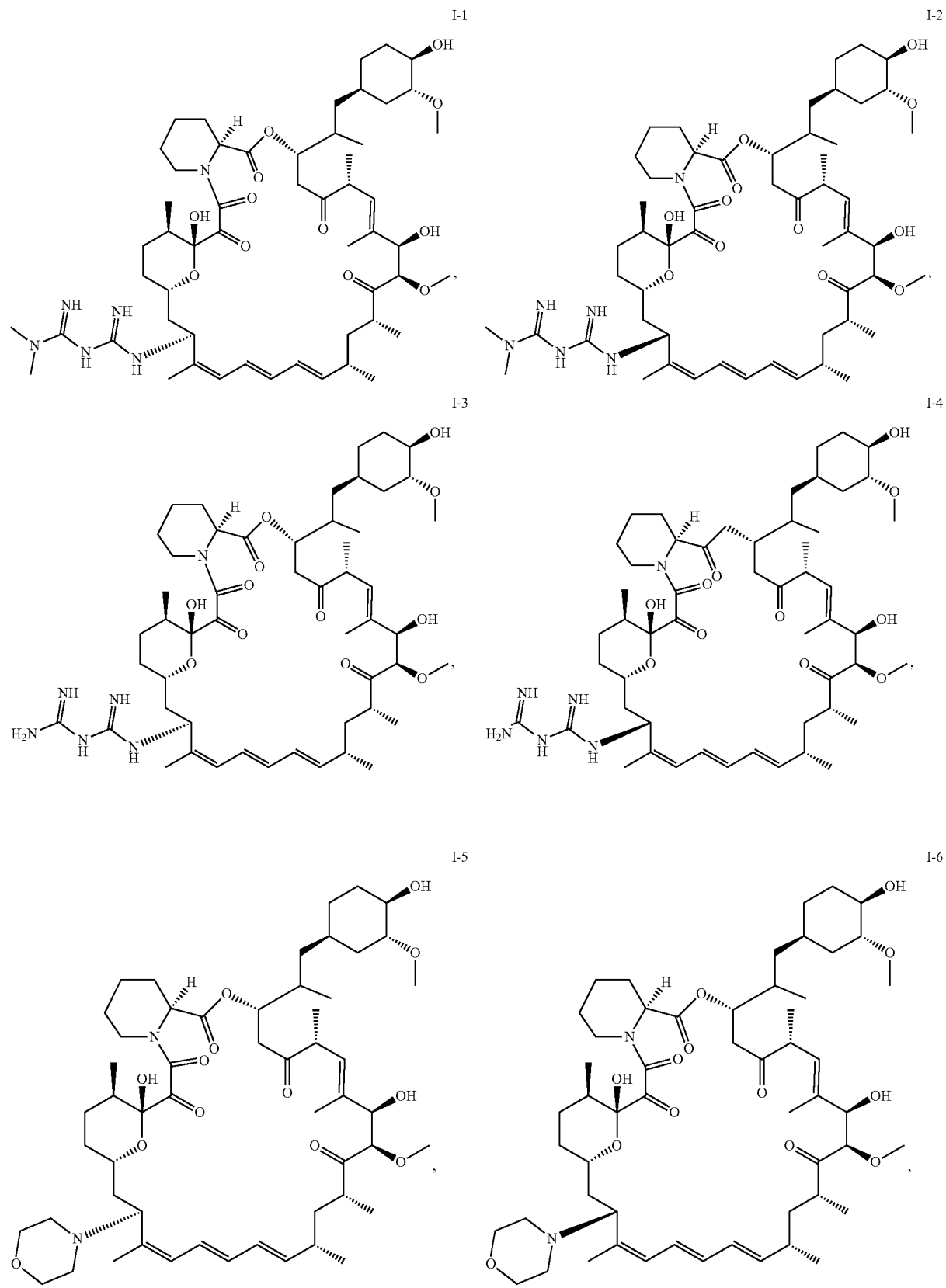

-continued
I-7
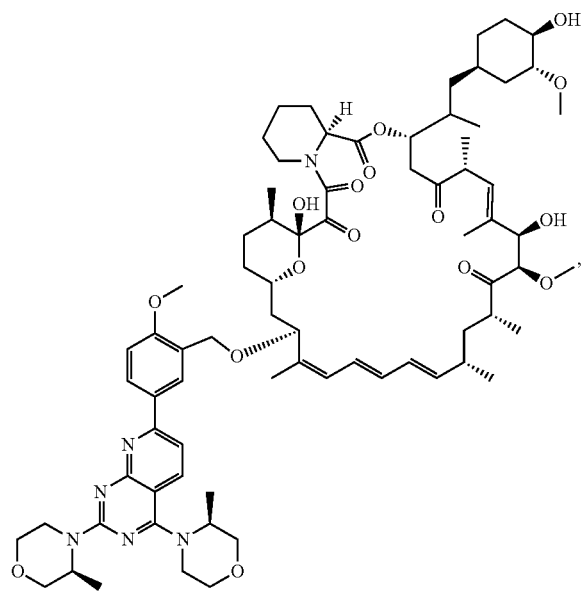
I-8
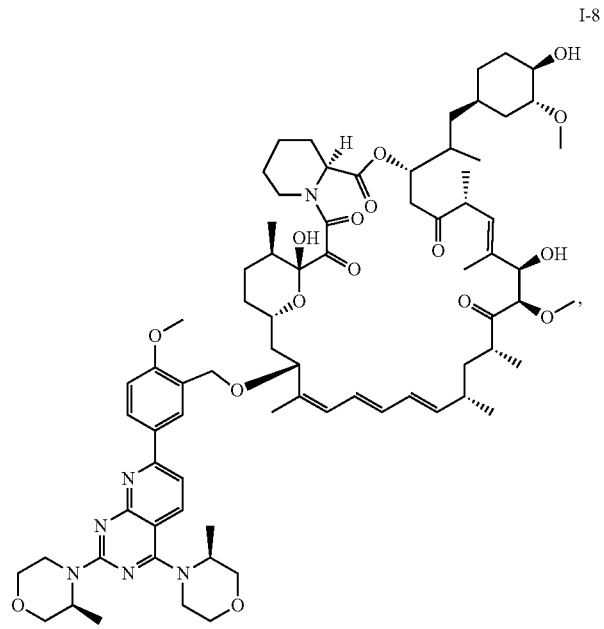
I-9
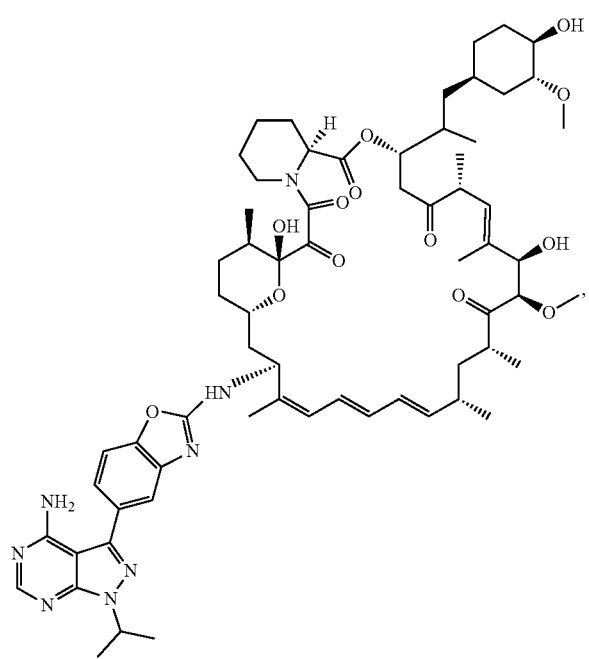
I-10
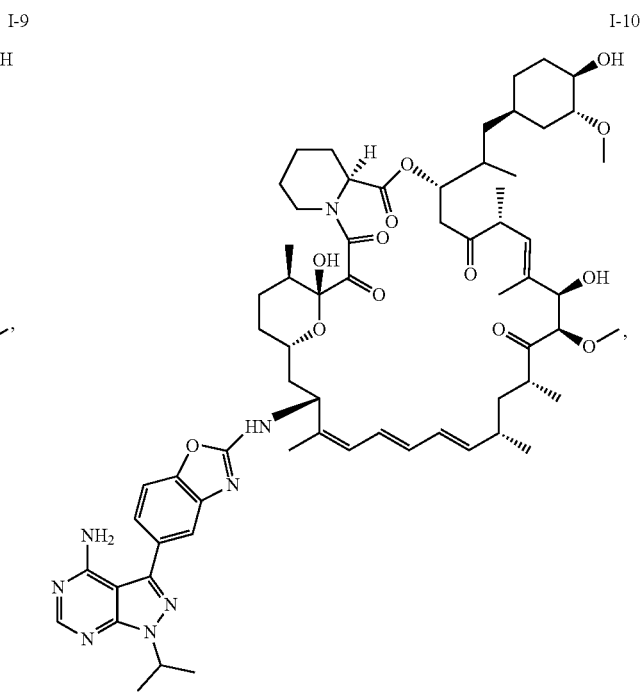

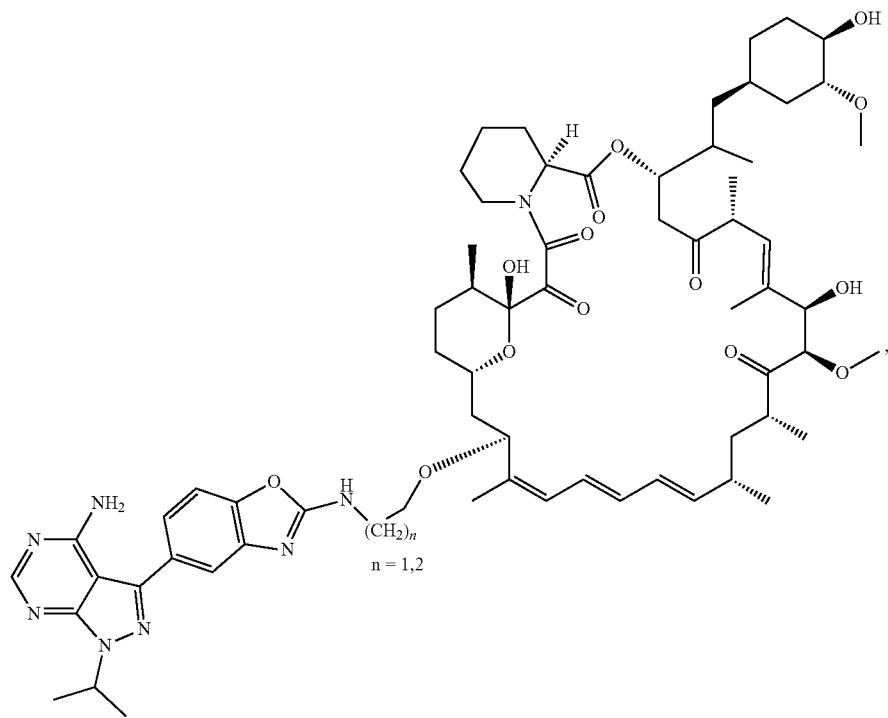
I-11
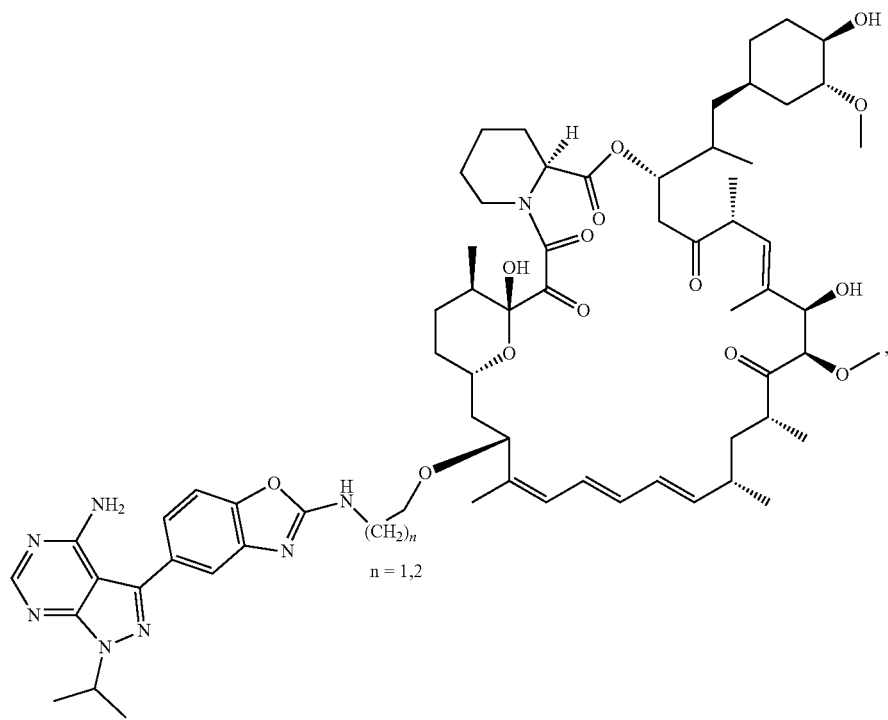
I-12

-continued
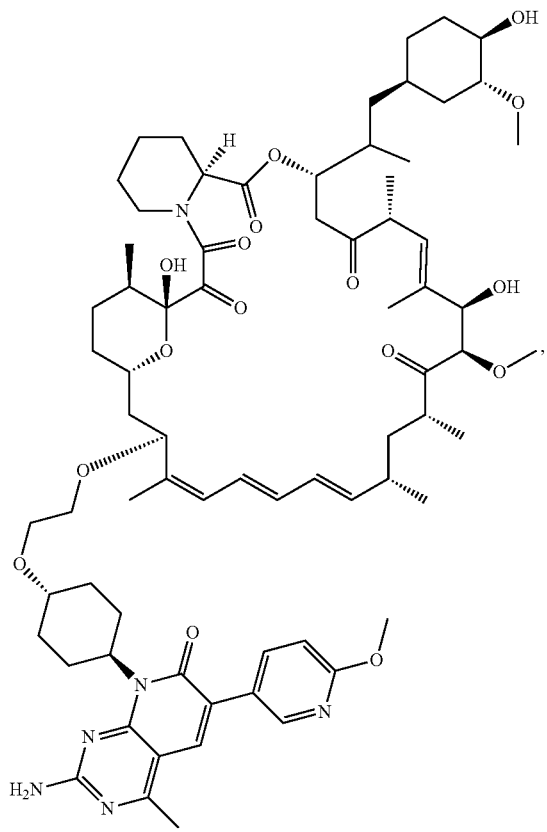
I-13
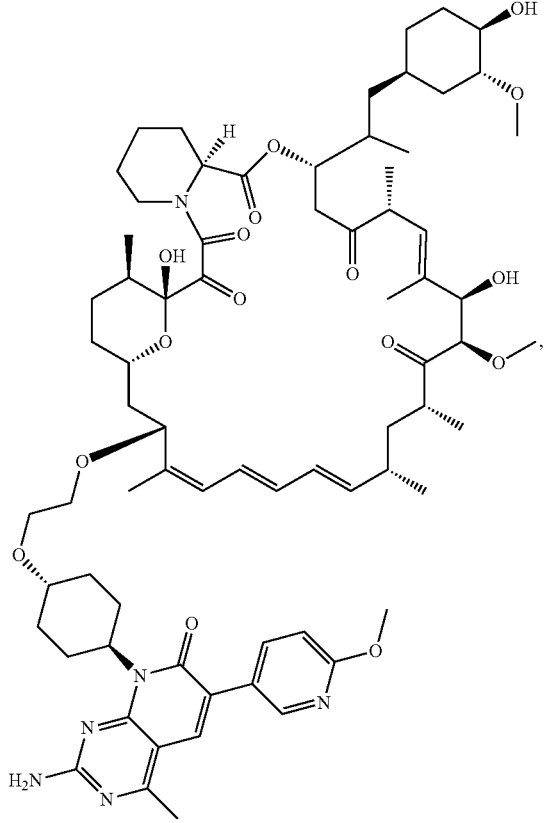
I-14
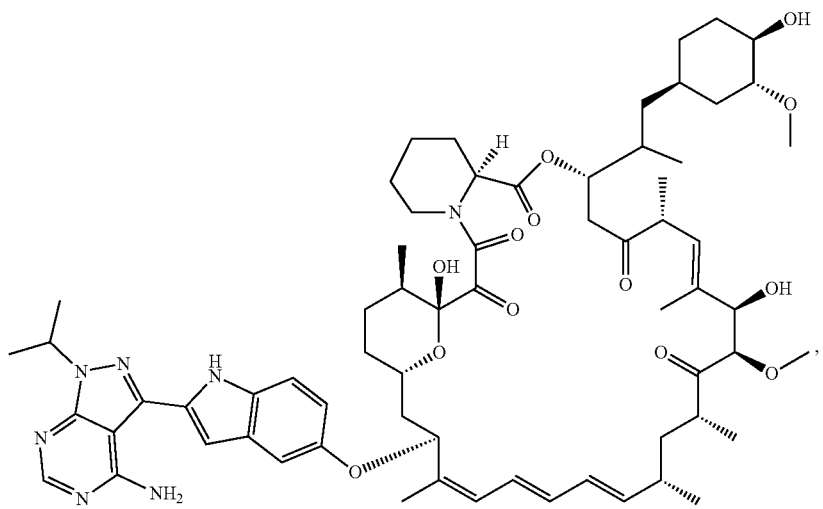
I-15

-continued
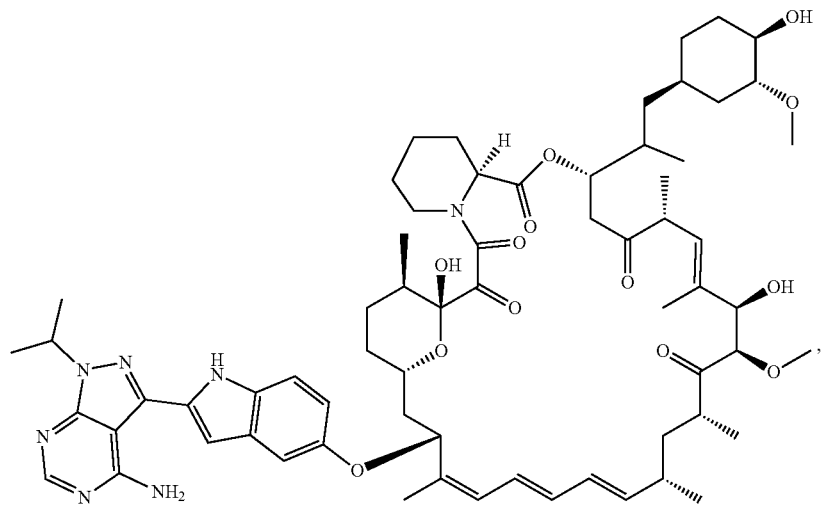
I-16
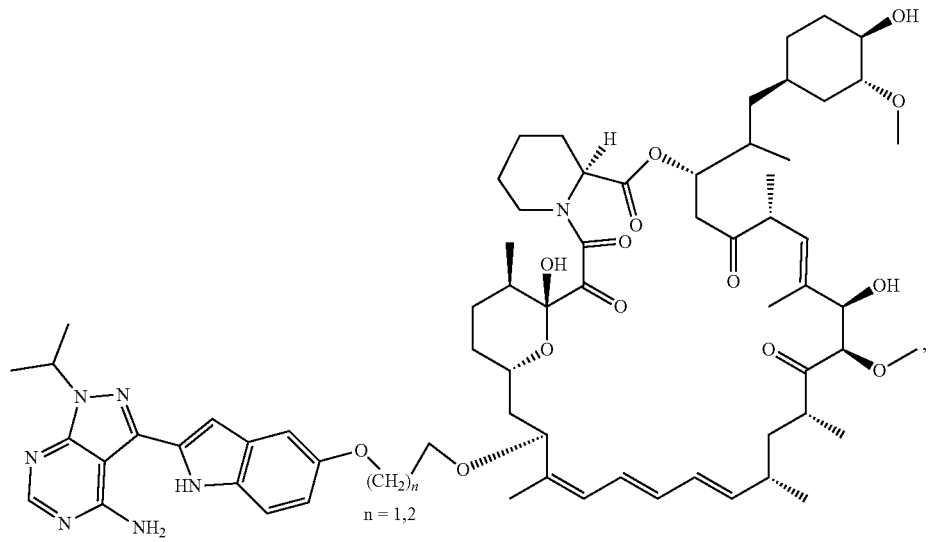
I-17
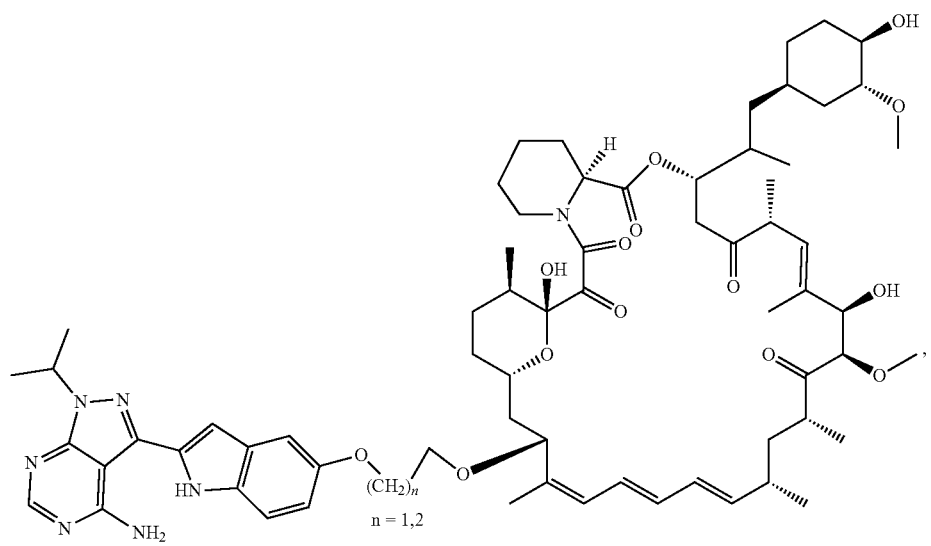
I-18

-continued
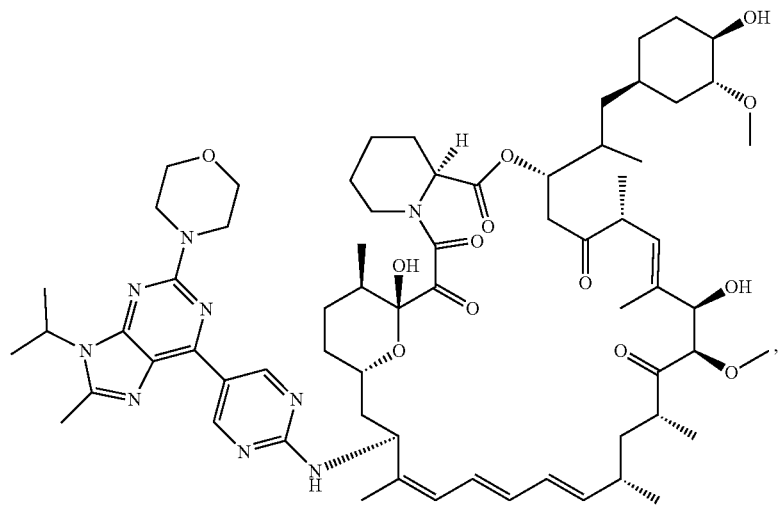
I-19
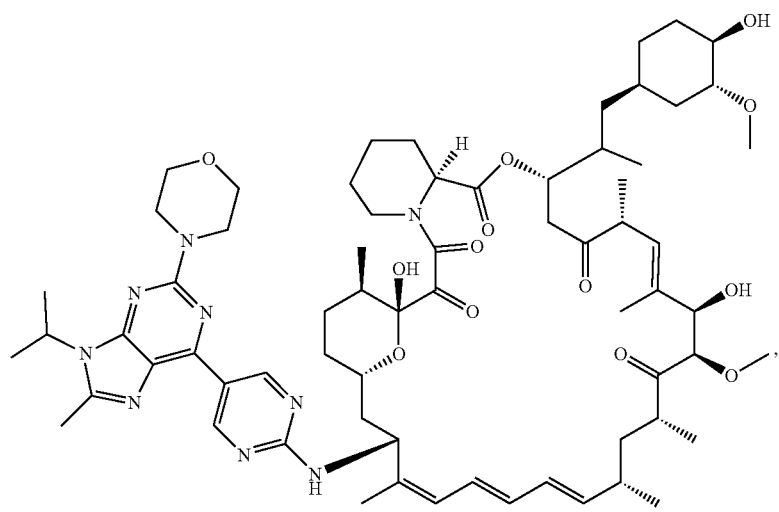
I-20
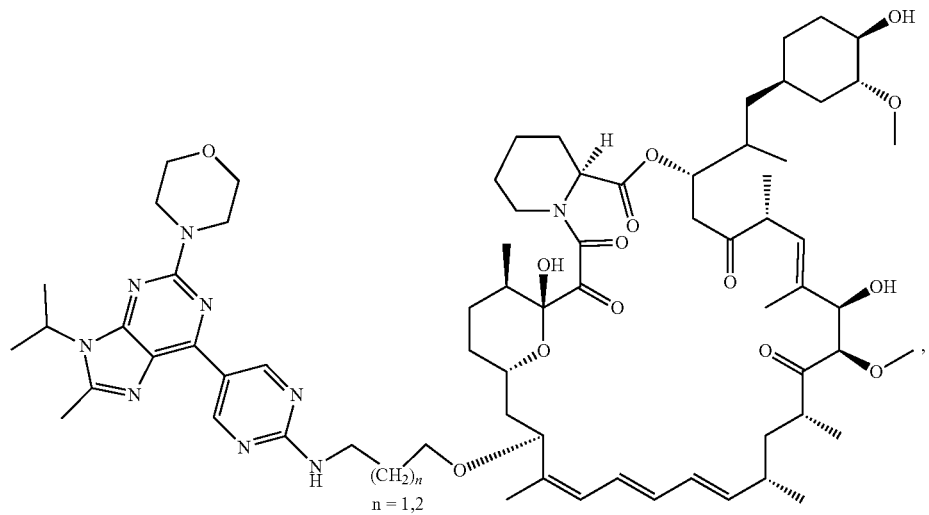
I-21

-continued
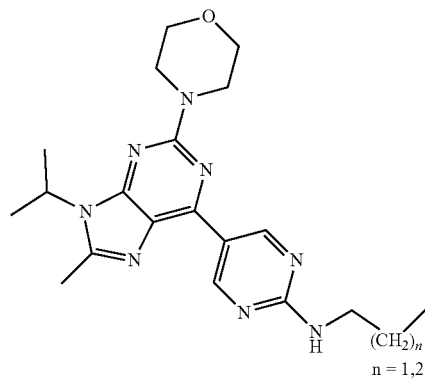
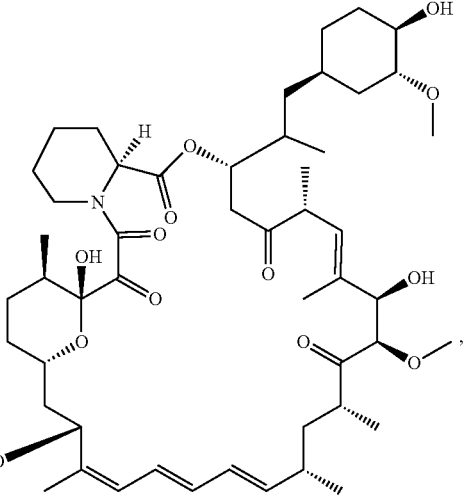
I-22
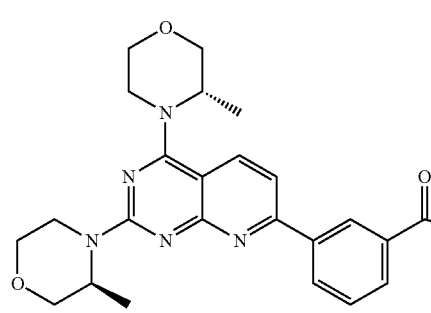
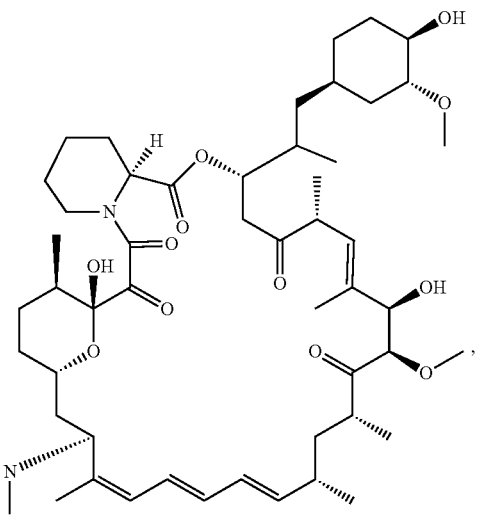
I-23
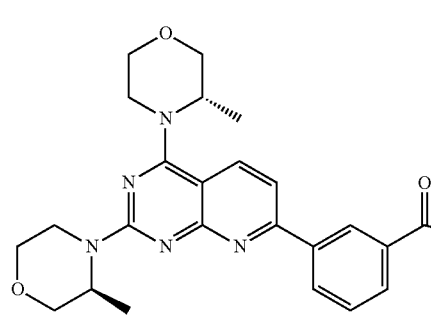
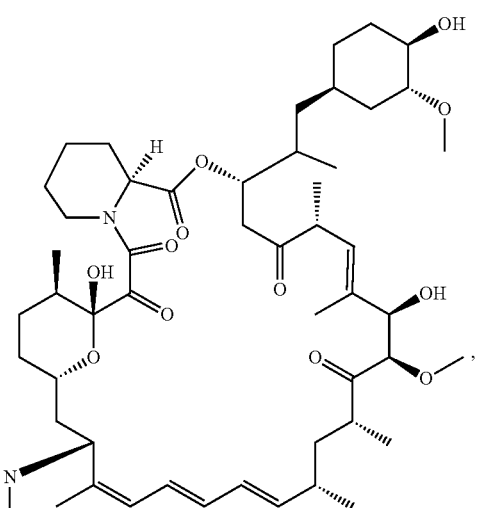
I-24

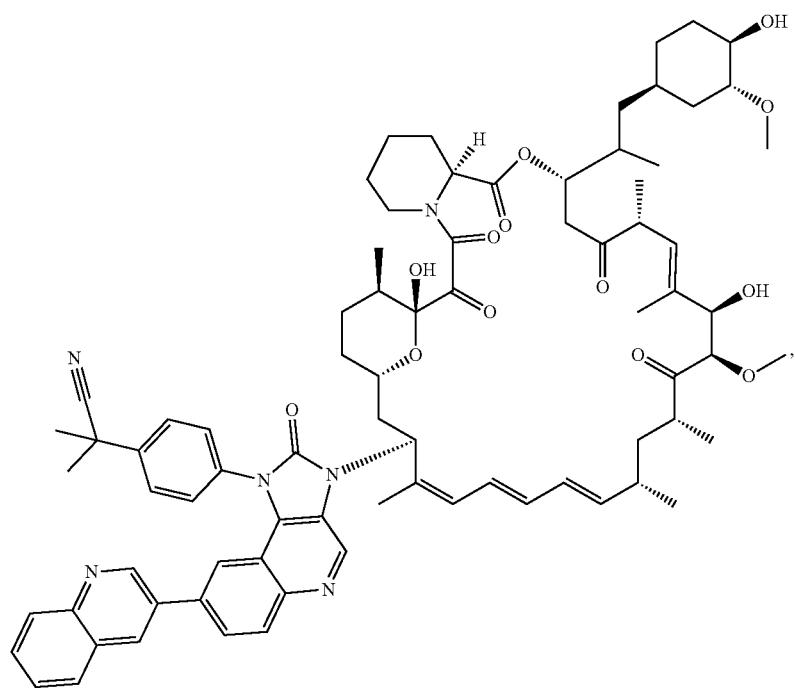
I-25
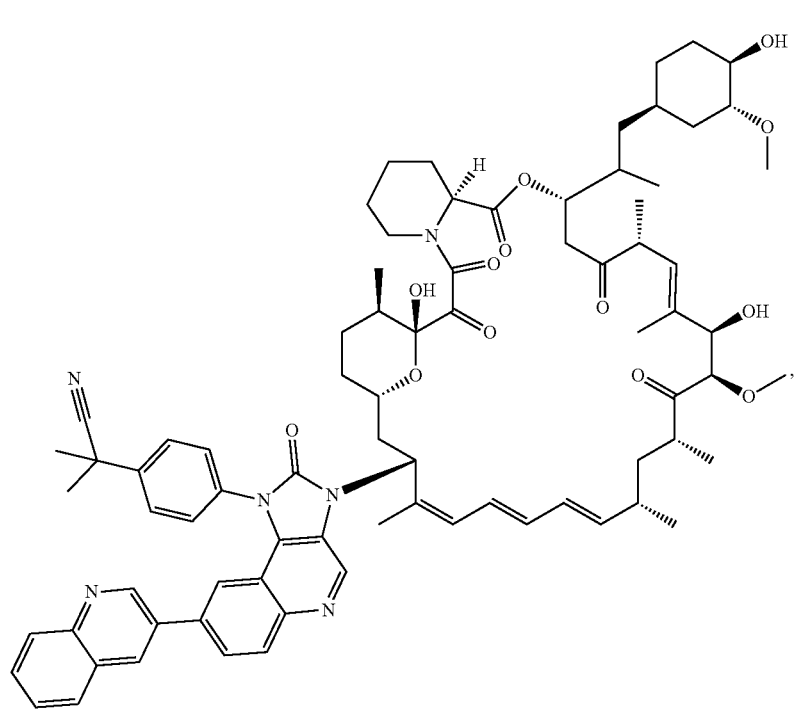
I-26

I-27
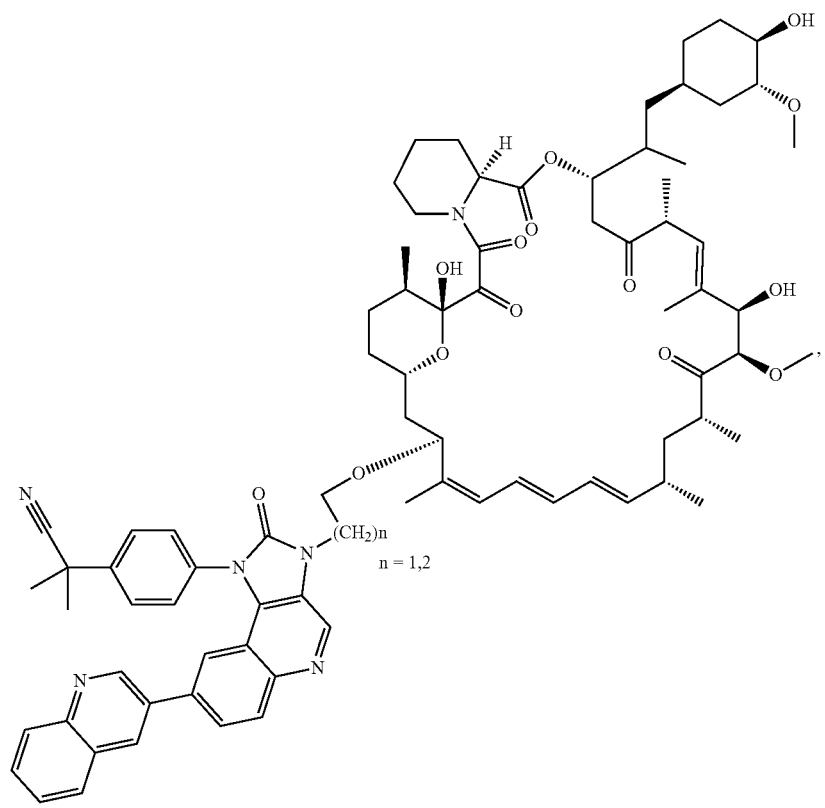
n = 1,2
I-28
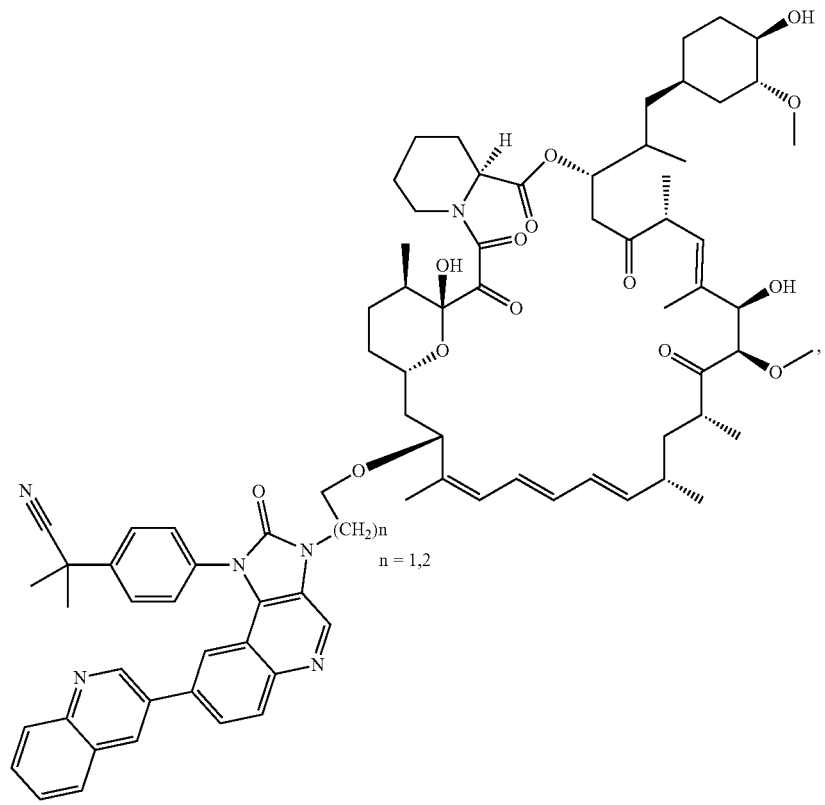
n = 1,2

I-29
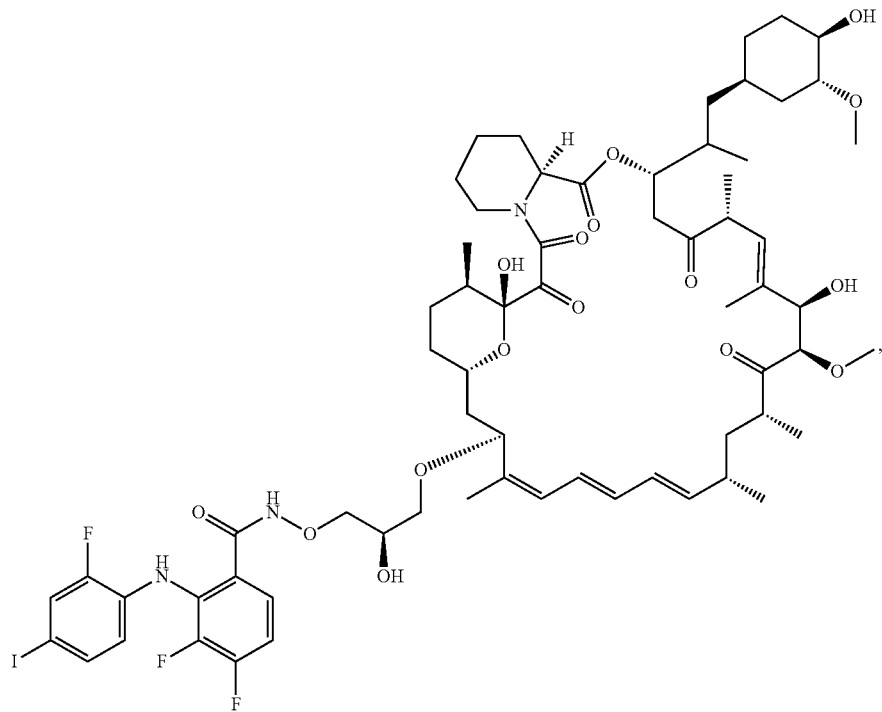
I-30
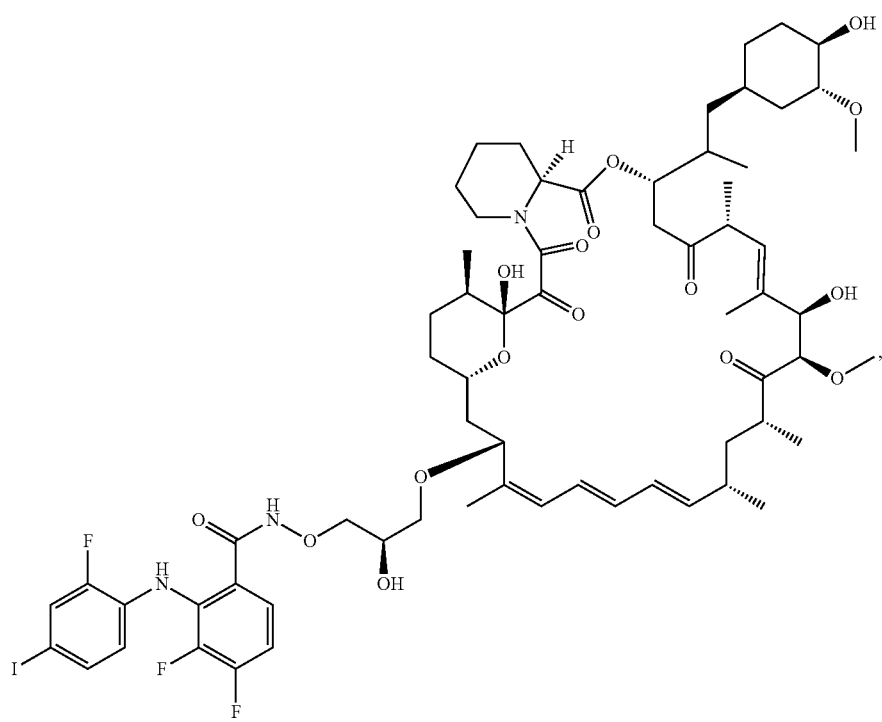

I-31
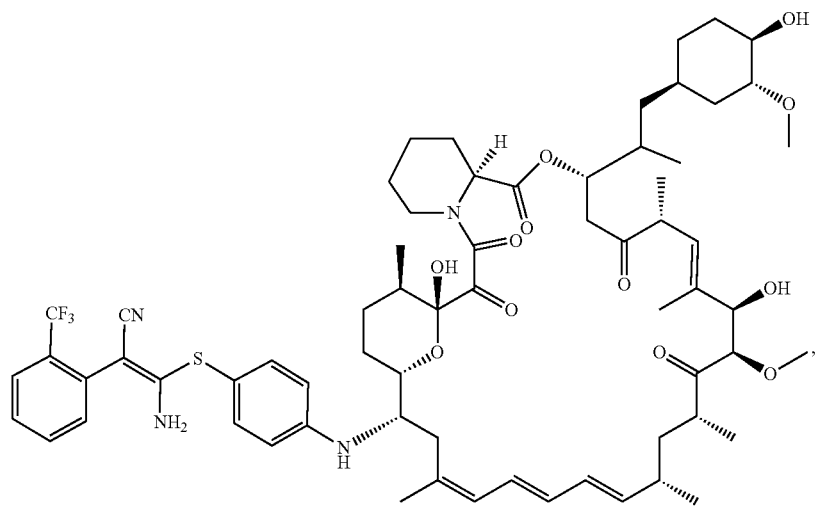
I-32
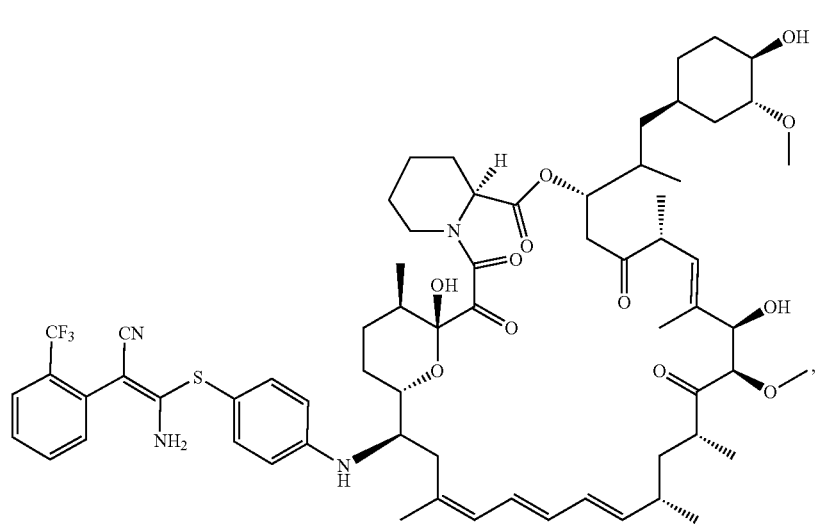
I-33
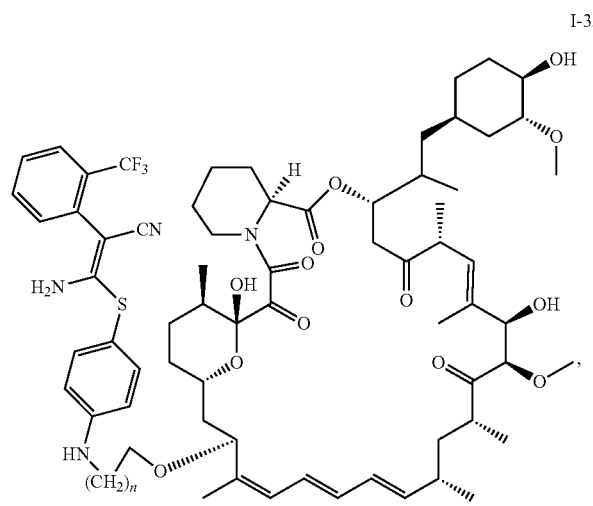
I-34
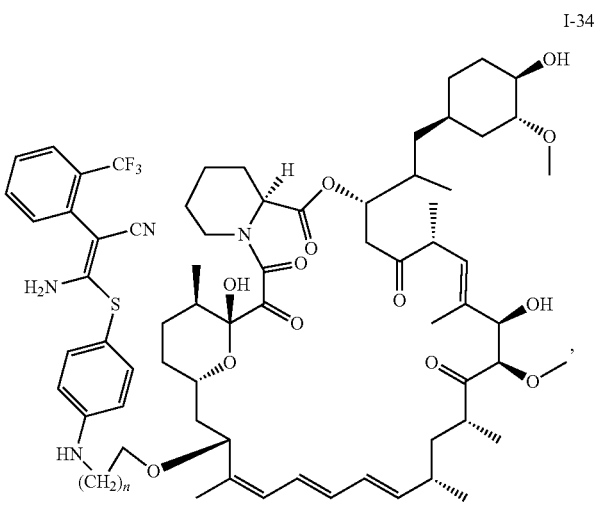

-continued
I-35
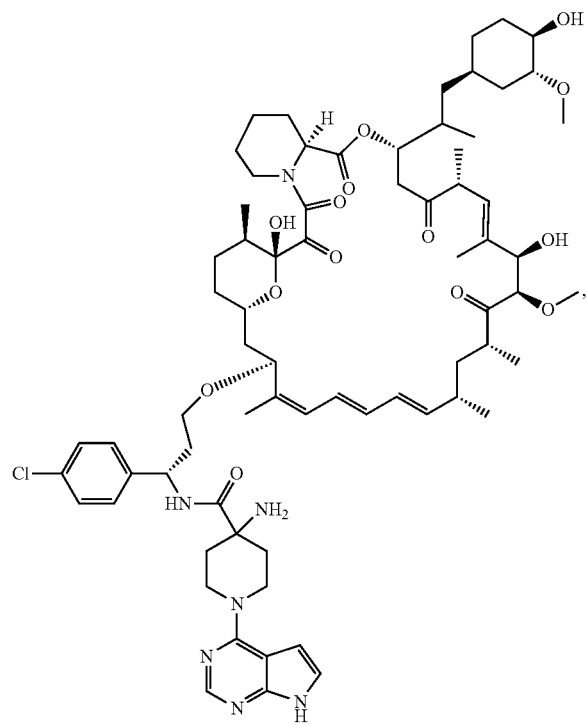
I-36
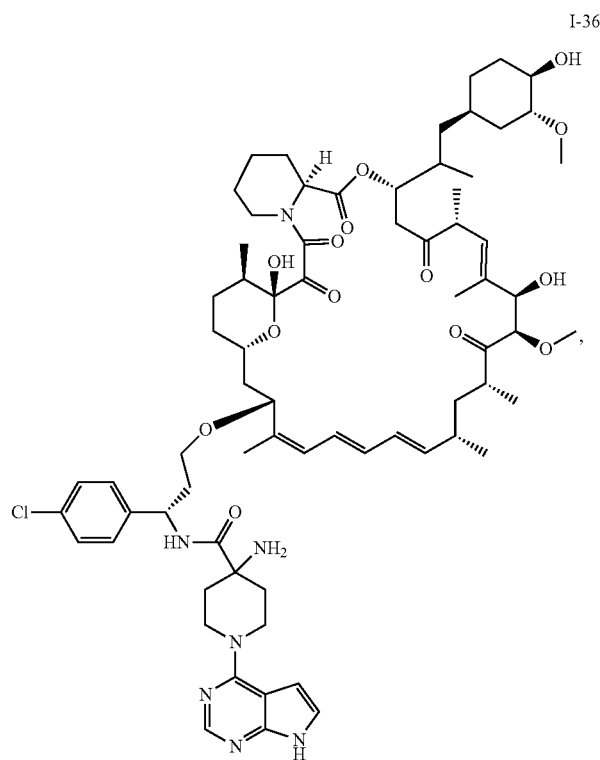
I-37
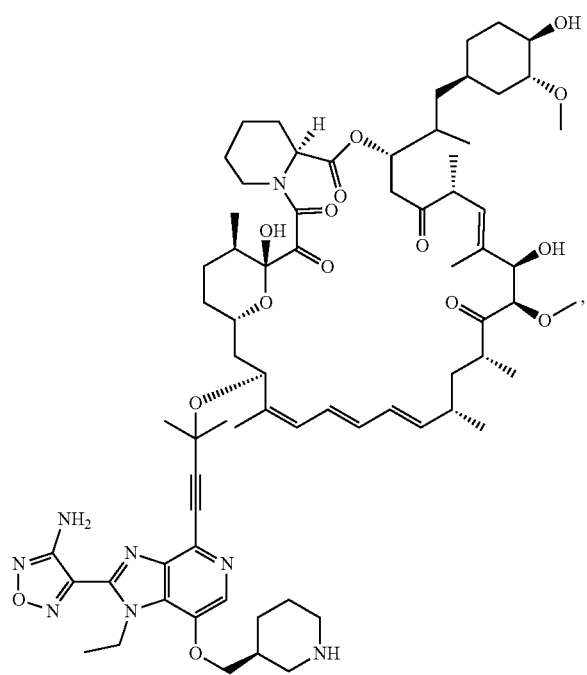
I-38
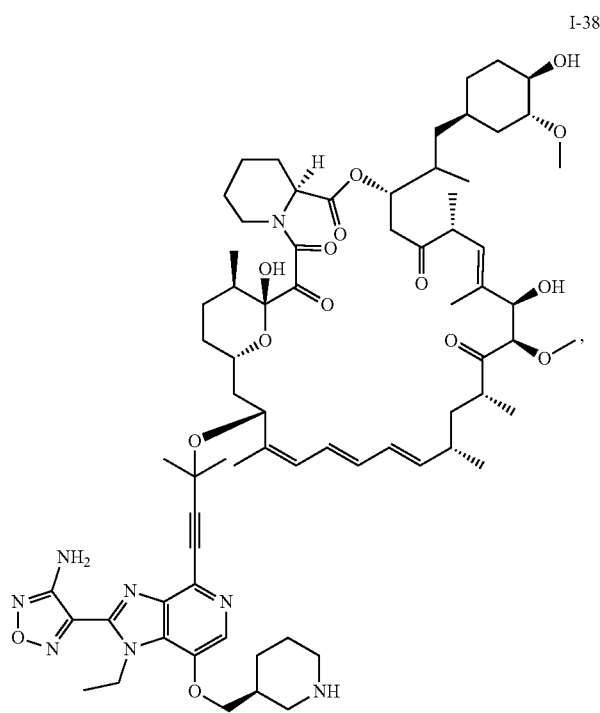

-continued
I-39
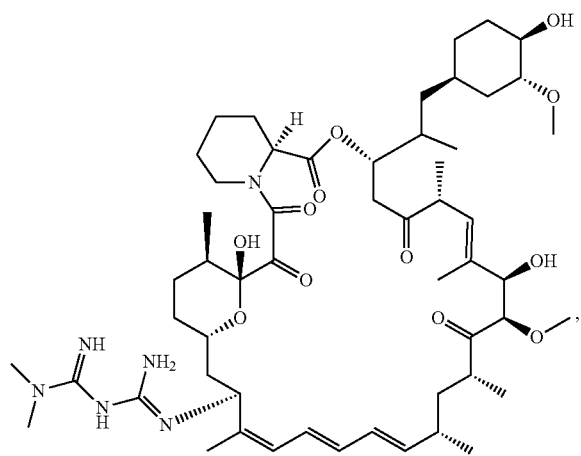
I-40
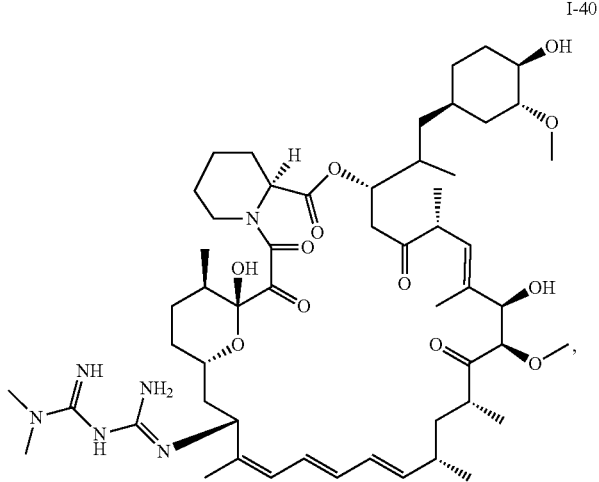
I-41
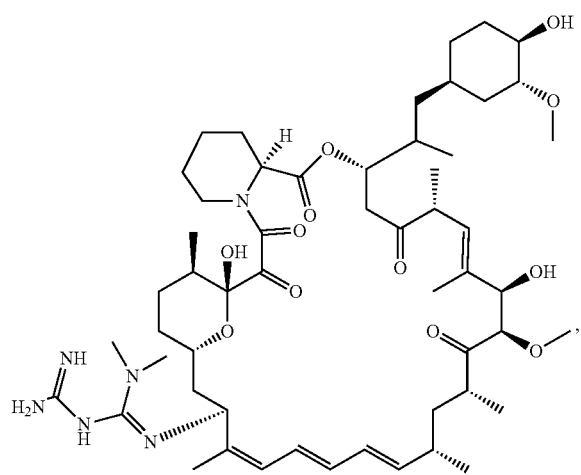
I-42
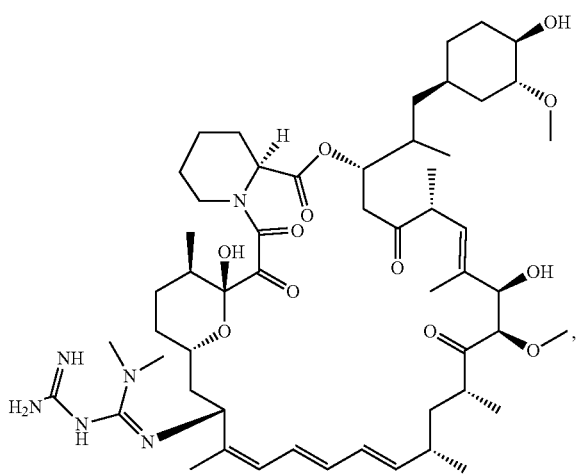
I-43
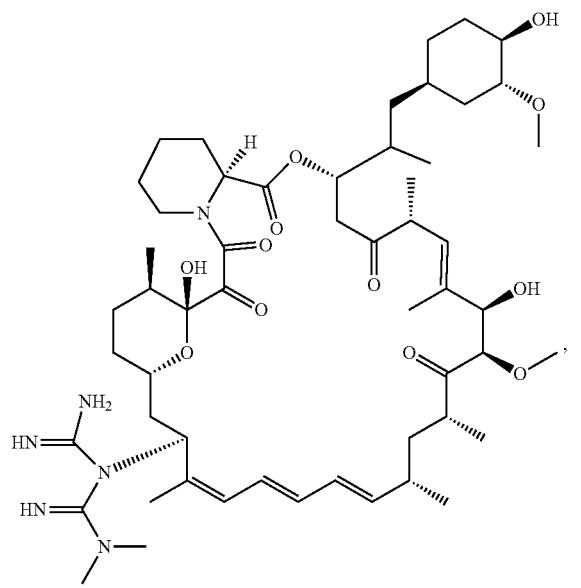
I-44
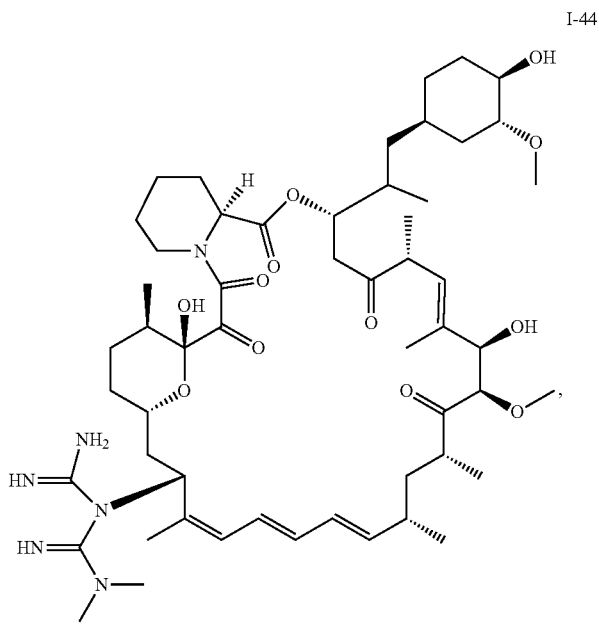

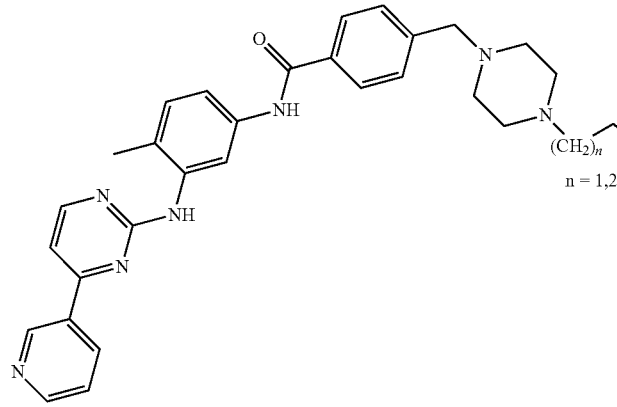
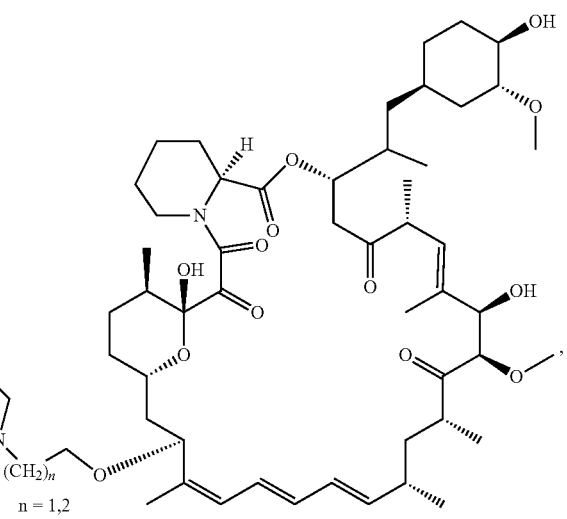
I-45
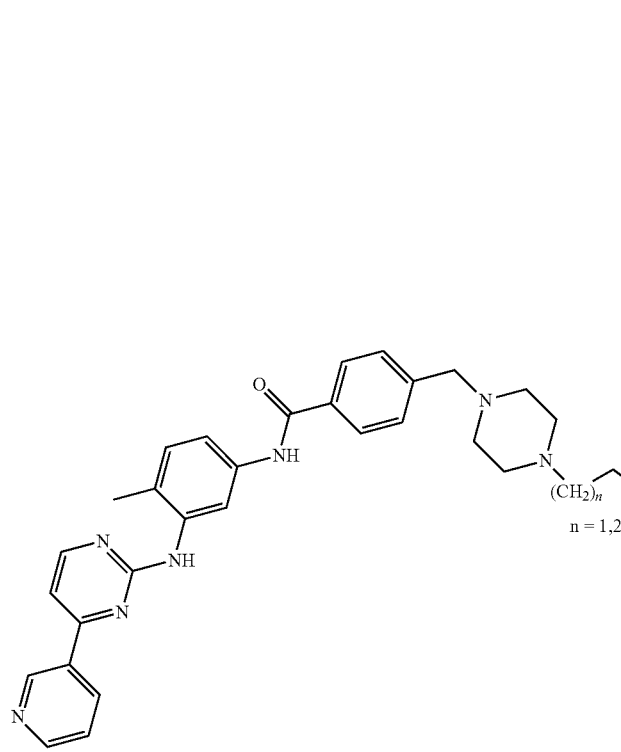
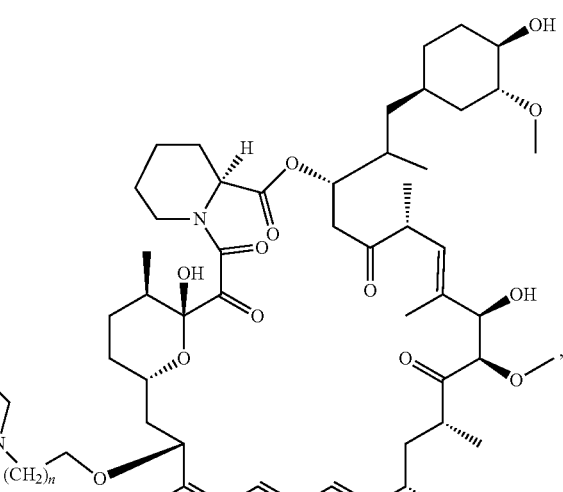
I-46

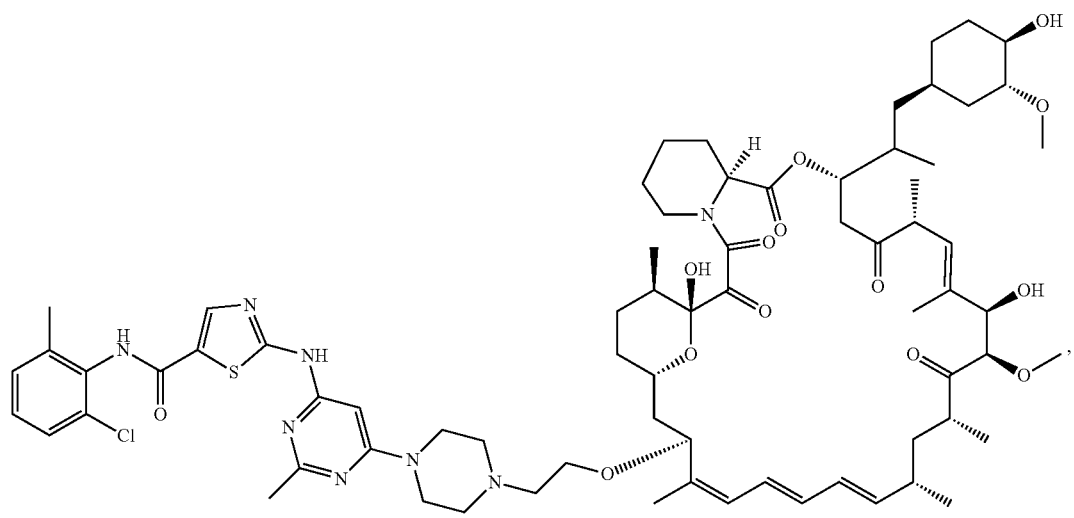
I-47
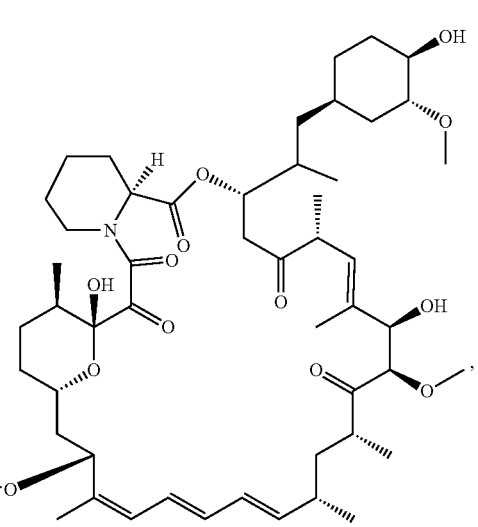
I-48

-continued
I-49
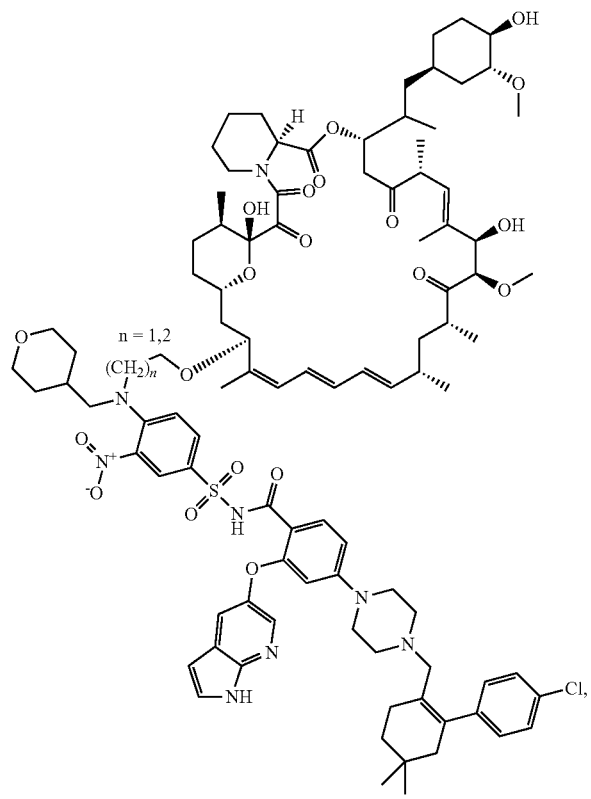
I-50
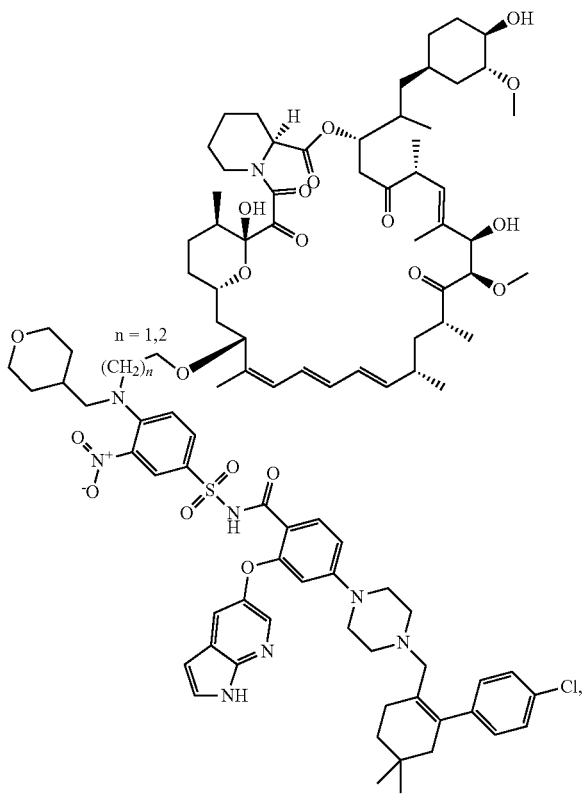
I-51
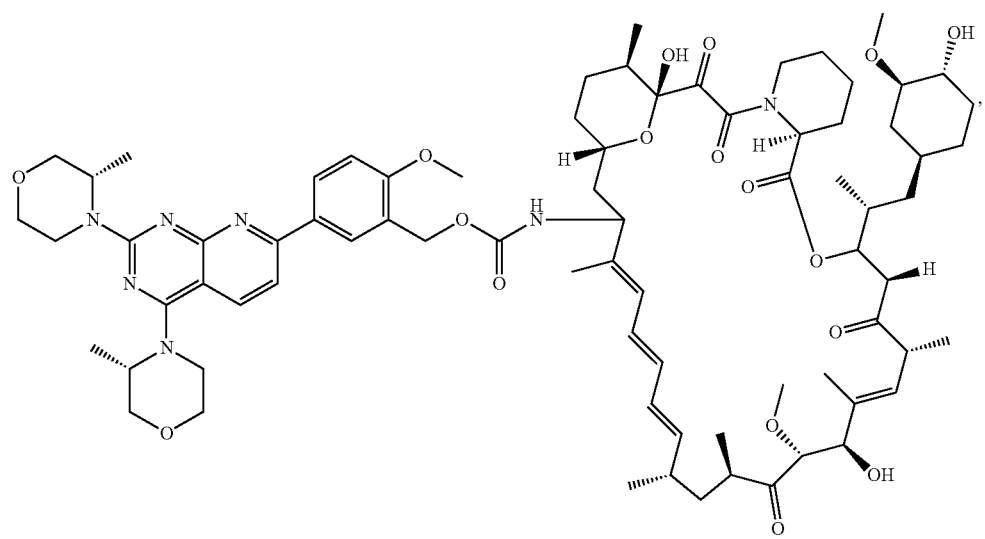

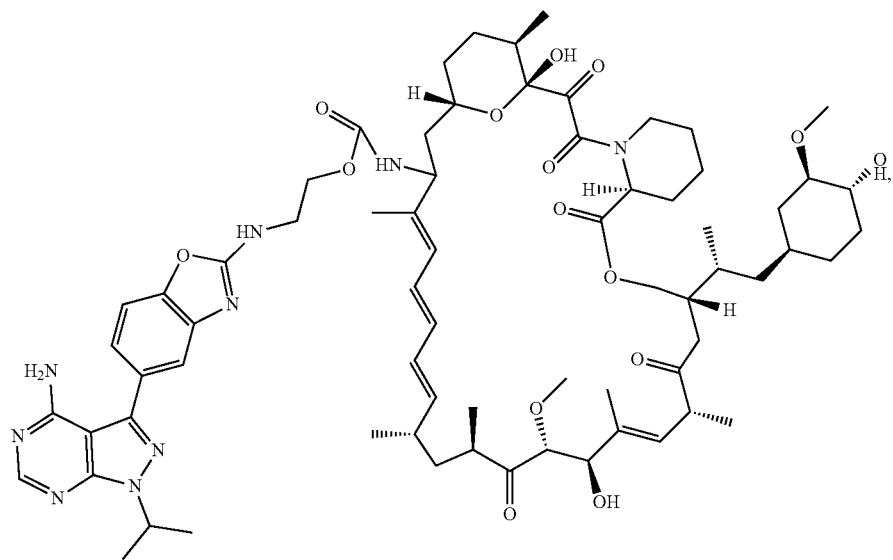
I-52
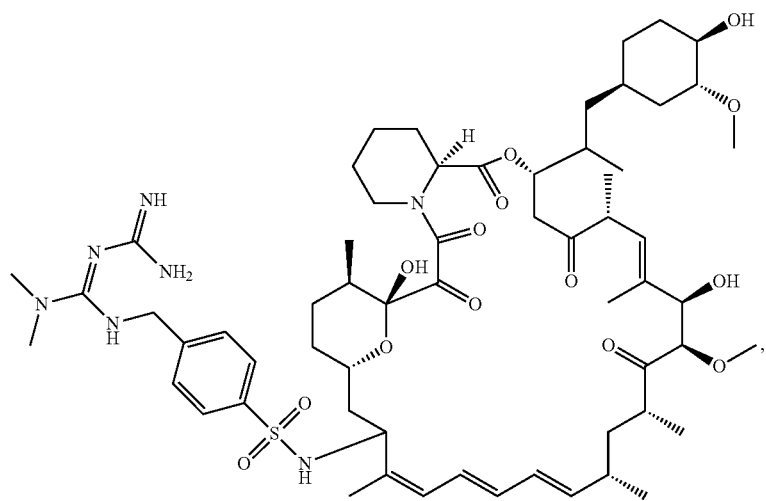
I-53
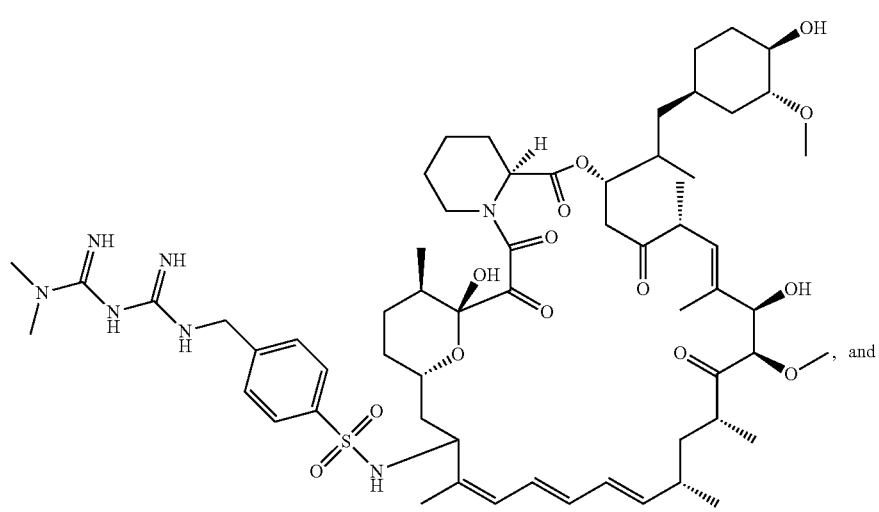
I-54

-continued
I-55
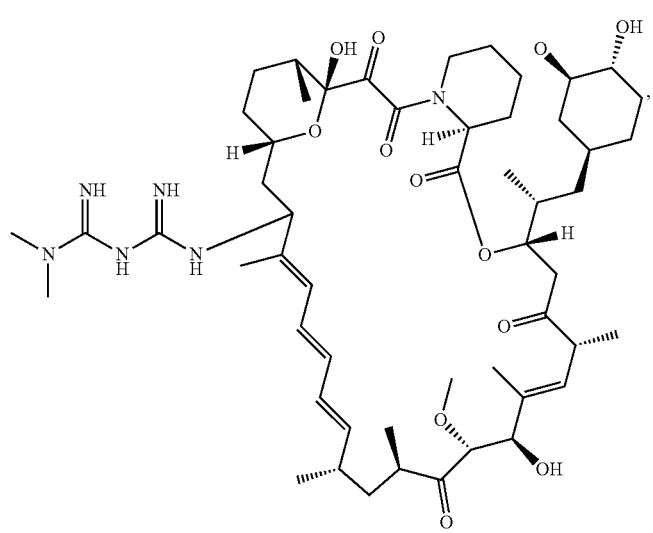
or a pharmaceutically acceptable salt thereof.
14. A pharmaceutically acceptable composition comprising the compound of any one of claims 1 through 3, 12 and 13, and a pharmaceutically acceptable carrier, adjuvant, or vehicle.
* * * * *